United States Patent
Fordyce et al.

(10) Patent No.: US 10,160,772 B2
(45) Date of Patent: Dec. 25, 2018

(54) 5,6-DIHYDRO-4H-BENZO[B]THIENO-[2,3-D]AZEPINE DERIVATIVES

(71) Applicant: PULMOCIDE LIMITED, London (GB)

(72) Inventors: Euan Alexander Fraser Fordyce, Nottinghamshire (GB); Simon Fraser Hunt, London (GB); Stuart Thomas Onions, Nottinghamshire (GB); Vladimir Sherbukhin, Nottinghamshire (GB); Matthew Stephen Coates, London (GB); Daniel William Brookes, London (GB); Kazuhiro Ito, London (GB); Peter Strong, London (GB); John King-Underwood, Worcestershire (GB)

(73) Assignee: PULMOCIDE LIMITED, London (GB)

( * ) Notice: Subject to any disclaimer, the term of this patent is extended or adjusted under 35 U.S.C. 154(b) by 0 days.

(21) Appl. No.: 15/524,472

(22) PCT Filed: Dec. 18, 2015

(86) PCT No.: PCT/GB2015/054081
§ 371 (c)(1),
(2) Date: May 4, 2017

(87) PCT Pub. No.: WO2016/097761
PCT Pub. Date: Jun. 23, 2016

(65) Prior Publication Data
US 2017/0355718 A1    Dec. 14, 2017

(30) Foreign Application Priority Data

Dec. 18, 2014 (EP) ................................. 14199020
Mar. 10, 2015 (EP) ................................. 15158516

(51) Int. Cl.
*C07D 519/00* (2006.01)
*C07D 495/04* (2006.01)
*A61K 31/55* (2006.01)
*A61K 45/06* (2006.01)

(52) U.S. Cl.
CPC ............ *C07D 519/00* (2013.01); *A61K 31/55* (2013.01); *A61K 45/06* (2013.01); *C07D 495/04* (2013.01)

(58) Field of Classification Search
CPC .................................................. C07D 519/00
See application file for complete search history.

(56) References Cited

U.S. PATENT DOCUMENTS

| 8,999,969 B2 | 4/2015 | Mackman et al. |
| 9,732,098 B2 | 8/2017 | Hunt et al. |
| 9,926,335 B2 | 3/2018 | Hunt et al. |
| 2017/0037035 A1 | 2/2017 | Sunose et al. |
| 2017/0355717 A1 | 12/2017 | Hunt et al. |
| 2018/0179228 A1 | 6/2018 | Hunt et al. |

FOREIGN PATENT DOCUMENTS

| WO | 97/47625 | 12/1997 |
| WO | 00/64876 | 11/2000 |
| WO | 2011/005842 A1 | 1/2011 |
| WO | 2011/046954 A1 | 4/2011 |
| WO | 2012/016217 A1 | 2/2012 |
| WO | 2012/129562 A2 | 9/2012 |
| WO | 2016/022464 A1 | 2/2016 |
| WO | 2016/055791 A1 | 4/2016 |
| WO | 2016/055792 A1 | 4/2016 |
| WO | 2017123884 | 7/2017 |
| WO | 2017134133 | 8/2017 |

OTHER PUBLICATIONS

Sudo, et al.—Antiviral Research (2005) vol. 65: 125-131—"YM-53403, a unique anti-respiratory syncytial virus agent with a novel mechanism of action".
Xiong, et al—Bioorganic & Medicinal Chemistry Letters (2013) vol. 23 No. 24: 6789-6793—"Discovery of a potent respiratory syncytial virus RNA polymerase inhibitor".
Yajun Z

5,6-DIHYDRO-4H-BENZO[B]THIENO-[2,3-D]AZEPINE DERIVATIVES

CROSS REFERENCE TO RELATED APPLICATIONS

The present application is a National Stage Application claiming the priority of co-pending PCT Application No. PCT/GB2015/054081, filed Dec. 18, 2015, which in turn, claims priority from European Applications Nos. 14199020.0, filed Dec. 18, 2014 and 15158516.3, filed Mar. 10, 2015. Applicants claim the benefits of 35 U.S.C. § 120 as to the PCT application and priority under 35 U.S.C. § 119 as to the said European applications, and the entire disclosures of all applications are incorporated herein by reference in their entireties.

FIELD OF THE INVENTION

The invention relates to compounds which are intended to treat or prevent respiratory syncytial virus infections and associated disease particularly infections caused by the A and B strains thereof.

BACKGROUND OF THE INVENTION

Human respiratory syncytial virus (RSV) is a pneumovirus of the paramyxovirus family and the most common cause of bronchiolitis and pneumonia in infants under one year of age. Most children become infected with RSV prior to their second birthday resulting in 75-125,000 hospitalizations. The associated medical costs are thought to exceed $650 million annually in the United States alone. In addition, early-life, respiratory viral infections, notably with RSV, increase the risk of the subsequent development of childhood asthma (Holt and Sly, 2002). RSV infection can produce severe, lower respiratory tract disease in patients of any age. The elderly, as well as those having compromised cardiac, pulmonary or immune systems, are particularly vulnerable and it is estimated that some 14,000 deaths occur annually in the United States in subjects over 65 years old. In addition, RSV infection is increasingly regarded as an important precipitator of exacerbations in patients suffering from chronic obstructive pulmonary disease (COPD) (Mohan et al., 2010) as well as asthma (Newcomb and Peebles, 2009) and cystic fibrosis (Abman et al., 1988). In immuno-compromised adults, approximately 50% of upper respiratory tract infections with RSV progress to pneumonia.

The initial portal of entry by RSV is through the nose or eye rather than the mouth (Hall et al., 1981). Once established in the upper respiratory tract the virus is able to migrate readily into the lungs. The pathophysiology of RSV infection was investigated in a study of lung tissues obtained from deceased children (Johnson et al., 2007). Examination of tissues from four individuals revealed immunostaining of epithelial cells indicating the presence of RSV, without basal cells being affected. The epithelial localization of the pathogenic organism provides a challenge to treatment since a supra-effective concentration of the drug substance has to be maintained at the discrete cellular site to enable the infection to be treated and subsequently cleared.

The RSV virus exists as two antigenic sub-groups: A and B. Viruses of the RSV A strain were formerly regarded as the sub-group pathogens responsible for the majority of clinical disease and were reported to produce a more symptomatic pathology (Walsh et al., 1997; Panayiotou et al., 2014). A common RSV A strain is RSV A2 (Olivier et al., 2009). However, during a recent outbreak in China virus strains from the RSV B sub-group were found to predominate in the afflicted population (Zhang et al., 2010).

Over the last two decades considerable progress has been made in the treatment of a number of viral diseases including human immunodeficiency virus (HIV) and both hepatitis B and hepatitis C. In all these cases gold standard therapies have evolved that consist of combination treatments that were brought about, at least to some extent, in response to the emergence of drug resistant disease.

FDA-approved drugs for the treatment of acute RSV infections comprise of (aerosolised) ribavirin and the humanized, monoclonal antibody, palivizumab (Synagis). The latter agent targets the RSV fusion (F) protein and is limited to prophylactic use in high risk, paediatric patients. Furthermore, clinical variants resistant to neutralization by palivizumab were recently identified (Zhu et al., 2011) and therefore no truly effective vaccine is currently available. The use of ribavirin is limited by its low potency against the virus and by concerns over its side-effect profile. Consequently there is an urgent, unmet need for the discovery of novel, safe and effective therapies against RSV infection having an improved clinical profile. Moreover, in view of the emerging prominence of the RSV B strains in clinical disease it is highly desirable that these treatments be efficacious against infections arising from both RSV A and RSV B strains.

SUMMARY OF THE INVENTION

In a first aspect, the invention provides a compound of formula (I):
wherein:

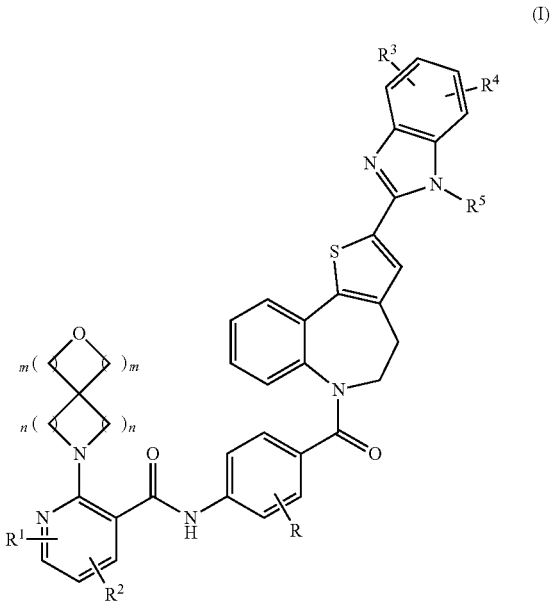

R represents hydrogen or halo;

$R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;

$R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano;

$R^3$ represents hydrogen, hydroxy, halo, cyano, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{0-3}$ alkylene$C_{3-6}$ cycloalkyl, $C_{0-3}$ alkylene-heterocyclyl, $C_{0-3}$ alkyleneamino, $C_{0-3}$ alkyleneNHC$_{1-5}$ alkyl, $C_{0-3}$ alkyleneN(C$_{1-5}$ alkyl)$_2$, $C_{1-5}$ acyl amino, $C_{0-3}$ alkyleneC(O)NHC$_{0-3}$ alkyl, $C_{0-3}$ alkyleneC(O)N(C$_{1-3}$ alkyl)$_2$, $C_{0-3}$ alkyleneN(C$_{0-3}$ alkyl)C(O)C$_{0-3}$ alkyl, $C_{0-3}$ alkyleneN(C$_{0-3}$ alkyl)C(O)NHC$_{0-3}$ alkyl, $C_{0-3}$ alkyleneN(C$_{0-3}$ alkyl)C(O)NC$_{1-3}$ alkyl)$_2$, $C_{0-3}$ alkyleneN(C$_{0-3}$ alkyl)S(O)$_q$C$_{1-6}$ alkyl, S(O)$_q$C$_{1-6}$ alkyl, $C_{0-3}$ alkyleneS(O)$_q$NHC$_{0-3}$ alkyl or $C_{0-3}$ alkyleneS(O)$_g$NC$_{1-3}$ alkyl)$_2$;

$R^4$ represents hydrogen, halo, cyano, $C_{1-4}$ alkyl, $C_{2-4}$ alkenyl, $C_{2-4}$ alkynyl, $C_{1-4}$ haloalkyl, $C_{0-3}$ alkyleneC$_{3-6}$ cycloalkyl, $C_{1-4}$ alkoxy or $C_{1-4}$ haloalkoxy;

$R^5$ represents hydrogen, $C_{1-6}$ alkyl, $C_{1-6}$ haloalkyl, $C_{0-3}$ alkyleneC$_{3-6}$ cycloalkyl, $C_{2-3}$ alkylene $C_{1-3}$ alkoxy, $C_{2-3}$ alkyleneC$_{1-3}$ haloalkoxy or $C_{2-3}$ alkyleneOH; and m, n and q represent integers which may independently be selected from 1 and 2;

or a pharmaceutically acceptable salt thereof ("compounds of the invention").

Biological data disclosed for the examples reveals that compounds of the invention inhibit the cytopathic effect associated with infection by RSV A strains, and in preferred embodiments also inhibit the cytopathic effect associated with infection by RSV B strains.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which one or two oxygen atoms (e.g. a single oxygen atom) is located within the alkyl chain, for example —CH$_2$CH$_2$OCH$_3$, —CH$_2$CH$_2$OCH$_3$, —CH$_2$OCH$_2$CH$_2$OCH$_3$, or —CH$_2$OCH$_3$. Thus in one embodiment the alkoxy is linked through carbon to the remainder of the molecule, for example —C$_n$alkyl-O—C$_m$alkyl in which n=1 or 2 and m=1 or 2. In one embodiment the alkoxy is linked through oxygen to the remainder of the molecule, for example —OC$_{1-4}$alkyl. In one embodiment the disclosure relates to straight chain alkoxy. In one embodiment the alkoxy is linked through oxygen to the remainder of the molecule but the alkoxy group contains a further oxygen atom, for example —OCH$_2$CH$_2$OCH$_3$.

Halo or halogen includes fluoro, chloro, bromo or iodo, in particular fluoro, chloro or bromo, especially fluoro or chloro.

Alkyl substituted by halo (haloalkyl) as employed herein refers to alkyl groups having 1 to 6 halogen atoms, for example 1 to 5 halogens, such as per haloalkyl, and in particular perfluoroalkyl, more specifically —CF$_2$CF$_3$ or CF$_3$.

Alkoxy substituted by halo (haloalkoxy) as employed herein refers to alkoxy groups having 1 to 6 halogen atoms, for example 1 to 5 halogens, such as perhaloalkoxy, in particular perfluoroalkoxy, more specifically —OCF$_2$CF$_3$ or —OCF$_3$.

$C_{1-6}$ alkyl includes $C_1$, $C_2$, $C_3$, $C_4$, $C_5$ and $C_6$ alkyl. $C_{1-6}$ alkoxy includes $C_1$, $C_2$, $C_3$, $C_4$, $C_5$ and $C_6$ alkoxy. $C_{1-6}$ haloalkyl includes $C_1$, $C_2$, $C_3$, $C_4$, $C_5$ and $C_6$ haloalkyl. $C_{1-6}$ haloalkoxy includes $C_1$, $C_2$, $C_3$, $C_4$, $C_5$ and $C_6$ haloalkoxy.

$C_{1-5}$ alkyl includes $C_1$, $C_2$, $C_3$, $C_4$ and $C_5$ alkyl.

$C_{1-4}$ alkyl includes $C_1$, $C_2$, $C_3$ and $C_4$ alkyl. $C_{1-4}$ alkoxy includes $C_1$, $C_2$, $C_3$ and $C_4$ alkoxy. $C_{1-4}$ haloalkyl includes $C_1$, $C_2$, $C_3$ and $C_4$ haloalkyl. $C_{1-4}$ haloalkoxy includes $C_1$, $C_2$, $C_3$ and $C_4$ haloalkoxy.

$C_{1-3}$ alkyl includes $C_1$, $C_2$ and $C_3$ alkyl. $C_{0-3}$ alkyl has the same meaning as $C_{1-3}$ alkyl and additionally includes for $C_0$ alkyl a hydrogen atom.

$C_{1-3}$ alkylene refers to an aliphatic carbon chain containing 1-3 carbon atoms which may be branched or straight chain, although straight chain is preferred. Examples include —CH$_2$—, —CH$_2$CH$_2$— or —CH(Me)-. $C_{0-3}$ alkylene has the same meaning as $C_{1-3}$ alkylene and additionally includes for $C_0$ alkylene a single bond.

$C_{1-5}$ acyl means —C(O)C$_{1-4}$ alkyl. An example of $C_{1-5}$ acyl amino is —NHCOMe.

$C_{3-6}$ cycloalkyl refers to a saturated, optionally branched carbocycle containing 3-6 carbon atoms. Unbranched examples include cyclopropyl, cyclobutyl, cyclopentyl and cyclohexyl. Branched examples include 2-methylcyclopropyl.

$C_{2-4}$ alkynyl or $C_{2-6}$ alkynyl refers to an unsaturated aliphatic, optionally branched moiety containing at least one triple bond and containing the specified number of carbon atoms. Examples include —C≡CH, —CH$_2$—C≡CH, —CH(CH$_3$)—C≡CH, —CH$_2$—C≡C—CH$_3$ and —C≡C—CH$_3$. Preferred alkynyl is $C_{2-3}$ alkynyl e.g. —C≡CH.

$C_{2-4}$ alkenyl or $C_{2-6}$ alkenyl refers to an unsaturated, aliphatic, optionally branched moiety containing at least one double bond and no triple bonds and containing the specified number of carbon atoms. Examples include —CH═CH$_2$, —CH$_2$—CH═CH$_2$, —CH(CH$_3$)—CH═CH$_2$, —CH$_2$—CH═CH(CH$_3$), —CH═CH—CH$_3$ and —CH═C(CH$_3$)$_2$. A preferred alkenyl is $C_{2-3}$ alkenyl, such as vinyl.

Amino refers to the group —NH$_2$. Examples of $C_{1-5}$ alkyl amino include —NHMe and —NHEt. Examples of (C$_{1-5}$ alkyl)$_2$ amino include —NMe$_2$ and —NEt$_2$. Examples of $C_{1-5}$ acyl amino include —NHC(O)Me.

Heterocyclyl refers to a cyclic radical having 4-6 ring atoms containing 1-3 heteroatoms selected from O, N and S and which may optionally be substituted e.g. by 1-3 groups selected from $C_{1-3}$ alkyl, $C_{1-3}$ haloalkyl, halo and hydroxyl. Examples include azetidinyl, pyrrolidinyl, piperidinyl, morpholinyl, thiomorpholinyl, piperazinyl and N-methylpiperazinyl.

Suitably n represents 1. Suitably m represents 2. Suitably n represents 1 and m represents 2.

Suitably q represents 2.

An example of $C_{2-3}$ alkyleneOH is CH$_2$CH$_2$OH.

In one embodiment of the present invention there is provided a compound of formula (Ia):

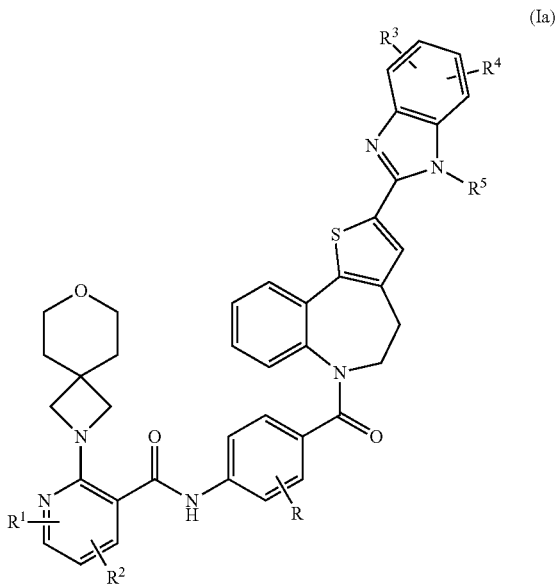

(Ia)

wherein R, $R^1$, $R^2$, $R^3$, $R^4$ and $R^5$ are defined as above for compounds of formula (I).

In a second embodiment of the invention there is provided a compound of formula (Ib):

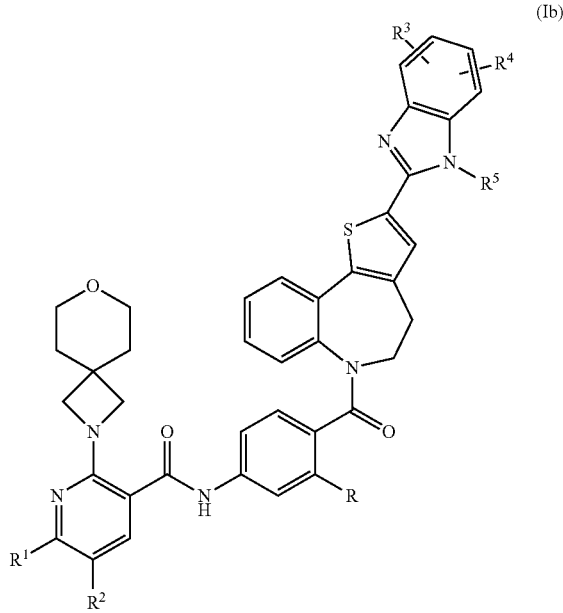

(Ib)

wherein R, $R^1$, $R^2$, $R^3$, $R^4$ and $R^5$ are defined as above for compounds of formula (I).

Particular embodiments of the invention, independently and in any combination, include the following:

Suitably R represents hydrogen. Alternatively, suitably R represents halo, particularly fluoro. R is suitably in the 3-position of the phenyl ring to which it is attached.

Suitably $R^1$ is selected from hydrogen, $C_{1-4}$ alkyl (e.g. methyl or ethyl), $C_{1-4}$ alkynyl (e.g. ethynyl), $C_{3-6}$ cycloalkyl (e.g. cyclopropyl) and $C_{1-4}$ alkoxy (e.g. methoxy), particularly hydrogen, $C_{1-4}$ alkyl and $C_{1-4}$ alkoxy. Suitably $R^2$ is selected from hydrogen and $C_{1-4}$ alkyl (e.g. methyl). Suitably one of $R^1$ and $R^2$ is methyl and the other is hydrogen or methyl. $R^1$ and $R^2$ are suitably, respectively, in the 6- and 5-positions of the pyridyl ring to which they are attached.

Suitably $R^1$ and $R^2$ are, respectively, in the 6- and 5-positions of the pyridyl ring to which they are attached and $R^1$ and $R^2$ both represent hydrogen or $R^1$ represents hydrogen and $R^2$ represents methyl or $R^1$ represents hydrogen and $R^2$ represents ethyl or $R^1$ represents methyl and $R^2$ represents hydrogen, or $R^1$ and $R^2$ both represent methyl, or $R^1$ represents methoxy and $R^2$ represents hydrogen. Further suitably $R^1$ represents hydrogen and $R^2$ represents ethynyl or $R^1$ represents hydrogen and $R^2$ represents cyclopropyl.

Suitably $R^3$ represents hydrogen, hydroxy, halo, cyano, $C_{1-6}$ alkyl, $C_{2-6}$ alkenyl, $C_{2-6}$ alkynyl, $C_{1-6}$haloalkyl, $C_{1-6}$ alkoxy, $C_{1-6}$ haloalkoxy, $C_{0-3}$ alkylene$C_{3-6}$ cycloalkyl, $C_{0-3}$ alkylene-heterocyclyl, amino, $C_{1-5}$ alkyl amino, $(C_{1-6}$ alkyl$)_2$ amino, $C_{1-5}$ acyl amino, $C_{0-3}$ alkyleneC(O)NHC$_{0-3}$ alkyl, $C_{0-3}$ alkyleneC(O)NC$_{1-3}$ alkyl$)_2$, $C_{1-3}$ alkyleneN(C$_{0-3}$ alkyl)C(O)C$_{0-3}$ alkyl, $C_{0-3}$ alkyleneN(C$_{0-3}$ alkyl)C(O)NHC$_{0-3}$ alkyl, $C_{0-3}$ alkyleneN(C$_{0-3}$ alkyl)C(O)N(C$_{1-3}$ alkyl)$_2$, $C_{0-3}$ alkyleneN(C$_{0-3}$ alkyl)S(O)$_q$C$_{1-6}$ alkyl, S(O)$_q$C$_{1-6}$ alkyl, $C_{0-3}$ alkyleneS(O)$_q$NHC$_{0-3}$ alkyl and $C_{0-3}$ alkyleneS(O)$_q$N(C$_{1-3}$ alkyl)$_2$; more suitably hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy and $C_{1-4}$ haloalkoxy; more suitably hydrogen, halo, cyano, $C_{1-4}$ alkyl, $C_{2-4}$ alkenyl, $C_{2-4}$ alkynyl, $C_{1-4}$ haloalkyl, $C_{1-4}$ alkoxy and $C_{1-4}$ haloalkoxy; more suitably hydrogen, halo (e.g. fluoro or chloro), cyano, $C_{1-4}$ alkyl (e.g. methyl or ethyl, especially methyl) and $C_{1-4}$ haloalkyl (e.g. trifluoromethyl); more suitably halo (e.g. chloro or fluoro), methyl, trifluomethyl and cyano; and yet more suitably methyl, fluoro and chloro. $R^3$ is suitably in the 6- or 7-position of the benzimidazole ring to which it is attached, more suitably in the 7-position.

Suitably $R^4$ is selected from hydrogen, halo, cyano, $C_{1-4}$ alkyl, $C_{2-4}$ alkenyl, $C_{2-4}$ alkynyl, $C_{1-4}$ haloalkyl, $C_{1-4}$ alkoxy and $C_{1-4}$ haloalkoxy; more suitably hydrogen and halo (e.g. fluoro), most suitably hydrogen. $R^4$ is suitably in the 5-position of the benzimidazole ring to which it is attached.

In an embodiment, $R^4$ represents hydrogen and $R^3$ does not represent hydrogen.

Suitably $R^5$ is selected hydrogen, $C_{1-6}$ alkyl, $C_{1-6}$ haloalkyl, $C_{0-3}$ alkyleneC$_{3-6}$ cycloalkyl, $C_{2-3}$ alkyleneC$_{1-3}$ alkoxy and $C_{2-3}$ alkyleneC$_{1-3}$ haloalkoxy; more suitably hydrogen, $C_{1-6}$ alkyl, $C_{1-6}$ haloalkyl, $C_{0-3}$ alkyleneC$_{3-6}$ cycloalkyl and $C_{2-3}$ alkyleneC$_{1-3}$ alkoxy; more suitably hydrogen and $C_{1-6}$ alkyl (e.g. methyl), particularly hydrogen.

Exemplary compounds of formula (I) are selected from the group consisting of:

N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-6-methyl-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-5-ethyl-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

N-(4-(2-(7-fluoro-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

N-(4-(2-(7-chloro-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

2-(7-oxa-2-azaspiro[3.5]nonan-2-yl)-N-(4-(2-(7-(trifluoromethyl)-1H-benzo[d]imidazol-2-yl)-5,6-dihydro-4H-benzo[b]thieno[2,3-d]azepine-6-carbonyl)phenyl)nicotinamide;

N-(4-(2-(6-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

N-(4-(2-(7-cyano-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

N-(4-(2-(7-fluoro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

N-(4-(2-(7-chloro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

5-methyl-N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

5-methyl-2-(7-oxa-2-azaspiro[3.5]nonan-2-yl)-N-(4-(2-(7-(trifluoromethyl)-1H-benzo[d]imidazol-2-yl)-5,6-dihydro-4H-benzo[b]thieno[2,3-d]azepine-6-carbonyl)phenyl)nicotinamide;

N-(4-(2-(7-cyano-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

N-(4-(2-(5,7-difluoro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

N-(4-(2-(7-fluoro-1H-benzo[d]imidazol-2-yl)-5,6-dihydro-4H-benzo[b]thieno[2,3-d]azepine-6-carbonyl)phenyl)-6-methyl-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-6-methoxy-2-(7-oxa-2-azaspiro[3.5]nonan-2-yl)nicotinamide;

N-(4-(2-(7-fluoro-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide;

N-(4-(2-(7-chloro-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide;

5,6-dimethyl-N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;

N-(4-(2-(7-cyano-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)-3-fluorophenyl)-5-methyl-2-(7-oxa-2-azaspiro[3.5]nonan-2-yl)nicotinamide;

N-(3-fluoro-4-(2-(7-methyl-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide and pharmaceutically acceptable salts of any one thereof.

Further exemplary compounds are selected from:

N-(4-(2-(7-ethyl-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-5-ethynyl-2-(7-oxa-2-azaspiro[3,5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-5-cyclopropyl-2-(7-oxa-2-azaspiro[3,5]nonan-2-yl)nicotinamide;

and pharmaceutically acceptable salts of any one thereof.

Pharmaceutically acceptable salts of compounds of formula (I) include in particular pharmaceutically acceptable acid addition salts of said compounds. The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

The definition of compounds of formula (I) is intended to include all stereoisomers of said compounds. Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

The definition of compounds of formula (I) is intended to include all tautomers of said compounds.

The definition of compounds of formula (I) is intended to include all solvates of said compounds (including solvates of salts of said compounds) unless the context specifically indicates otherwise. Examples of solvates include hydrates.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

Generic routes by which compound examples of the invention may be conveniently prepared are summarised below.

Compounds of formula (I) may be obtained by a general process (Scheme 1) whereby a thiophene carboxylic acid precursor (II), or a suitably protected derivative thereof, is treated with an activating agent, to generate a reactive, electrophilic carboxylic acid derivative, followed by reaction with a 1,2-phenylene diamine of formula (III), or a suitably protected derivative thereof and subsequent cyclisation of the resulting amide intermediate(s).

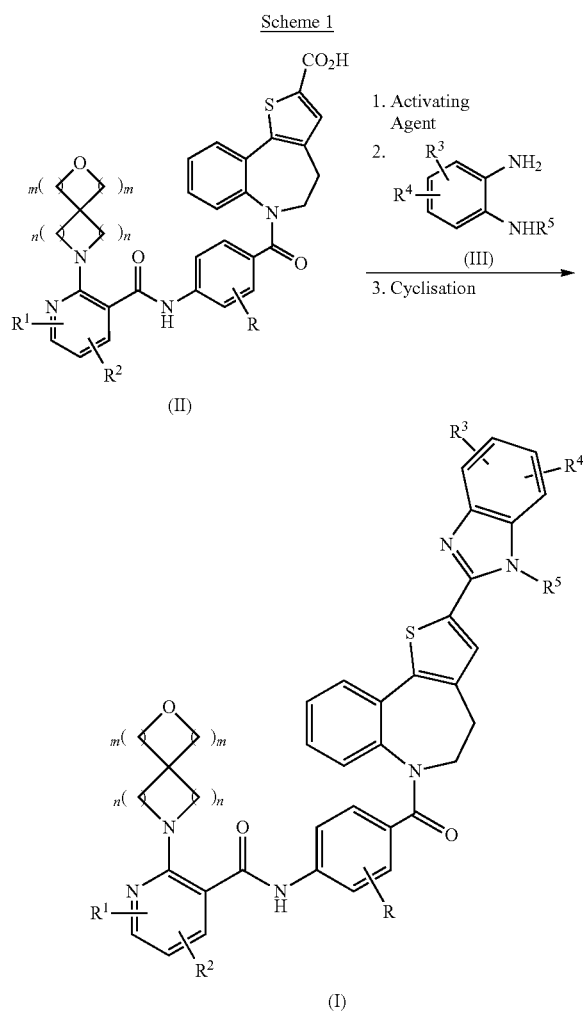

It will be understood by persons skilled in the art that, in some instances, the activated carboxylic acid derivative, such as an acid chloride, may be isolated or in other cases may be a transient intermediate that is not isolated, but generated in situ and used directly. Typically, the amide intermediate(s) resulting from the first two transformations is/are not isolated and are instead subjected to conditions that result in their dehydration and cyclisation to the corresponding benzimidazole examples of the invention, or a protected derivative thereof. The compounds of formula (I) are revealed, in those instances wherein one or more protective groups have been employed, by appropriate deprotection step(s).

Numerous and varied reagents are available for the activation of the carboxylate group including a wide selection of peptide coupling agents which can be selected based upon their compatibility with functionality represented in the carboxylic acid substrate. A convenient process for this step is exposure of the acid precursors of formula (II) to a stoichiometric excess of a volatile reagent such as oxalyl chloride or thionyl chloride, in an inert chlorinated solvent, typically DCM, ranging from RT to reflux. The remaining activating agent is usually removed by evaporation and the resulting acid chloride reacted directly with the phenylene diamine (III) in a non-polar, aprotic solvent, for example DCM, at or below ambient temperature and in the presence of a non-nucleophilic base, such as DI PEA. In instances in which the conversion of the acid into the acid chloride is required under neutral conditions (such as in the presence of an acid labile protective group) a suitable reagent is Ghosez's reagent (1-chloro-N,N,2-trimethyl-1-propenylamine), The generation of the acid chloride is conveniently carried out in an aprotic, halogenated solvent It will be understood by those skilled in the art that a mixture of regioisomeric amides may result from these transformations depending upon the substitution pattern of the diamine component (III), arising when any of $R^3$, $R^4$ and/or $R^5$ is other than hydrogen. It will also be evident that such isomeric mixtures are of no practical consequence and give rise to a unique benzimidazole product on cyclisation. Conditions suitable for this conversion include suspension or dissolution of the amide intermediate in glacial acetic acid, followed by heating, for example to 100-125° C., in order to promote loss of water and cyclisation.

Compounds of formula (II) are readily prepared by $S_NAr$ displacement reactions between an activated pyridine, of formula (IV), and an amine of formula (V) or suitably protected derivatives thereof, wherein R, $R^1$ and $R^2$ are as defined above for compounds of formula (I), $R^a$ is a simple alkyl group, such as methyl or ethyl, and LG is a suitable leaving group such as a halogen atom, for example chlorine (Scheme 2).

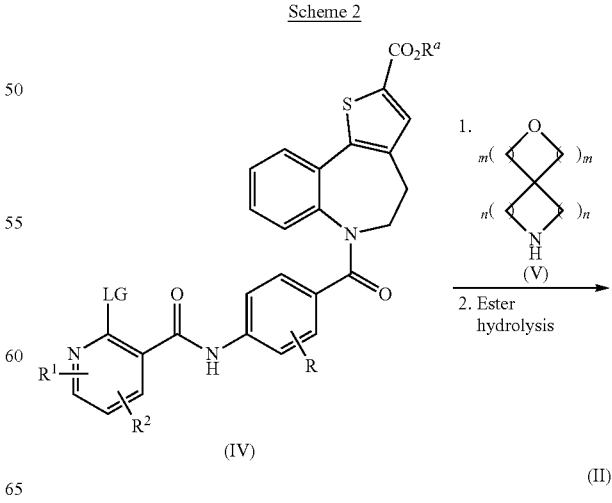

The compounds of formula (II) are obtained following subsequent hydrolysis of the ester —CO$_2$R$^a$ to the free acid. Conditions suitable for the displacement step are reaction in a polar, aprotic solvent such as DMF or NMP, optionally in the presence of a non-nucleophilic base, for example triethylamine and at elevated temperatures such as 100-150° C.

The alkyl ester may be conveniently hydrolysed by reaction with a strong acid, for example hydrochloric acid, in a mixture of polar protic solvents such as methanol and water. Alternatively the ester may be saponified by exposure to a strong inorganic base, for example lithium hydroxide, in a mixture of suitable aprotic and protic solvents, such THF:methanol:water. Such reactions may be subject to gentle heating to, for example, 30-50° C.

Intermediates represented by compounds of formula (IV) may be prepared by acylation of the anilines of formula (VI), with compounds of formula (VII), wherein R, R$^a$, R$^1$, and R$^2$ and LG are as defined herein above and LG$_1$ is a leaving group, such as a halogen atom, for example chlorine (Scheme 3). Conditions suitable for these transformations are reaction in a polar aprotic solvent such acetonitrile, in the presence of an organic base, as a 'proton sponge', for example pyridine at, or slightly above, RT for example at 40° C. Compounds of formula (VII) wherein, for example, LG$_1$ is chlorine are conveniently obtained from the corresponding acid by reaction with a chlorinating agent such as thionyl chloride, or oxalyl chloride optionally in the presence of a small, catalytic quantity of DMF.

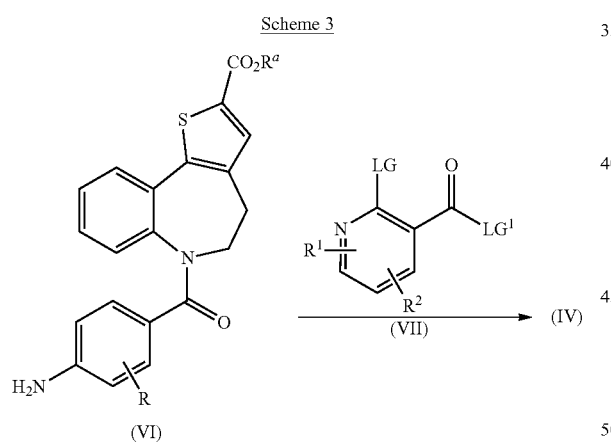

Scheme 3

The compound intermediates of formula (VI), wherein R and R$^a$ are as defined above, are readily obtained by the chemoselective reduction of the corresponding nitroarenes of formula (VIII) (Scheme 4). A common method employed for such conversions is reduction of the nitro group with a suitable metal, by a process referred to in the art as 'a dissolving metal reduction.' A metal frequently employed for these transformations is iron, usually in the form of a powder. The reaction is conducted in the presence of a proton source such as an ammonium salt, for example ammonium chloride and in a mixture of protic solvents, for example an alcohol such as IPA containing water and at elevated temperatures such as 70-80° C.

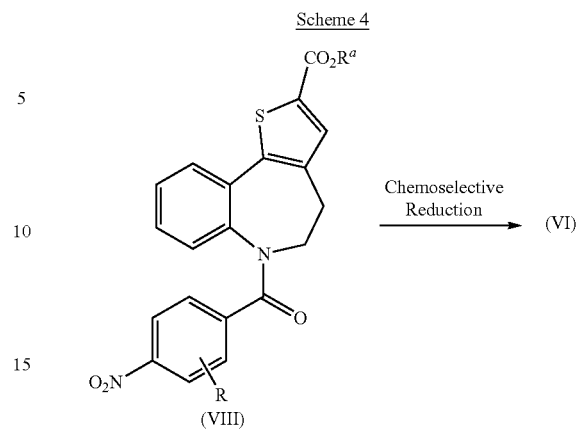

Scheme 4

Compounds of the current invention may also be prepared by use of the same or similar procedures as those disclosed above, applied to the nitroarene intermediate of formula (VIII), in an alternative synthetic sequence. Thus compounds of formula (I) can be generated by the S$_N$Ar reaction between an electrophilic pyridine derivative of formula (IX), and an amine of formula (V), or suitably protected derivatives thereof, wherein R R$^1$, R$^2$, R$^3$, R$^4$, R$^5$, and m and n are as defined above for compounds of formula (I), and LG is a suitable leaving group such as a halogen atom, for example chlorine (Scheme 5). Typical conditions employed for such nucleophilic displacements are reaction in a polar, aprotic solvent, such as NMP, in the presence of a non-nucleophilc, organic base, for example triethylamine and usually at elevated temperatures, such as 100-120° C.

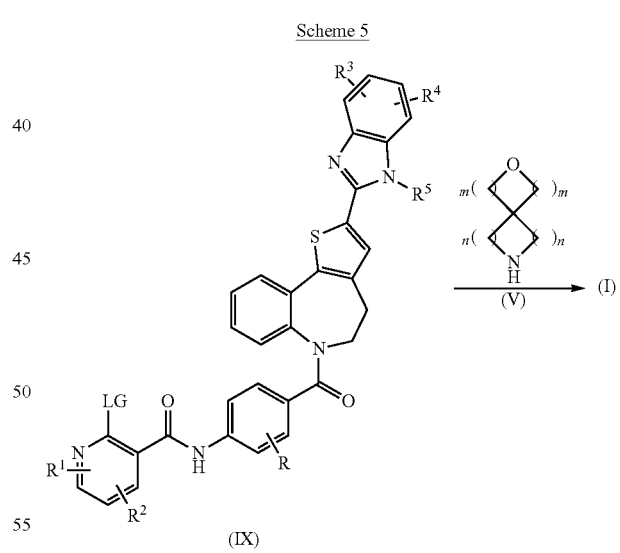

Scheme 5

The reactive pyridine derivatives of formula (IX) result from the acylation of the anilines of formula (X) with the nicotinic acid derivatives of formula (VII) (Scheme 6) by a process analogous to that described herein above for intermediates of formula (IV). A suitable procedure for carrying out the N-acylation step is the generation of an acid chloride (VII, LG$^1$=Cl), optionally performed in situ, for example with oxalyl chloride or the like, in DMF, followed by reaction with the amine substrate (X) in a basic solvent, such as pyridine, typically at ambient temperature.

Scheme 6

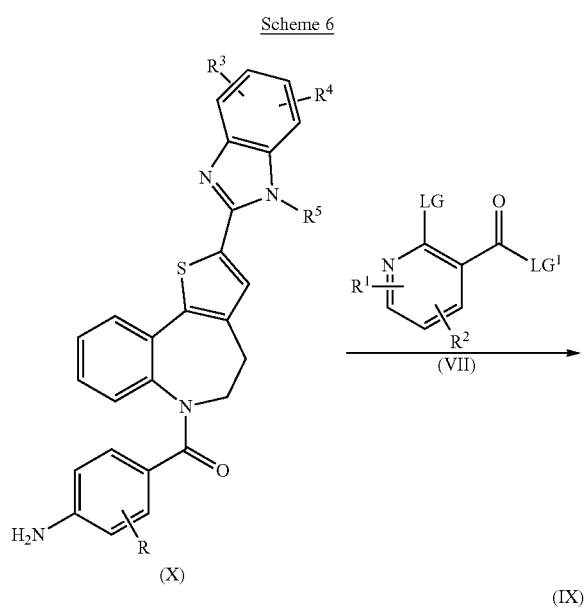

Those skilled in the art will appreciate that it is sometimes advantageous, for reasons of functional group compatibility and/or efficiency (for example to eliminate the need for protective groups) to conduct the same or similar synthetic transformations in a different sequence. Thus the compounds of the current invention may be also be prepared by the reaction of the aniline components of formula (X) with a fully elaborated nicotinic acid derivative of formula (XI) wherein $R^1$ $R^2$, m and n are as defined herein for the compounds of formula (I) and $LG_2$ is a suitable leaving group. (Scheme 7). The acylation step may be achieved using, for example, an acid halide, such as an acid chloride, ($LG_2$=Cl) optionally, formed and used in situ, as described above. Alternatively the corresponding acid ($LG_2$=OH) may be transformed into the desired amide product employing peptide coupling agents, of which a wide selection is available in the art.

Scheme 7

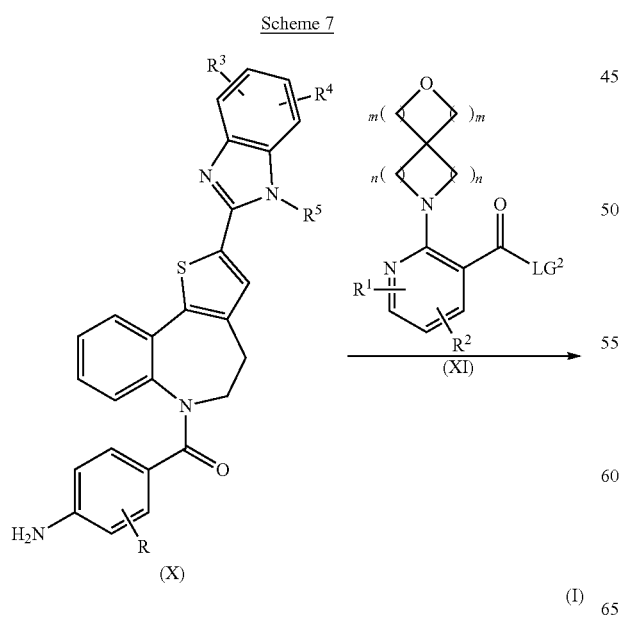

The compounds of formula (X) are readily accessible, from the nitrobenzoyl-substituted thiophene carboxylic acids of formula (XII) using generic procedures similar to those recited above for the conversion of compounds of formula (II) into examples of the invention (Scheme 1), followed by chemoselective reduction of the nitro group (Scheme 8). A commonly employed method for the selective reduction of a nitro benzene into the corresponding aniline is a dissolving metal reduction as outlined herein above for the conversion of the intermediates of formula (VIII) into those of formula (VI). Such reductive transformations may be effected with metals, such as zinc in the form of a powder and are typically conducted in an aq mixture of water miscible solvents, for example in methanol, THF and water, at ambient temperature. Another metal which is routinely used for such transformations is iron, also in the form of a powder, in the presence of a 'proton' source, typically aqueous ammonium chloride. Conditions suitable for the reductive process are alcoholic solvents, for example IPA, at elevated temperatures such as 70-80° C.

Scheme 8

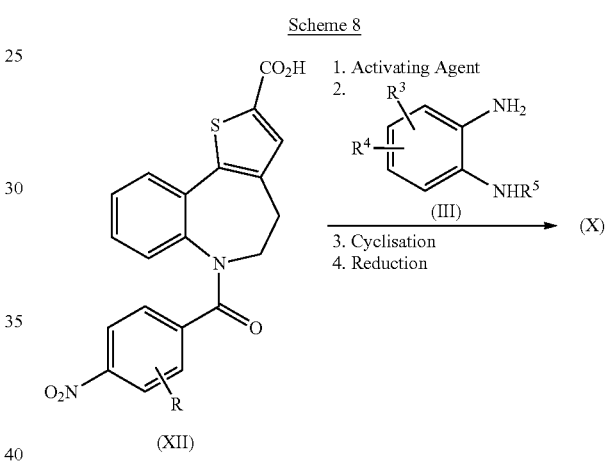

The 2-aminonicotinic acid intermediates of formula [(XI); $LG^2$=OH] may be elaborated from alkyl 2-halonicotinates of formula (VIIa), wherein $R^1$, $R^2$ and LG are as defined above, and $R^b$ is a simple alkyl group, by an $S_NAr$ displacement reaction with an amine of formula (V), followed by hydrolysis of the benzoate ester (Scheme 9). Conditions suitable for the amination step include those described above for the reaction of the halopyridine intermediates of formula (IX) and of formula (IV) to provide compounds of the invention and intermediates of formula (II) respectively Scheme 9

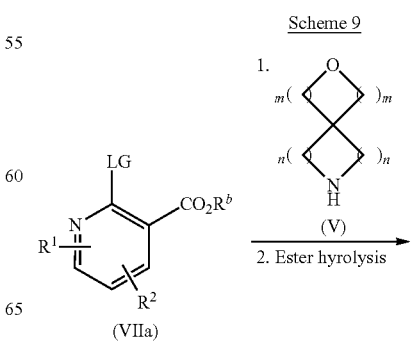

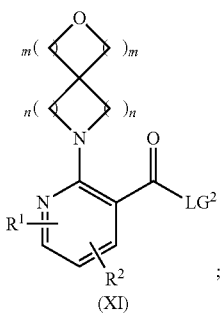

LG² = OH

A subgenus of functionalised nicotinic acids of particular interest are those of formula (XIa) in which m and n are as defined above for compounds of formula (I), R¹ is hydrogen and R² is a C-5 substituent (Scheme 10). In some instances the intermediates of formula (XIa) are not commercially available or are novel and require bespoke synthesis. A method of preparing such compounds is the use of a metal-catalysed, carbon-carbon bond forming reaction on a substrate of formula (XIb) wherein m and n are as defined above and $R^b$ is a simple alkyl group. Those skilled in the art will appreciate that an extensive methodology exists for conducting transformation of this type and wide range of suitable conditions may be used.

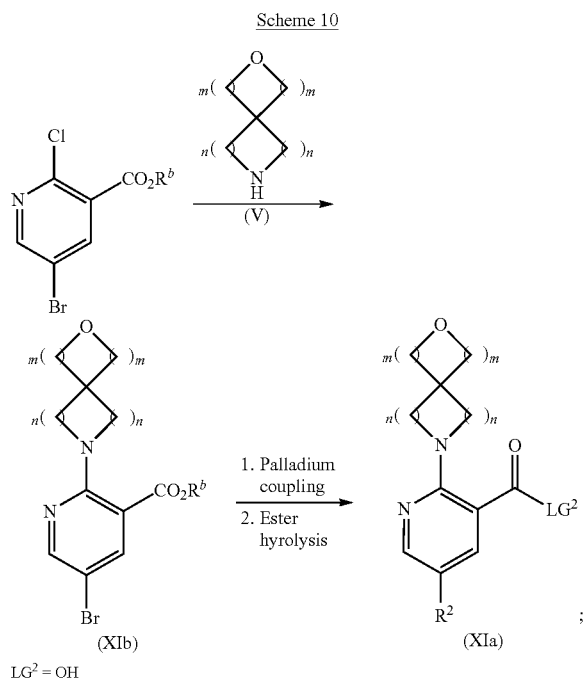

LG² = OH

A pre-eminent process is a Suzuki cross-coupling reaction which may be undertaken on an aryl bromide of formula (IXb), and a boronic acid of formula $R^2B(OH)_2$ or similar, using a palladium catalyst. A typical catalyst is bis(triphenylphosphine)palladium(II) dichloride. It is common for such reactions to be run under basic conditions, typically in the presence of bases such as potassium carbonate or cesium carbonate and for them to be heated, for example to 80-100° C. An extensive range of solvents such as THF, dioxane, ethanol and mixtures of toluene and water are applicable. The compounds of formula (XIa) are then obtained by hydrolysis of the ester which may be accomplished under either acidic or basic conditions in the presence of protic solvents and water such as aqueous methanol. The aryl bromide substrates of formula (XIb) are readily obtained by treatment of an alkyl 5-bromo-2-chloronicotinate with an amine of formula (V). Typical conditions for the chemoselective displacement are reaction in a polar, non-protic solvent such N-methyl pyrrolidine in the presence of a base, for example triethylamine, with heating if required.

The thiophene carboxylic acids of formula (XII) are readily derived from the corresponding esters of formula (VIII), which constitute intermediates common to the synthetic strategies, disclosed herein, for preparing compounds of the invention (Scheme 11). The hydrolysis may be effected under either acidic or basic conditions. For example the esters of formula (VIII) may be saponified by exposure to a strong inorganic base, such a aqueous sodium hydroxide, in a mixture of water miscible solvents, for example THF and methanol at moderately elevated temperatures such as 30-50° C.

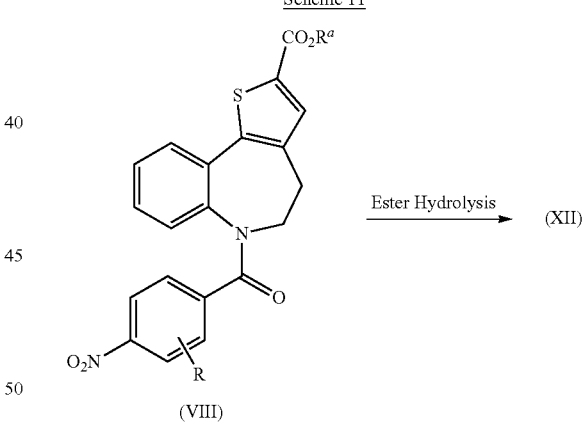

The nitroarenes of formula (VIII) are expediently prepared by reaction of an amino ester of formula (XIII) with a suitable 4-nitrobenzoic acid derivative of formula (XIV), wherein R and $R^a$ are as defined above and $LG^3$ is a reactive leaving group such as a halogen, for example a chlorine atom (Scheme 12). For example the acylation may be carried out by treating the amine (XIII), [either as its free base or as a salt] with an acid chloride derivative (XIV; $LG^3$=Cl) in a polar, non-protic solvent, such as acetonitrile and in the presence of an organic base, typically pyridine at, or below, ambient temperatures such as 0-20° C.

Scheme 12

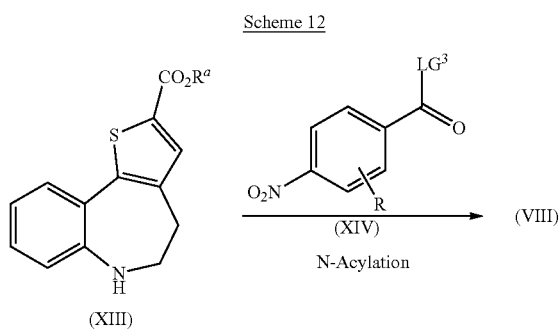

It will be evident to those skilled in the art that the N-acylation step may also be readily achieved on the free acids (LG³=OH) corresponding to compounds of formula (XIV) under conditions commonly employed for the formation of amide bonds, for example with a peptide coupling reagent, such as a uronium coupling reagent, for example with O-(benzotriazol-1-yl)-N,N,N',N'-tetramethyluronium tetrafluoroborate (TBTU) and the like. Typically such reactions are conducted in the presence of a non nucleophilic base such as Hunig's base and in a non-protic, polar solvent, for example in DMF.

The ester derivatives of formula (XIII) may be prepared from the previously disclosed acid (XV) by any of the methods commonly employed in the art (Scheme 13). A small scale procedure for the preparation of this compound has been described (Peesapati and Lingaiah 1993) starting from the N-tosyl azepinone (XVI), via the protected thiophene ester (XVII). The methodology revealed by the authors provides the acid (XV) in three steps and an overall yield of ~32%, following purification by thin-layer chromatography.

Scheme 13

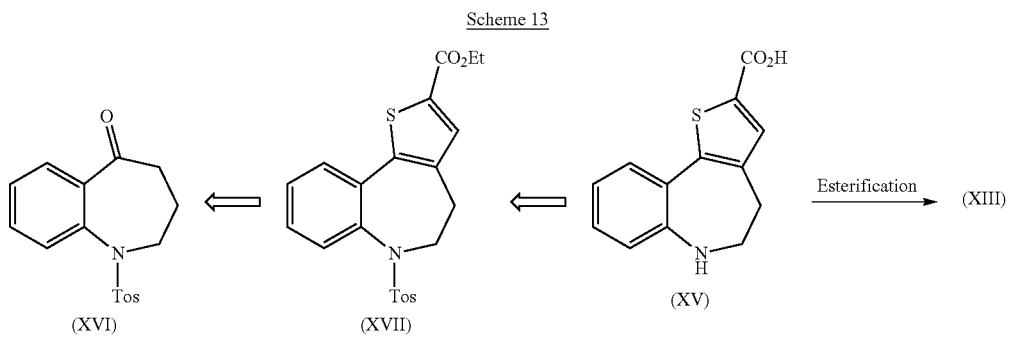

Advantageously, the azepine esters of formula (XIII) are readily obtained by the acid-mediated, chemoselective removal of the carboxybenzyl (Cbz) protective group from an intermediate of formula (XVIII), in which $R^a$ is as defined above (Scheme 14). Suitable conditions for the hydrolysis of the urethane group are exposure to an anhydrous acid HX wherein X is halo (such as HCl) in an alcoholic solvent ($R^a$OH), such as ethanolic HCl, at elevated temperatures, for example at reflux. In this instance the desired azepine esters may be isolated from the reaction medium as the corresponding acid salts (XIIIa). The N-Cbz azepine esters (XVIII) may be prepared starting from the N-Cbz azepinone (XIX) using procedures which are analogous to those reported for the preparation of the tosyl derivative (XVII) (see Experimental Section).

Scheme 14

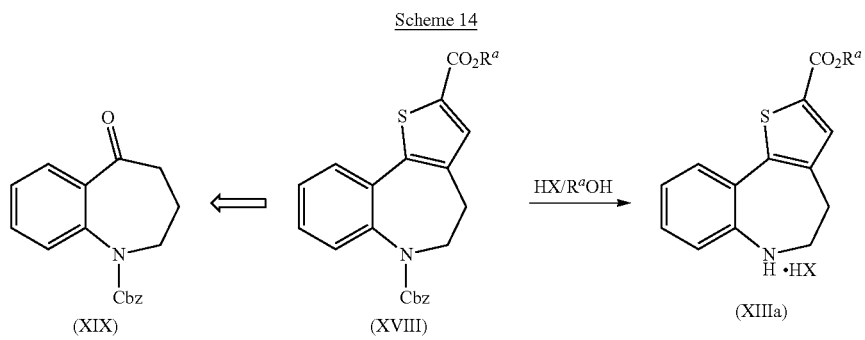

Alternatively the compounds of formula (VIII) may be obtained by condensation of a chloro-enal of formula (XXI) with an alkyl 2-mercaptoacetate of formula (XX), wherein R and $R^a$ are as defined above, in the presence of a non nucleophilic base (Scheme 15). Typical conditions which may be used to effect this transformation are reaction in non-protic, basic solvents such as a mixture pyridine and triethylamine, at elevated temperatures, for example at 70-110° C.

Scheme 15

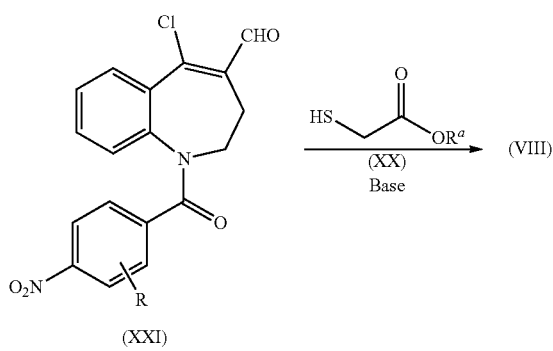

The chloro-enals of formula (XXI) are accessible by the chloro formylation of the N-acyl azepinones of formula (XXII). Such conversions may be carried out with a Vilsmeier reagent formed in situ, for example by the reaction between DMF and phosphoryl trichloride (Scheme 16). The reaction is conveniently undertaken in DMF as the solvent and the Vilsmeier reagent is pre-formed before addition of the substrate, usually at reduced temperature, such as 0-5° C. If required the reaction may be then be heated, for example to 70-80° C.

Scheme 16

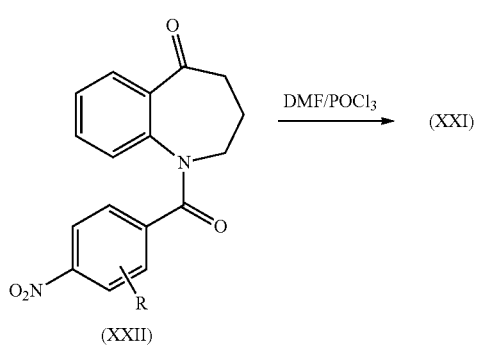

The azepine amide intermediates of formula (XXII) are readily generated by acylation of the commercially available 3,4-dihydro-1H-benzo[b]azepin-5(2H)-one with a suitable benzoic acid derivative (XIV) (Scheme 17). Exemplary conditions for this process are the same as those described herein above for the conversion of the azepine intermediates of formula (XIII) into the N-benzoyl derivatives (VIII) (Scheme 12).

Scheme 17

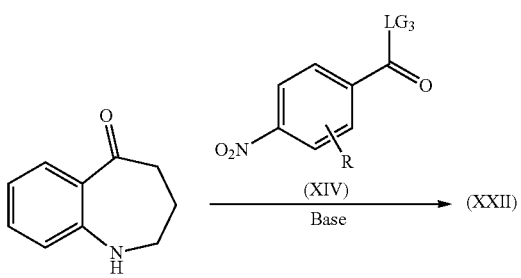

Protective groups and the means for their removal are described in "Protective Groups in Organic Synthesis", by T. W. Greene and P. G. M. Wuts, John Wiley & Sons Inc; 4th Rev Ed., 2006, ISBN-10: 0471697540. A review of methodologies for the preparation of amides is covered in: 'Amide bond formation and peptide coupling' Montalbetti, C. A. G. N. and Falque, V. Tetrahedron, 2005, 61, 10827-10852.

Novel intermediates as described herein (such as, for example, compounds of formula (IX), (IXa) and (X) form a further aspect of the invention, as do salts thereof, such as pharmaceutically acceptable salts.

Compounds of the invention are useful as pharmaceuticals.

In an embodiment there is provided a pharmaceutical composition comprising a compound of the invention optionally in combination with one or more pharmaceutically acceptable diluents or carriers.

Suitably compounds of the invention are administered topically to the lung or nose, particularly, topically to the lung. Thus, in an embodiment there is provided a pharmaceutical composition comprising a compound of the invention optionally in combination with one or more topically acceptable diluents or carriers.

Suitably compositions for pulmonary or intranasal administration include powders, liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

According to one specific aspect of the invention there is provided a pharmaceutical composition comprising a compound of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also, be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the compound of the disclosure in finely divided form, typically with an MMD of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. an MMD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

Compounds of the invention are useful in the treatment of RSV infection and for the prevention or treatment of disease associated with RSV infection.

In an aspect of the invention there is provided use of a compound of the invention in the manufacture of a medicament for the treatment of RSV infection and for the prevention or treatment of disease associated with RSV infection.

In another aspect of the invention there is provided a method of treatment of a subject infected with RSV which comprises administering to said subject an effective amount of a compound of the invention.

In another aspect of the invention there is provided a method of prevention or treatment of disease associated with RSV infection in a subject which comprises administering to said subject an effective amount of a compound of the invention.

Compounds of the invention may be used in a prophylactic setting by administering them prior to infection.

In one embodiment the RSV infection is RSV A strain infection (e.g. with an RSV A2 strain). In another embodiment the RSV infection is RSV B strain infection (e.g. with RSV B Washington strain).

Subjects include human and animal subjects, especially human subjects.

Compounds of the invention are especially useful for the treatment of RSV infection and for the prevention or treatment of disease associated with RSV infection in at risk subjects. At risk subjects include premature infants, children with congenital defects of the lung or heart, immunocompromised subjects (e.g. those suffering from HIV infection), elderly subjects and subjects suffering from a chronic health condition affecting the heart or lung (e.g. congestive heart failure or chronic obstructive pulmonary disease).

Compounds of the invention may be administered in combination with a second or further active ingredient. Compounds of the invention may be co-formulated with a second or further active ingredient or the second or further active ingredient may be formulated to be administered separately by the same or a different route. According to an aspect of the invention there is provided a kit of parts comprising (a) a pharmaceutical composition comprising a compound of the invention optionally in combination with one or more diluents or carriers; (b) a pharmaceutical composition comprising a second active ingredient optionally in combination with one or more diluents or carriers; (c) optionally one or more further pharmaceutical compositions each comprising a third or further active ingredient optionally in combination with one or more diluents or carriers; and (d) instructions for the administration of the pharmaceutical compositions to a subject in need thereof. The subject in need thereof may suffer from or be susceptible to RSV infection.

Second or further active ingredients include active ingredients suitable for the treatment or prevention of RSV infection or disease associated with RSV infection or conditions co-morbid with RSV infection.

Second or further active ingredients may, for example, be selected from anti-viral agents (such as other anti-RSV agents) including F protein inhibitors (including anti-F-protein antibodies, such as palivizumab), RNA polymerase inhibitors and ribavirin and anti-inflammatory agents.

Compounds of the invention may be administered at a suitable interval, for example once per day, twice per day, three times per day or four times per day.

A suitable dose amount for a human of average weight (50-70 kg) is expected to be around 50 µg to 10 mg/day e.g. 500 µg to 5 mg/day although the precise dose to be administered may be determined by a skilled person.

Compounds of the invention are expected to have one or more of the following favourable attributes:

potent inhibition of cytopathic effect and/or virus replication and/or F-protein expression in humans (or an animal model, or an in vitro system) caused by RSV A strains, such as the A2 strain;

potent inhibition of cytopathic effect and/or virus replication and/or F-protein expression in humans (or an animal model, or an in vitro system) caused by RSV B strains;

long duration of action in lungs, preferably consistent with once daily dosing; acceptable safety profile, especially following topical administration to the lung or nose.

EXPERIMENTAL SECTION

Abbreviations used herein are defined below (Table 1). Any abbreviations not defined are intended to convey their generally accepted meaning.

TABLE 1

| Abbreviations | |
|---|---|
| AcOH | glacial acetic acid |
| aq | aqueous |
| BALF | bronchoalveolar lavage fluid |
| BEAS2B | SV40-immortalised human bronchial epithelial cell line |
| br | broad |
| BSA | bovine serum albumin |
| CatCart ® | catalytic cartridge |
| Cbz | carboxybenzyl |
| $CC_{50}$ | 50% cell cytotoxicity concentration |
| CDI | 1,1-carbonyl-diimidazole |
| CPE | cytopathic effect |
| d | doublet |
| DCM | dichloromethane |
| DMEM | Dulbecco's Modified Eagle Medium |
| DMSO | dimethyl sulfoxide |
| dppf | 1,1'-bis(diphenylphosphino)ferrocene |
| DSS | dextran sodium sulphate |
| (ES+) | electrospray ionization, positive mode |
| Et | ethyl |
| EtOAc | ethyl acetate |
| FBS | foetal bovine serum |
| HATU | 1-[bis(dimethylamino)methylene]-1H-1,2,3-triazolo[4,5-b]pyridinium 3-oxid hexafluorophosphate |
| Hep2 | human laryngeal epithelioma cell line 2 |
| hr | hour(s) |
| HRP | horse radish peroxidase |
| $IC_{50}$ | 50% inhibitory concentration |
| $IC_{75}$ | 75% inhibitory concentration |
| $IC_{90}$ | 90% inhibitory concentration |
| IgG | immunogloblin G |

TABLE 1-continued

| Abbreviations | |
|---|---|
| IPA | isopropyl alcohol |
| $^{i}$Pr | isopropyl |
| $(M + H)^{+}$ | protonated molecular ion |
| Me | methyl |
| MeCN | acetonitrile |
| MeOH | methanol |
| MHz | megahertz |
| MMD | mass median diameter |
| MOI | multiplicity of infection |
| min | minute(s) |
| m/z: | mass-to-charge ratio |
| NMP | N-methylpyrrolidine |
| NMR | nuclear magnetic resonance (spectroscopy) |
| nt | not tested |
| OD | optical density |
| PBS | phosphate buffered saline |
| prep HPLC | preparative high performance liquid chromatography |
| PG | protective group |
| Ph | phenyl |
| p-TSA | 4-methylbenzenesulfonic acid |
| q | quartet |
| RT | room temperature |
| RP HPLC | reverse phase high performance liquid chromatography |
| RPMI | Roswell Park Memorial Institute medium |
| RSV | respiratory syncytial virus |
| s | singlet |
| sat | saturated |
| SCX | solid supported cation exchange (resin) |
| SDS | sodium dodecyl sulphate |
| $S_{N}Ar$ | nucleophilic aromatic substitution |
| t | triplet |
| TBAF | tetra-n-butylammonium fluoride |
| THF | tetrahydrofuran |
| TMB | 3,3',5,5'-tetramethylbenzidine |
| Tos | p-toluenesulfonyl |
| WB | washing buffer |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography

Method 1: Waters X-Select CSH column C18, 5 µm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 50% MeCN; 5.5-5.6 min, ramped from 50% MeCN to 95% MeCN; 5.6-6.5 min, held at 95% MeCN.

Method 2: Waters X-Select CSH column C18, 5 µm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Method 3: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 15% MeCN; 0.0-7.5 min, ramped from 15% MeCN to 50% MeCN; 7.5-8.0 min, ramped from 50% MeCN to 95% MeCN; 8.0-10.0 min, held at 95% MeCN.

Method 4: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 20% MeCN; 0.0-7.5 min, ramped from 20% MeCN to 40% MeCN; 7.5-8.0 min, ramped from 40% MeCN to 95% MeCN; 8.0-10.0 min, held at 95% MeCN.

Method 5: Waters X-Select CSH column C18, 5 μm (19×50 mm), flow rate 28 mL min$^{-1}$ eluting with a H$_2$O-MeCN gradient containing 0.1% v/v formic acid over 10 min using UV detection at 254 nm. Gradient information: 0.0 min, 30% MeCN; 0.0-7.5 min, ramped from 30% MeCN to 60% MeCN; 7.5-8.0 min, ramped from 60% MeCN to 95% MeCN; 8.0-10.0 min, held at 95% MeCN.

Method 6: Waters X-Bridge Prep column C18, 5 μm (19×50 mm), flow rate 28 mL min$^{-1}$ eluting with a 10 mM NH$_4$HCO$_3$-MeCN gradient over 6.5 min using UV detection at 254 nm. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Analytical Methods

Reverse Phase HPLC Conditions for the LCMS Analytical Methods

Methods 1a and 1b: Waters Xselect CSH C18 XP column, 2.5 μm (4.6×30 mm) at 40° C.; flow rate 2.5-4.5 mL min$^{-1}$ eluted with a H$_2$O-MeCN gradient containing either 0.1% v/v formic acid (Method 1a) or 10 mM NH$_4$HCO$_3$ in water (Method 1b) over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01-3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy $^1$H NMR spectra were acquired on a Bruker Avance III spectrometer at 400 MHz using residual undeuterated solvent as reference and unless specified otherwise were run in DMSO-d$_6$.

Preparation of Intermediates

Known synthetic intermediates were procured from commercial sources or were obtained using published literature procedures. Additional intermediates were prepared by the representative synthetic processes described herein.

2-Chloronicotinoyl Chloride

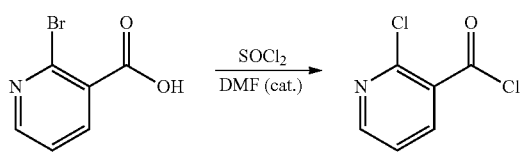 [SMILES: O=C(O)c1cccnc1Br ; "SOCl2" ; O=C(Cl)c1cccnc1Cl]

Thionyl chloride (70 mL) was added in one portion to neat 2-bromonicotinic acid (10.0 g, 49.5 mmol) at RT, followed by 2-3 drops of DMF and the mixture was heated at reflux for 4 hr. The reaction was cooled to RT and the excess thionyl chloride was removed by evaporation in vacuo. The residue was recrystallised from iso-hexane to afford the title compound as a light yellow solid (7.81 g, 90% pure by $^1$H-NMR, 81%). This material was used in subsequent steps without additional purification.

N-(2-Ethyl-6-nitrophenyl)acetamide

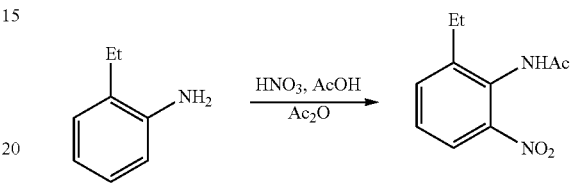

To a solution of 2-ethylaniline (5.1 mL, 41 mmol) and acetic anhydride (7.0 mL, 74 mmol) in acetic acid (20 mL) at 0° C. was added fuming nitric acid (3.1 mL, 69 mmol). The resulting mixture was maintained at 0° C. for 1 hr and then slowly warmed to RT over 1 hr and stirred at this temperature for 22 hr. The reaction mixture was cooled to 0° C., treated with additional fuming nitric acid (3.1 mL, 69 mmol) and then allowed to warm to RT. After 5 hr the reaction mixture was poured into ice water (300 mL) and extracted with EtOAc (200 mL). The organic layer was separated and retained and the aq phase was extracted with EtOAc (200 mL). The combined organic extracts were washed with brine (150 mL) and dried and evaporated in vacuo. The residue was purified by flash column chromatography (SiO$_2$, 80 g, 0-100% EtOAc in isohexane, gradient elution) to afford the title compound as a dark yellow solid (2.67 g, 80% pure by $^1$H NMR, 31%); R$^t$ 1.40 min (Method 1a); m/z 209 (M+H)$^+$ (ES$^+$). This material was used in subsequent steps without additional purification.

2-Ethyl-6-nitroaniline

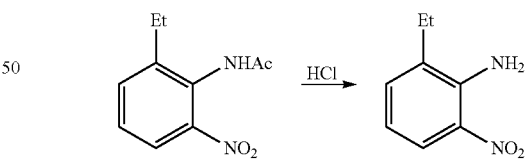

To a solution of N-(2-ethyl-6-nitrophenyl)acetamide (2.50 g, 12.0 mmol) in EtOH (15 mL) at RT was added conc hydrochloric acid (20 mL, 658 mmol). The mixture was heated at reflux for 18 hr and was then cooled, poured onto ice (50 g) and basified to pH 14 by the addition of 2 M sodium hydroxide. The resulting precipitate was collected by filtration and was washed with water (20 mL). The filtrates were extracted with DCM (3×60 mL) and the combined organics were dried and evaporated in vacuo. The residue was combined with the filter and obtained earlier to afford the title compound as a dark brown oil (1.81 g, 88% pure by HPLC, 91%); R$^t$ 2.01 min (Method 1a); m/z 167

(M+H)⁺ (ES⁺). This material was used in subsequent steps without additional purification.

3-Ethylbenzene-1,2-diamine

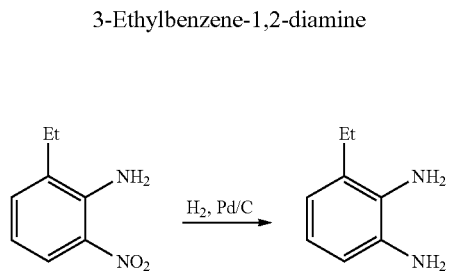

A solution of 2-ethyl-6-nitroaniline (1.61 g, 9.69 mmol) in a mixture of EtOH (40 mL) and 1 M hydrochloric acid (2.0 mL) was passed through a Thales H-cube (1.0 mL·min⁻¹, 23° C., 55 mm 10% Pd/C Cat-Cart, full hydrogen mode). After two passes the crude mixture was combined with a second batch of material (1.20 mmol scale) obtained in the same manner. The volatiles were evaporated in vacuo to afford the title compound as a viscous dark brown oil (1.35 g, 78% pure by H PLC, 91%); R$^r$ 0.34 min (Method 1a); m/z 137 (M+H)⁺ (ES⁺). This material was used in the subsequent step without additional purification.

Methyl 5-bromo-2-(7-oxa-2-azaspiro[3.5]nonan-2-yl)nicotinate

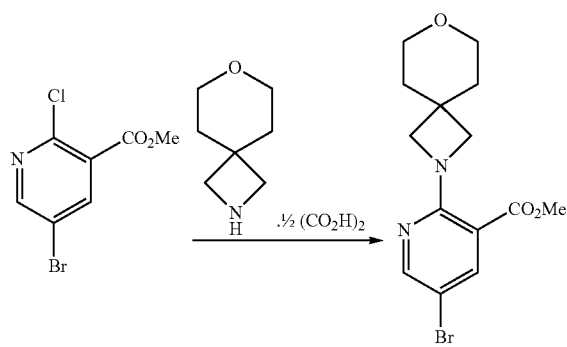 [SMILES: COC(=O)c1cc(Br)cnc1Cl ; C1CC2(CCO1)CNC2 ; COC(=O)c1cc(Br)cnc1N1CC2(CCOCC2)C1]

To a solution of methyl 5-bromo-2-chloronicotinate (5.75 g, 23.0 mmol) and 7-oxa-2-azaspiro[3.5]nonane hemi oxalate (5.98 g, 27.5 mmol) in NMP (55 mL) was added Et₃N (9.60 mL, 68.9 mmol). The reaction mixture was heated to 120° C. for 1 hr and was then cooled to RT and diluted with water (250 mL) and EtOAc (200 mL). The aq layer was separated and was extracted with EtOAc (200 mL). The combined organic layers were washed with water (3×300 mL), dried and evaporated in vacuo to give the title compound as a brown solid (7.22 g, 92% yield); R$^r$ 2.15 min (Method 1a); m/z 340/342 (M+H)⁺ (ES⁺); ¹H NMR δ: 1.68 (4H, br t), 3.52 (4H, br t), 3.72 (4H, s), 3.81 (3H, s), 8.01 (1H, d), 8.35 (1H, d).

Methyl 2-(7-oxa-2-azaspiro[3.5]nonan-2-yl)-5-vinylnicotinate

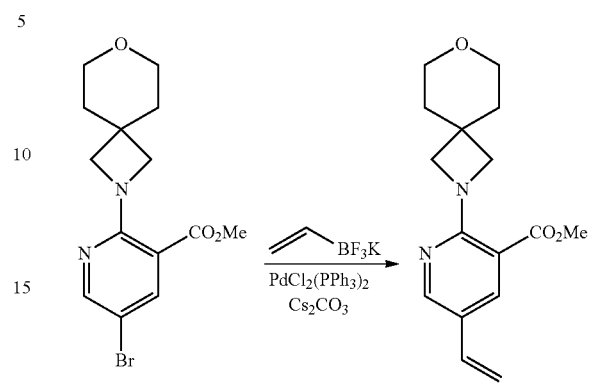

A mixture of methyl 5-bromo-2-(7-oxa-2-azaspiro[3.5]nonan-2-yl)nicotinate (1.50 g, 4.40 mmol), potassium vinyltrifluoroborate (1.18 g, 8.79 mmol), cesium carbonate (4.30 g, 13.2 mmol) and bis(triphenylphosphine) palladium(II) dichloride (0.15 g, 0.22 mmol) were charged into a vial and sealed. The vial was evacuated, and re-filled with nitrogen three times and then water (1.5 mL) and 1,4-dioxane (14.7 mL) were added. The reaction mixture was heated at 85° C. for 3 hr, cooled and filtered through a celite pad. The pad was washed with EtOAc (250 mL) and the combined filtrates were evaporated in vacuo. The resulting residue was purified by flash column chromatography (SiO₂, 80 g, 0-100% EtOAc in isohexane, gradient elution) to afford the title compound as a colourless oil (0.98 g, 92% pure by ¹H NMR, 77%); R$^r$ 1.63 min (Method 1a); m/z 289 (M+H)⁺ (ES⁺). This material was used in subsequent steps without additional purification.

Methyl 5-ethyl-2-(7-oxa-2-azaspiro[3.5]nonan-2-yl)nicotinate

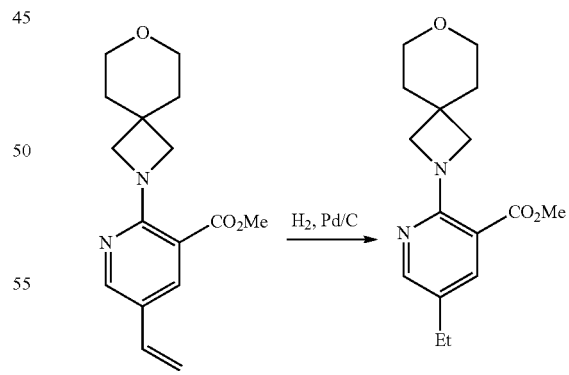

A solution of methyl 2-(7-oxa-2-azaspiro[3.5]nonan-2-yl)-5-vinylnicotinate (975 mg, 3.38 mmol) in EtOAc (20 mL) was passed through a Thales H-cube (1.0 mL min⁻¹, 25° C., 55 mm 10% Pd/C Cat-Cart, full hydrogen mode). The volatiles were removed in vacuo to afford the title compound as a colourless oil (927 mg, 94%); R$^r$ 1.32 min (Method 1a); m/z 291 (M+H)⁺ (ES⁺); ¹H NMR δ: 1.13 (3H, t), 1.67 (4H, br t), 2.51 (assume 2H, assume q obscured by solvent), 3.52 (4H, br t), 3.68 (4H, s), 3.80 (3H, s), 7.76 (1H, d), 8.16 (1H, d).

5-Ethyl-2-(7-oxa-2-azaspiro[3.5]nonan-2-yl)nicotinic Acid

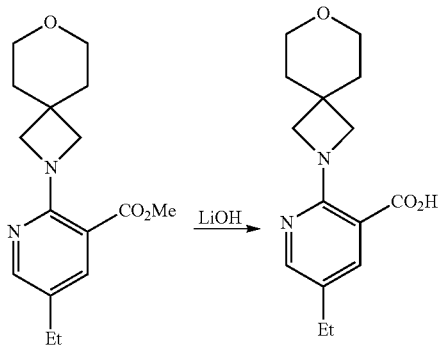

To a solution of methyl 5-ethyl-2-(7-oxa-2-azaspiro[3.5]nonan-2-yl)nicotinate (186 mg, 0.64 mmol) in THF:MeOH:water (1:1:1, 3.9 mL) was added lithium hydroxide (30 mg, 1.28 mmol). The reaction mixture was heated to 50° C. for 16 hr and was then cooled to RT. The volatiles were removed in vacuo and the remaining aq solution was diluted with water and acidified to pH 2 by the addition of 1 M aq HCl. The mixture was extracted with EtOAc (3×50 mL) and the combined organic extracts were dried and evaporated in vacuo to afforded the title compound as a yellow gum (166 mg, 83% pure by HPLC, 94% yield); $R^r$ 0.78 min (Method 1a); m/z 277 (M+H)$^+$ (ES$^+$). This material was used in subsequent steps without additional purification.

Methyl 2-(7-oxa-2-azaspiro[3.5]nonan-2-yl)-5-((triisopropylsilyl)ethynyl)nicotinate

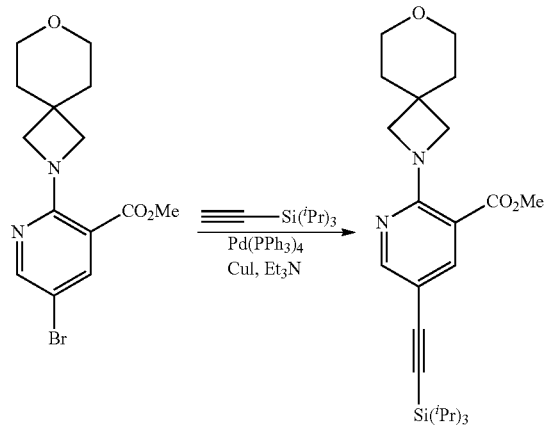

To a solution of methyl 5-bromo-2-(7-oxa-2-azaspiro[3.5]nonan-2-yl)nicotinate (100 mg, 0.29 mmol) in DMF (1.0 mL), which had been degassed with nitrogen for 10 min, was added tetrakis(triphenylphosphine)palladium(0) (35 mg, 0.03 mmol), copper(I) iodide (11 mg, 0.06 mmol), triethylamine (84 µL, 0.6 mmol) and ethynyltriisopropylsilane (369 µL, 0.3 mmol). The resulting mixture was flushed with nitrogen for 5 min, heated at 50° C. for 4 hr and was then cooled to RT and partitioned between water (10 mL) and EtOAc (25 mL). The organic layer was separated and retained and the aq phase was extracted with EtOAc (25 mL). The combined organic extracts were washed with water (10 mL) and with brine (10 mL), and then dried and evaporated in vacuo. The residue was purified by flash column chromatography (SiO$_2$, 12 g, 0-50% EtOAc in isohexane, gradient elution) to afford the title compound as a brown oil (117 mg, 88%); $R^r$ 3.35 min (Method 1a); m/z 443 (M+H)$^+$ (ES$^+$); $^1$H NMR δ: 1.08 (21H, over-lapping d and m), 1.68 (4H, br t), 3.52 (4H, br t), 3.77 (4H, s), 3.80 (3H, s), 7.89 (1H, d), 8.34 (1H, d).

2-(7-oxa-2-azaspiro[3.5]nonan-2-yl)-5-((triisopropylsilyl)ethynyl)nicotinic Acid

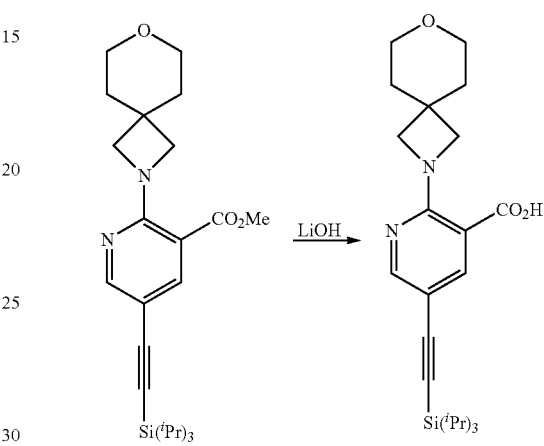

To a solution of methyl 2-(7-oxa-2-azaspiro[3.5]nonan-2-yl-5-((triisopropylsilyl)ethynyl) nicotinate (148 mg, 0.33 mmol) in a mixture of THF, MeOH and water (1:1:1, 2.1 mL) was added lithium hydroxide (10 mg, 0.40 mmol). The reaction mixture was heated to 50° C. for 3 hr and then cooled to RT. The volatiles were removed in vacuo and the remaining aq solution was acidified to pH 2 by the addition of 1 M hydrochloric acid. The mixture was extracted with a mixture of DCM and MeOH (9:1) and the organic extracts were dried and evaporated in vacuo to afforded the title compound as a brown gum (138 mg, 93% pure by $^1$H NMR, 97%); $R^r$ 3.21 min (Method 1a); m/z 429 (M+H)$^+$ (ES$^+$). This material was used in subsequent steps without additional purification.

Methyl 5-cyclopropyl-2-(7-oxa-2-azaspiro[3.5]nonan-2-yl)nicotinate

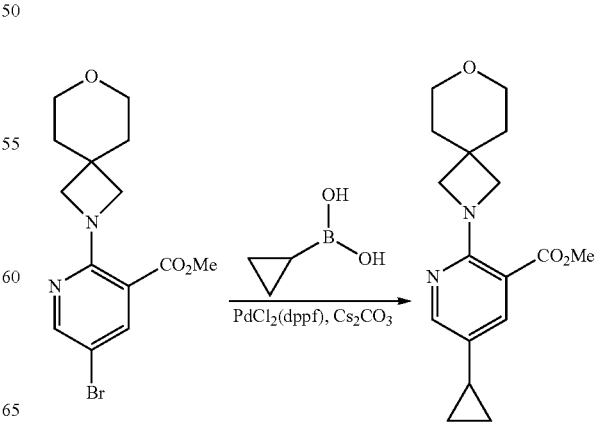

A mixture of methyl 5-bromo-2-(7-oxa-2-azaspiro[3.5]nonan-2-yl)nicotinate (1.50 g, 4.40 mmol), cyclopropylboronic acid (0.77 g, 9.00 mmol), cesium carbonate (3.23 g, 9.90 mmol) and [1,1'-bis(diphenylphosphino)ferrocene]dichloropalladium(II) (0.33 g, 0.45 mmol) was suspended in water (7.5 mL) and 1, 4-dioxane (15.0 mL) and was degassed with nitrogen for 10 min. The reaction mixture was heated at 100° C. for 6 hr and was then cooled and partitioned between EtOAc (100 mL) and water (100 mL). The organic layer was separated and was washed with brine (100 mL) and then dried and evaporated in vacuo. The crude residue was purified by flash column chromatography (SiO$_2$, 40 g, 0-100% EtOAc in isohexane, gradient elution) to afford the title compound, as a colourless oil (1.17 g, 91% pure by $^1$H NMR, 86%); R$^t$ 1.44 min (Method 1a); m/z 303 (M+H)$^+$ (ES$^+$). This material was used in subsequent steps without additional purification.

5-Cyclopropyl-2-(7-oxa-2-azaspiro[3.5]nonan-2-yl) nicotinic Acid

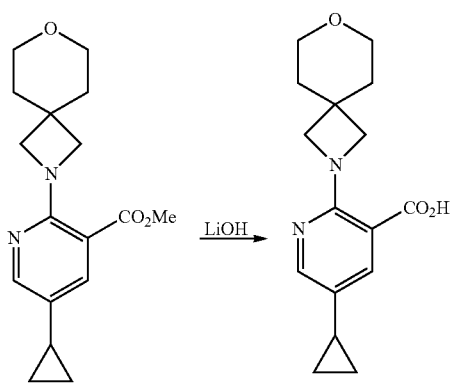 [SMILES: COC(=O)c1cc(C2CC2)cnc1N1CC2(CCOCC2)C1 ; "LiOH" ; O=C(O)c1cc(C2CC2)cnc1N1CC2(CCOCC2)C1]

To a solution of methyl 5-cyclopropyl-2-(7-oxa-2-azaspiro[3.5]nonan-2-yl)nicotinate (1.17 g, 3.87 mmol) in a mixture of THF, MeOH and water (2:1:1, 32 mL) was added lithium hydroxide (190 mg, 7.74 mmol). The reaction mixture was heated to 50° C. for 6 hr and was then cooled to RT. The volatiles were removed in vacuo and the remaining aq solution was acidified to pH 4 by the addition of 1 M hydrochloric acid. The mixture was extracted with EtOAc (3×100 mL) and the combined organic extracts were dried and evaporated in vacuo to afforded the title compound as a white foam (910 mg, 95% pure by $^1$H NMR, 82% yield); R$^t$ 0.92 min (Method 1a); m/z 289 (M+H)$^+$ (ES$^+$).

Benzyl 5-oxo-2,3,4,5-tetrahydro-1H-benzo[b]azepine-1-carboxylate

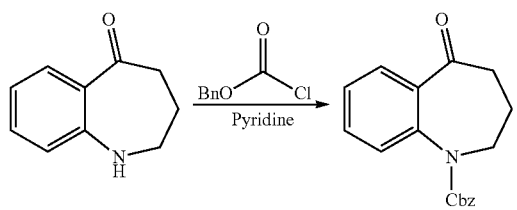

To a solution of 3,4-dihydro-1H-benzo[b]azepin-5(2H)-one (25.0 g, 155 mmol) in a mixture of DCM (258 mL) and pyridine (25.0 mL) at 0° C. was added dropwise benzyl chloroformate (38.0 mL, 264 mmol). The resulting mixture was warmed to RT for 18 hr and then water (150 mL) was added. After 15 min the biphasic mixture was separated and the organic layer was washed with 1 M aq HCl (150 mL) and with brine (150 mL), and then dried and concentrated in vacuo to give the title compound as a yellow oil (54.3 g, 85% pure by HPLC, containing unreacted benzyl chloroformate); R$^t$2.21 min (Method 1a); m/z 296 (M+H)$^+$ (ES$^+$). This material was used in the subsequent step without additional purification.

Benzyl 5-chloro-4-formyl-2,3-dihydro-1H-benzo[b] azepine-1-carboxylate

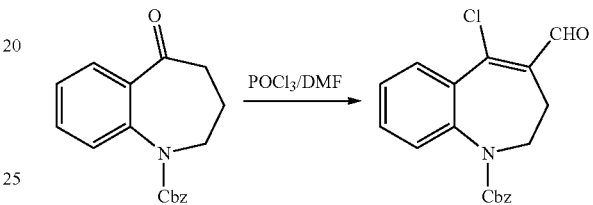

To neat DMF (330 mL) at 0° C. was added dropwise neat phosphoryl trichloride (20.5 mL, 221 mmol) and after 5 min at 0° C. the mixture was treated with a solution of benzyl 5-oxo-2,3,4,5-tetrahydro-1H-benzo[b]azepine-1-carboxylate (54.3 g, 184 mmol) in DMF (110 mL) via a cannula. The resulting yellow solution was stirred at 0° C. for 15 min, then allowed to attain RT for 30 min and afterwards was heated at 80° C. for 3 hr. The reaction mixture was cooled to RT for 16 hr and was then partitioned between EtOAc (700 mL) and sat aq NaOAc (800 mL). The aq layer was separated and was washed with EtOAc (400 mL). The combined organic extracts were washed with brine (2×800 mL), and then dried and concentrated in vacuo to give the title compound as a brown oil (69.9 g, 78% pure by HPLC); R$^t$ 2.47 min (Method 1a); m/z 342 (M+H)$^+$ (ES$^+$). This material was used in the subsequent step without additional purification.

6-Benzyl 2-ethyl 4,5-dihydro-6H-benzo[b]thieno[2,3-d]azepine-2,6-dicarboxylate

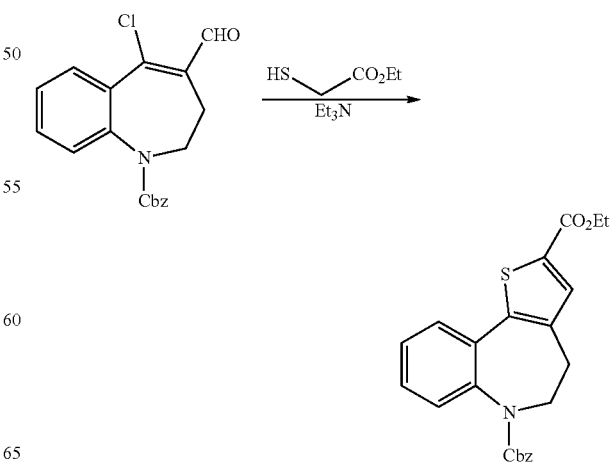

To a solution of benzyl 5-chloro-4-formyl-2,3-dihydro-1H-benzo[b]azepine-1-carboxylate (69.9 g, 205 mmol) in pyridine (432 mL) at RT was added ethyl 2-mercaptoacetate (45.0 mL, 409 mmol) followed by triethylamine (185 mL). The mixture was heated at 70° C. for 1 hr and at 115° C. for 3.5 hr and was allowed to cool to RT and left to stand at this temp for 60 hr. A white precipitate formed that was removed by filtration and was washed with acetonitrile (200 mL). The combined filtrates were concentrated in vacuo, during which process excess pyridine was removed as an azeotrope by adding aliquots of acetonitrile (500 mL) and DCM (500 mL). The resulting residue was taken up in DCM (400 mL) and was washed with 1 M aq HCl (300 mL). The aq layer was separated and was back extracted with DCM (100 mL). The combined organic extracts were washed with brine (400 mL) and then dried and evaporated in vacuo to give an oily residue. On standing for 16 hr a solid formed which was triturated with hexane (100 mL) and collected by filtration. The resulting cake was washed with acetonitrile (100 mL) and with MeOH (100 mL) and then air dried to afford the title compound as a cream coloured solid (24.5 g, 39% yield over 3 steps); $R^t$ 2.84 min (Method 1a); m/z 408 (M+H)$^+$ (ES$^+$).

Ethyl 5,6-dihydro-4H-benzo[b]thieno[2,3-d]azepine-2-carboxylate hydrochloride

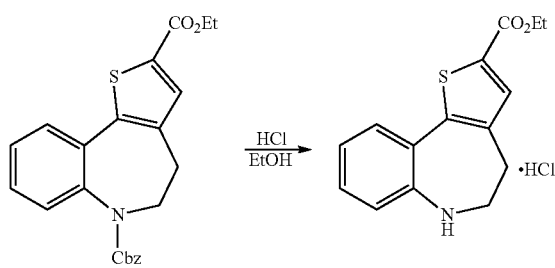 [SMILES: "EtOH" ; CCOC(=O)c1cc2c(s1)-c1ccccc1N(C(=O)OCc1ccccc1)CC2 ; Cl ; CCOC(=O)c1cc2c(s1)-c1ccccc1NCC2 ; Cl]

A mixture of 6-benzyl 2-ethyl 4,5-dihydro-6H-benzo[b]thieno[2,3-d]azepine-2,6-dicarboxylate (20.0 g, 49.1 mmol) in ethanolic HCl (393 mL, 1.25 M, 491 mmol) was heated at reflux for 15 hr and was then concentrated in vacuo. An additional aliquot of ethanolic HCl (393 mL, 1.25 M, 491 mmol) was added and the mixture was heated for a second time at reflux for 48 hr. The same process was repeated for a third time and after 18 hr at reflux the volatiles were removed in vacuo and the resulting solid was triturated with ether (300 mL). The product was collected by filtration and was dried to afford the title compound as a white solid (12.5 g, 79% yield); $R^t$ 2.47 min (Method 1a); m/z 274 (M+H)$^+$ (ES$^+$); $^1$H NMR δ: 1.29 (3H, t), 3.01 (2H, apparent t), 3.32 (2H, apparent t), 4.28 (2H, q), 6.73 (1H, apparent t), 6.86 (1H, d), 7.08 (1H, qd), 7.56 (1H, dd), 7.58 (1H, s).

Ethyl 6-(4-nitrobenzoyl)-5,6-dihydro-4H-benzo[b]thieno[2,3-d]azepine-2-carboxylate Method 1: Via Acylation of the Benzothienoazepine Precursor

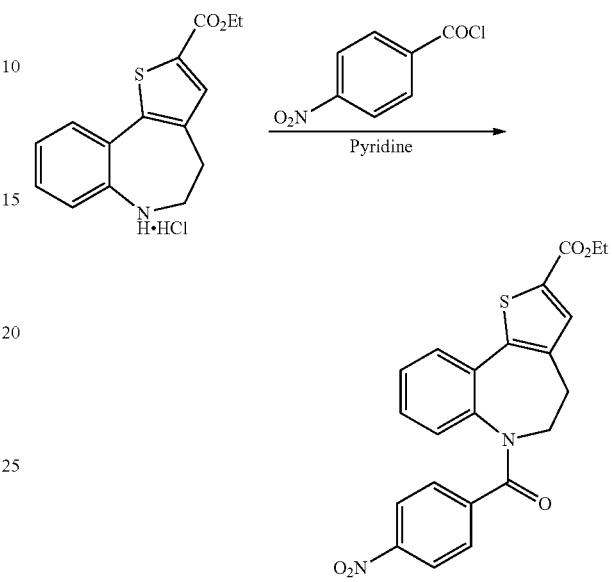

A solution of 4-nitrobenzoyl chloride (539 mg, 2.91 mmol) in acetonitrile (5.0 mL) was added dropwise to a solution of ethyl 5,6-dihydro-4H-benzo[b]thieno[2,3-d]azepine-2-carboxylate hydrochloride (750 mg, 2.42 mmol) in pyridine (5.0 mL) at RT. After 18 hr at RT the resulting mixture was poured carefully into 1 M aq HCl (100 mL) and extracted with EtOAc (2×50 mL). The combined organic extracts were washed with sat aq NaHCO$_3$ (2×50 mL), and then dried and evaporated in vacuo. The crude solid thus obtained was purified by flash column chromatography (SiO$_2$, 12 g, 0-50% EtOAc in isohexane, gradient elution) to afford the title compound, as a colourless glass (987 mg, 95%); $R^t$ 2.58 min (Method 1a); m/z 423 (M+H)$^+$ (ES$^+$); $^1$H NMR (CDCl$_3$) δ: 1.42 (3H t), 3.13 (1H, dt), 3.31-3.38 (1H, m), 3.48-3.57 (1H, m), 4.41 (2H, q), 5.05-5.11 (1H, m), 6.70 (1H, d), 7.02 (1H, t), 7.24-7.27 (assume 3H, obscured by solvent), 7.71 (1H, s), 7.78 (1H, dd), 8.01 (2H, d).

Method 2 Via Acylation of the Benzoazepinone Precursor

1-(4-Nitrobenzoyl)-1,2,3,4-tetrahydro-5H-benzo[b]azepin-5-one

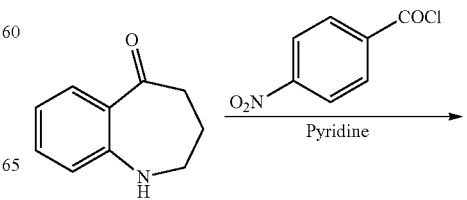

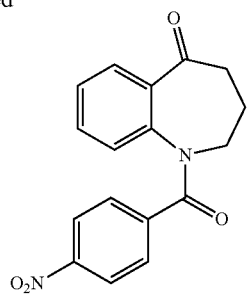

To a solution of 1,2,3,4-tetrahydro-benzo[b]azepin-5-one (25.0 g, 155 mmol) in pyridine (124 mL) at RT was added dropwise a solution of 4-nitrobenzoyl chloride (57.6 g, 310 mmol) in MeCN (124 mL). The resulting mixture was stirred at RT for 16 hr and was then quenched carefully with water (50 mL) and extracted with EtOAc (100 mL). The organic extracts were washed sequentially with sat aq NaHCO$_3$ (100 mL), sat aq NH$_4$Cl (2×100 mL), water (100 mL), brine (100 mL), and finally with 1 M aq HCl (2×100 mL), dried and the volatiles evaporated in vacuo. The crude solid thus obtained was slurried with MeOH (300 mL) and was collected by filtration and dried to afford the title compound as a light yellow solid (44.8 g, 93% pure by HPLC, 93%); R$^t$ 1.92 min (Method 1a); m/z 311 (M+H)$^+$ (ES$^+$). This material was used in the subsequent step without additional purification.

5-Chloro-1-(4-nitrobenzoyl)-2,3-dihydro-1H-benzo[b]azepine-4-carbaldehyde

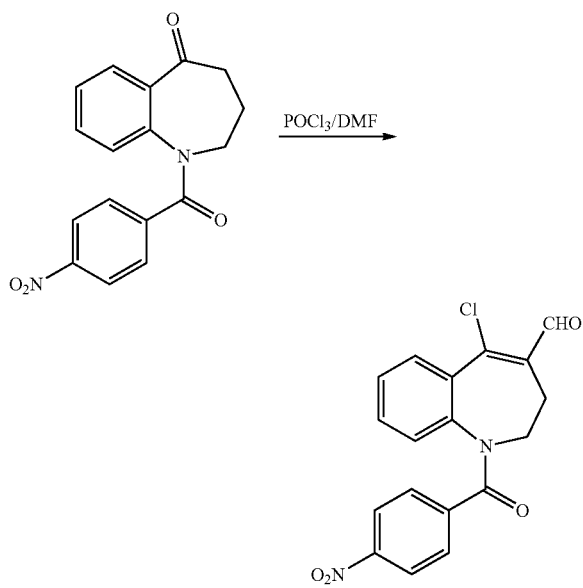

To neat DMF (236 mL) at 0° C. was added dropwise phosphoryl trichloride (15.8 mL, 170 mmol) and the resulting mixture treated with a solution of 1-(4-nitrobenzoyl)-1,2,3,4-tetrahydro-5H-benzo[b]azepin-5-one (44.8 g. 141 mmol) in DMF (141 mL) [the latter obtained by heating a suspension at 90° C. until full dissolution of the solid had occurred and the solution added whilst still hot] whilst maintaining the internal temp between 0-5° C. The reaction mixture was stirred at 0° C. for 15 min, then allowed to attain RT for 30 min and afterwards was heated at 80° C. for 72 hr. The resulting mixture was cooled to RT and was partitioned between EtOAc (500 mL) and sat aq NaOAc (500 mL). The aq layer was separated and was washed with EtOAc (2×500 mL). The combined organic extracts were washed with brine (8×300 mL), and then dried and evaporated in vacuo to give a brown solid. The crude product thus obtained was slurried with MeOH (300 mL) and was collected by filtration and dried to afford the title compound as a yellow solid (25.8 g, 88% pure by HPLC, 51%); R$^t$ 2.28 min (Method 1a); m/z 357 (M+H)$^+$ (ES$^+$). This material was used in the subsequent step without additional purification.

Ethyl 6-(4-nitrobenzoyl)-5,6-di hydro-4H-benzo[b]thieno[2,3-d]azepine-2-carboxylate

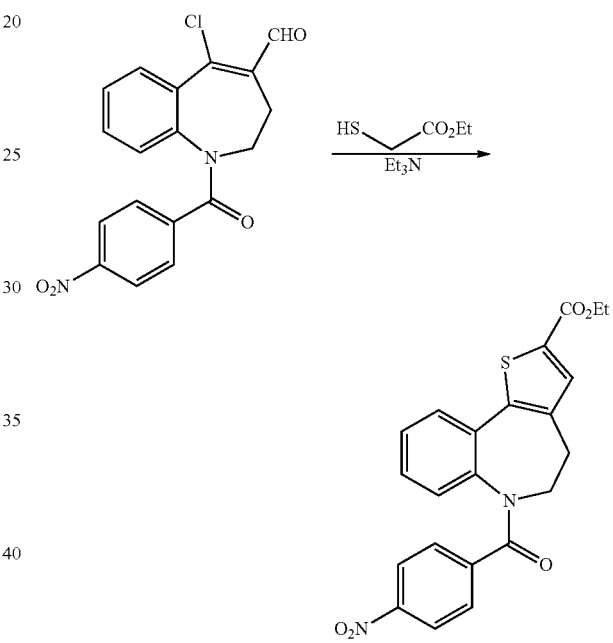

To a solution of 5-chloro-1-(4-nitrobenzoyl)-2,3-dihydro-1H-benzo[b]azepine-4-carbaldehyde (36.6 g, 89.0 mmol) in pyridine (260 mL) at RT was added ethyl 2-mercaptoacetate (18.6 mL, 170 mmol) followed by triethylamine (81.0 mL). The reaction mixture was heated at 70° C. for 1 hr, and at 118° C. for 2 hr and was then cooled to RT. The white precipitate that formed was removed by filtration and the filtrate concentrated in vacuo. The resulting residue was taken up in DCM (100 mL) and was washed with water (100 mL) and then with 1 M aq HCl (70 mL). The organic extracts were dried and evaporated in vacuo. The crude solid thus obtained was slurried with MeOH (150 mL), collected by filtration and dried to afford the title compound as a yellow solid (34.2 g, 84%); R$^t$ 2.65 min (Method 1a); m/z 423 (M+H)$^+$ (ES$^+$); $^1$H NMR δ: 1.32 (3H, t), 3.09-3.17 (1H, m), 3.28-3.41 (assume 2H, obscured by solvent), 4.33 (2H, q), 4.83-4.92 (1H, m), 6.96 (1H, br d), 7.10 (1H, td), 7.24 (2H, br d), 7.28 (1H, td), 7.78-7.81 (2H, over-lapping s and dd), 8.06 (2H, br d).

6-(4-Nitrobenzoyl)-5,6-dihydro-4H-benzo[b]thieno[2,3-d]azepine-2-carboxylic Acid

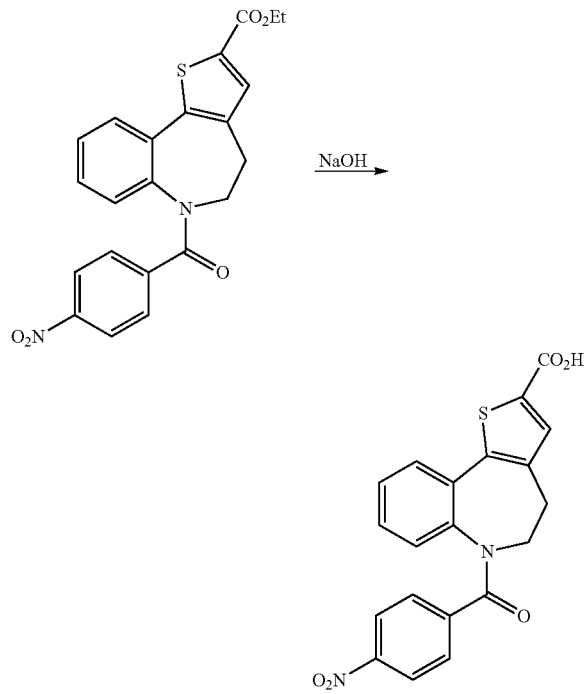

To a solution of ethyl 6-(4-nitrobenzoyl)-5,6-dihydro-4H-benzo[b]thieno[2,3-d]azepine-2-carboxylate (1.50 g, 3.55 mmol) in a mixture of THF:MeOH (1:1, 36 mL) was added 2 M aq NaOH (9.0 mL) and the mixture heated at 50° C. for 2 hr. After cooling to RT the mixture was partitioned between EtOAc (200 mL) and water (200 mL). The aq layer was separated and was acidified to pH 3 by the addition of 1 M aq HCl and then extracted with EtOAc (2×150 mL). Removal of the volatiles in vacuo afforded the title compound, as a yellow solid (1.44 g, 99% yield); $R^t$ 2.24 min (Method 1a); m/z 395 (M+H)$^+$ (ES$^+$); $^1$H NMR δ: 3.06-3.17 (1H, m), 3.27-3.40 (assume 2H, obscured by solvent), 4.83-4.92 (1H, m), 6.95 (1H, br d), 7.08 (1H, br t), 7.23-7.30 (3H, over-lapping br d and br t), 7.69 (1H, s), 7.78 (1H, dd), 8.06 (2H, br d), 13.33 (1H, br s).

(2-(1H-Benzo[d]imidazol-2-yl)-4,5-dihydro-6H-benzo[b]thieno[2,3-d]azepin-6-yl)(4-nitro phenyl)methanone

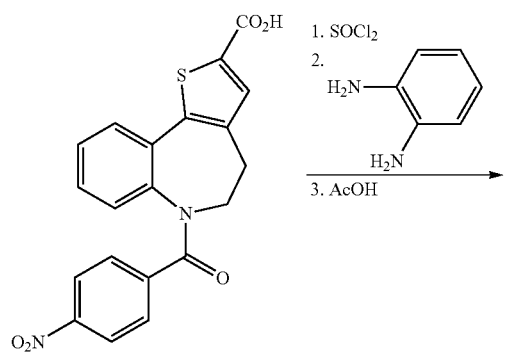

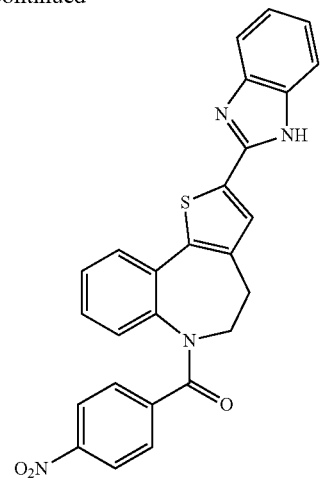

To a solution of 6-(4-nitrobenzoyl)-5,6-dihydro-4H-benzo[b]thieno[2,3-d]azepine-2-carboxylic acid (1.00 g, 2.54 mmol) in DCM (80 mL) at RT was added thionyl chloride (9.25 mL, 127 mmol). The reaction mixture was heated at reflux for 2 hr and was then cooled to RT and concentrated in vacuo. The residue was taken up into DCM (20 mL) and the resulting solution was treated with benzene-1,2-diamine (2.74 g, 25.4 mmol) and DIPEA (1.77 mL, 10.1 mmol). After 1 hr at RT water (20 mL) was added and the biphasic mixture was passed through a phase separator. The organic phase was collected, concentrated in vacuo and the resulting residue taken up into AcOH (20 mL) and heated at 125° C. for 1 hr. The mixture was cooled to RT and was concentrated in vacuo to afford a brown residue which was triturated with Et$_2$O (2×20 mL). The resulting solid was collected by filtration, washed with Et$_2$O (20 mL) and dried to afford the title compound, as a pale yellow solid (0.57 g, 90% pure by HPLC, 48%); $R^t$ 2.05 min (Method 1a); m/z 467 (M+H)$^+$ (ES$^+$). This material was used in the subsequent step without additional purification.

(2-(1H-Benzo[d]imidazol-2-yl)-4,5-dihydro-6H-benzo[b]thieno[2,3-d]azepin-6-yl)(4-aminophenyl)methanone

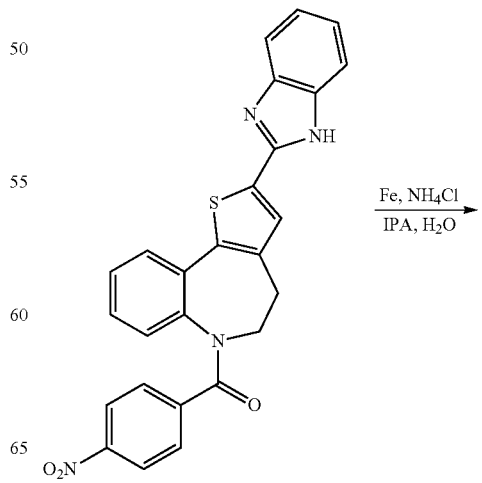

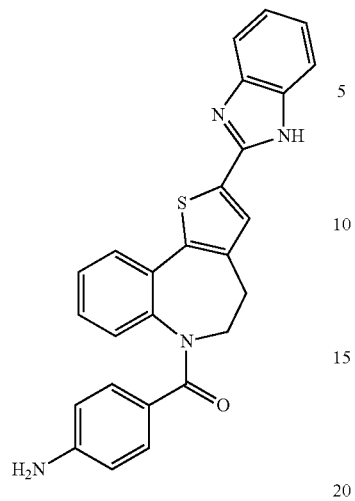

To a solution of (2-(1H-benzo[d]imidazol-2-yl)-4,5-dihydro-6H-benzo[b]thieno[2,3-d]azepin-6-yl)(4-nitrophenyl)methanone (1.00 g, 2.14 mmol) in IPA (10 mL) at RT was added sat aq NH₄Cl (1.0 mL) and iron powder (0.60 g, 10.7 mmol). The reaction mixture was heated at 80° C. for 2 hr, cooled to RT and was then filtered through a celite pad. The pad was washed with MeOH (2×10 mL) and the combined filtrates were concentrated in vacuo. The resulting residue was taken up into DCM (10 mL) and water (10 mL) and passed through a phase separator. The volatiles were evaporated in vacuo to afford the title compound as a pale yellow solid (0.73 g, 90% pure by HPLC, 78%); R$^t$ 1.69 min (Method 1a); m/z 437 (M+H)$^+$ (ES$^+$). This material was used in the subsequent step without additional purification.

N-(4-(2-(1H-Benzo[d]imidazol-2-yl)-5,6-dihydro-4H-benzo[b]thieno[2,3-d]azepine-6-carbonyl)phenyl)-2-chloro-6-methylnicotinamide

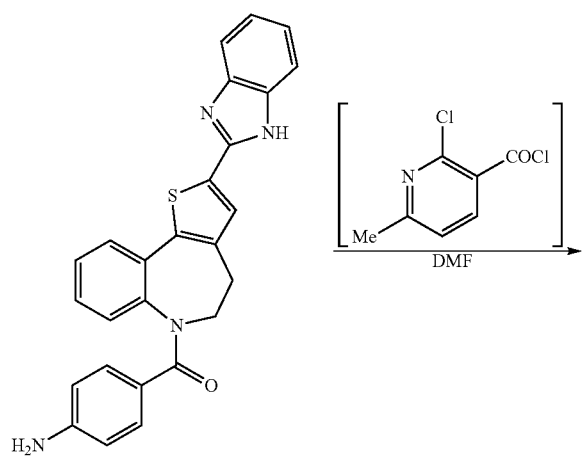

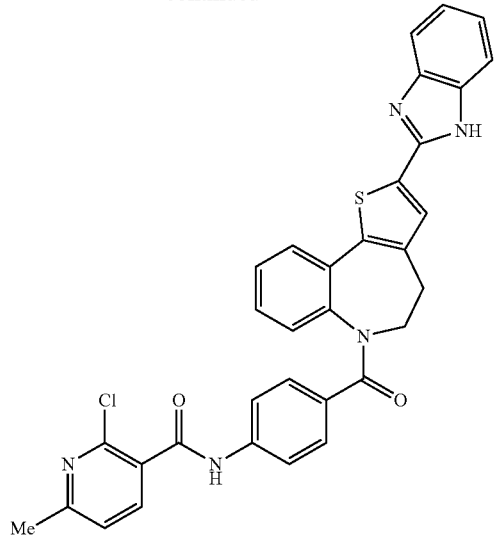

To DMF (5.0 mL) at RT was added neat oxalyl chloride (120 μL, 1.37 mmol) over 10 min and the mixture stirred for an additional 10 min. An aliquot (2.0 mL) of the resulting solution was added to 2-chloro-6-methylnicotinic acid (79 mg, 0.46 mmol) and the mixture was kept at RT for 30 min and was then treated with a solution of (2-(1H-benzo[d]imidazol-2-yl)-4,5-dihydro-6H-benzo[b]thieno[2,3-d]azepin-6-yl)(4-aminophenyl)methanone (100 mg, 0.23 mmol) in pyridine (1.0 mL). The reaction mixture was maintained at RT for 1 hr, quenched by the addition of sat aq NaHCO₃ (5.0 mL) and then partitioned between EtOAc (10 mL) and water (10 mL). The organic layer was separated and dried and was concentrated in vacuo to give the title compound as a pale yellow solid (130 mg, 90% pure by HPLC, 96%); R$^t$ 1.94 min (Method 1a); m/z 591 (M+H)$^+$ (ES$^+$). This material was used in the subsequent step without additional purification.

N-(4-(2-(1H-Benzo[d]imidazol-2-yl)-5,6-dihydro-4H-benzo[b]thieno[2,3-d]azepine-6-carbonyl)phenyl)-2-(7-oxa-2-azaspiro[3,5]nonan-2-yl)-5-((triisopropylsilyl)ethynyl) nicotinamide

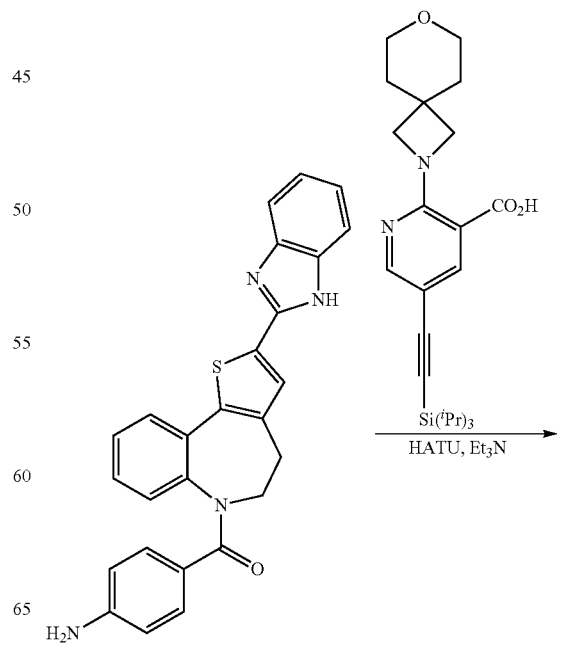

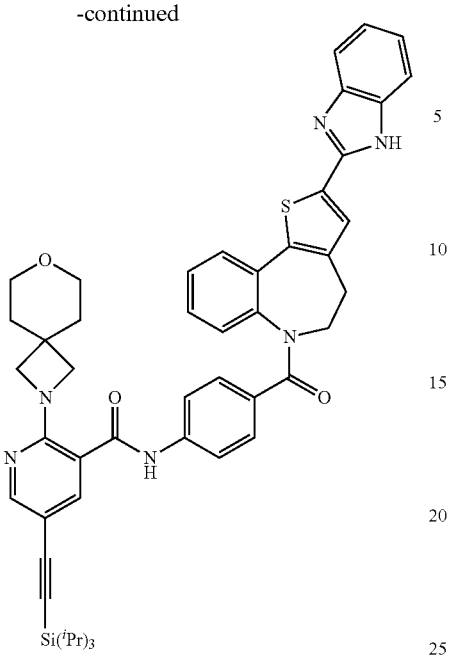

To a solution of (2-(1H-benzo[d]imidazol-2-yl)-4H-benzo[b]thieno[2,3-d]azepin-6(5H)-yl)(4-aminophenyl)methanone (109 mg, 0.25 mmol), 2-(7-oxa-2-azaspiro[3.5]nonan-2-yl)-5-((triisopropylsilyl)ethynyl)nicotinic acid (129 mg, 0.30 mmol) and HATU (143 mg, 0.38 mmol) in DMF (1.0 mL) was added triethylamine (71 μL, 0.50 mmol) and the resulting mixture stirred at 50° C. for 16 hr. Water (10 mL) was added and the resulting precipitate was collected by filtration. The solid was taken up into a mixture of DCM and MeOH (9:1), dried over a phase separator and then purified by flash column chromatography (SiO$_2$, 24 g, 0-10% MeOH in DCM, gradient elution) to afford the title compound as a light yellow solid (149 mg, 92% pure by HPLC, 70%); R$^t$ 3.16 min (Method 1a); m/z 424 (M+2H)$^{2+}$ (ES$^+$). This material was used in subsequent steps without additional purification.

Ethyl 6-(4-aminobenzoyl)-5,6-dihydro-4H-benzo[b]thieno[2,3-d]azepine-2-carboxylate Catalytic Reduction Method

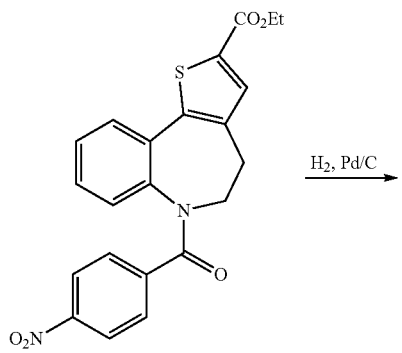

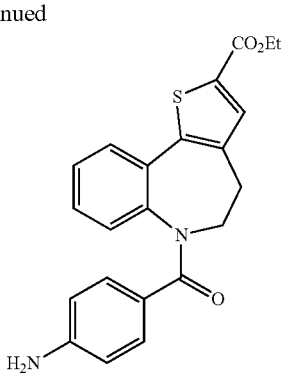

A solution of ethyl 6-(4-nitrobenzoyl)-5,6-dihydro-4H-benzo[b]thieno[2,3-d]azepine-2-carboxylate (1.00 g, 2.37 mmol) in a mixture of THF:EtOH (1:1, 100 mL) and 1 M aq HCl (2.00 mL) was passed through a Thales H-cube (1.0 mL·min$^{-1}$, 25° C., 55 mm 10% Pd/C Cat-Cart, full hydrogen mode). The volatiles were removed in vacuo to afford the title compound (0.98 g, ~100%); R$^t$ 2.28 min (Method 1a); m/z 393 (M+H)$^+$ (ES$^+$). This material was used in the subsequent step without additional purification.

Dissolving Metal Reduction Method

To a suspension of iron powder (5.29 g, 94.7 mmol) and ethyl 6-(4-nitrobenzoyl)-5,6-dihydro-4H-benzo[b]thieno[2,3-d]azepine-2-carboxylate (8.00 g, 18.9 mmol) in IPA (80 mL) was added saturated aq ammonium chloride (8.0 mL). The resulting mixture was stirred at 80° C. for 1 hr and was then filtered through celite. The celite pad was washed with MeOH (1.5 L) and combined filtrates were evaporated in vacuo. The resulting residue was triturated with water (400 mL) and with diethyl ether (400 mL) and was dried in vacuo to afford the title compound as a yellow solid (5.89 g, 88% pure by HPLC, 70%); R$^t$ 2.21 min (Method 1a); m/z 393 (M+H)$^+$ (ES$^+$). This material was used in subsequent steps without additional purification.

Ethyl 6-(4-2-chloronicotinamido)benzoyl)-5,6-dihydro-4H-benzo[b]thieno[2,3-d]azepine-2-carboxylate

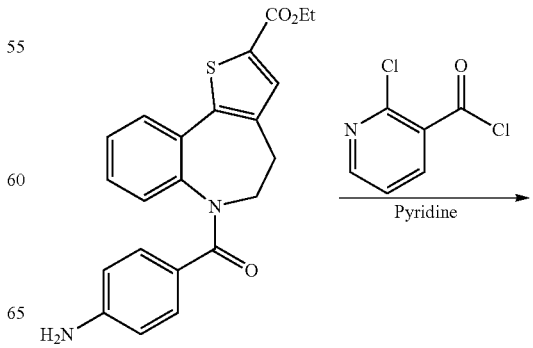

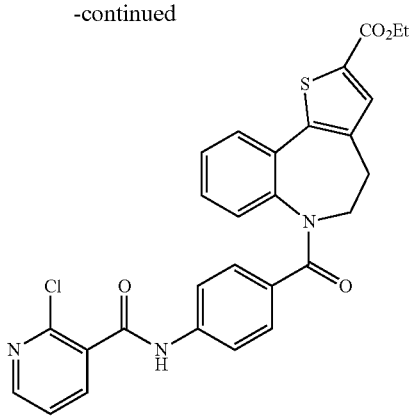

A solution of 2-chloronicotinoyl chloride (3.17 g, 18.0 mmol) in MeCN (80 mL) was added slowly to a solution of ethyl 6-(4-aminobenzoyl)-5,6-dihydro-4H-benzo[b]thieno[2,3-d]azepine-2-carboxylate (5.89 g, 15.0 mmol) in pyridine (80 mL) at RT. The resulting mixture was heated at 40° C. for 2 hr and was then cooled to RT and concentrated in vacuo. The residue was taken up into DCM:MeOH (9:1, 200 mL) and was washed with water (200 mL). The aq layer was separated and was extracted with DCM:MeOH (9:1, 2×100 mL) and the combined organic layers were dried and concentrated in vacuo to give the title compound as a yellow solid (7.62 g, 90% pure by HPLC, 91% yield); $R^t$ 2.36 min (Method 1a); m/z 532 (M+H)$^+$ (ES$^+$). This material was used in subsequent steps without additional purification.

Ethyl 6-(4-(2-chloro-5-methylnicotinamido)benzoyl)-5,6-dihydro-4H-benzo[b]thieno[2,3-d]azepine-2-carboxylate

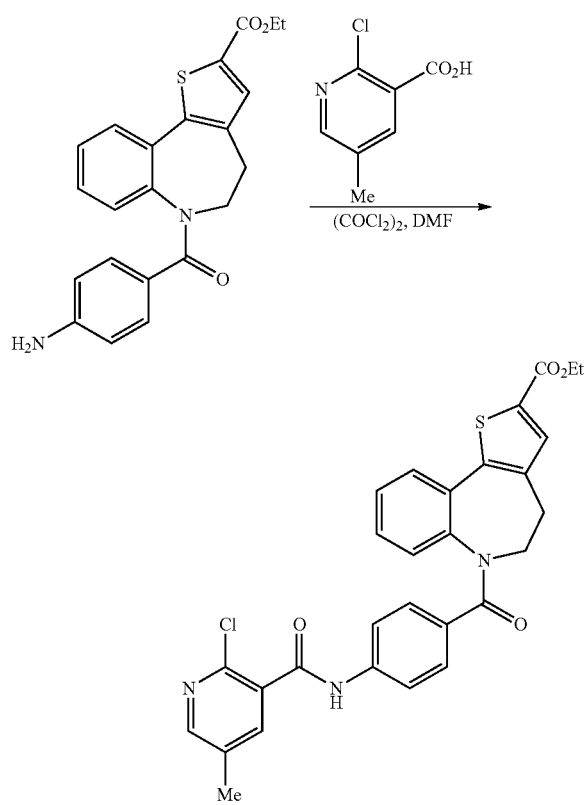

To a suspension of 2-chloro-5-methylnicotinic acid (2.49 g, 14.5 mmol) in DCM (50 mL) was added oxalyl chloride (4.24 mL, 48.4 mmol) and one drop of DMF. The resulting mixture was stirred at RT for 1 hr and the volatiles were evaporated in vacuo. The residue was taken up into DCM (25 mL) and added to a solution of ethyl 6-(4-aminobenzoyl)-5,6-dihydro-4H-benzo[b]thieno[2,3-d]azepine-2-carboxylate (3.80 g, 9.68 mmol) in pyridine (20 mL) at RT. The mixture was maintained at RT for 1 hr and then quenched by the addition of water (100 mL) and extracted with EtOAc (100 mL). The aq layer was separated and was washed with EtOAc (2×100 mL). The combined organic extracts were washed with water (100 mL) and evaporated in vacuo. The resulting solid was triturated with water (200 mL) and dried in vacuo. This process was repeated on the same scale to afford the title compound as a pale yellow solid (10.0 g, 89% pure by HPLC, 95%); $R^t$ 2.51 min (Method 1a); m/z 545/547 (M+H)$^+$ (ES$^+$). This material was used in subsequent steps without additional purification.

Ethyl 6-(4-(2-(7-oxa-2-azaspiro[3.5]nonan-2-yl)nicotinamido)benzoyl)-5,6-dihydro-4H-benzo[b]thieno[2,3-d]azepine-2-carboxylate

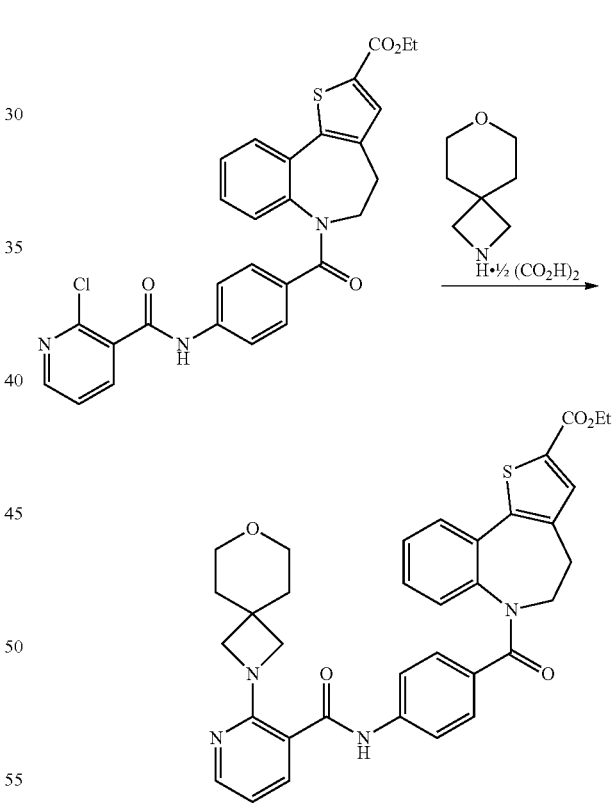

To a solution of ethyl 6-(4-2-chloronicotinamido)benzoyl)-5,6-dihydro-4H-benzo[b]thieno[2,3-d]azepine-2-carboxylate (7.62 g, 14.3 mmol) and 7-oxa-2-azaspiro[3.5]nonane hemi oxalate (4.67 g, 21.5 mmol) in NMP (36 mL) was added Et$_3$N (5.99 mL, 43.0 mmol). The reaction mixture was heated to 150° C. for 1 hr and was then cooled to RT. Water (100 mL) was added and the resulting precipitate was collected by vacuum filtration. The solid thus obtained was purified by flash column chromatography (SiO$_2$, 80 g, 0-10% MeCN in EtOAc, gradient elution) to afford the title

Ethyl 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylate

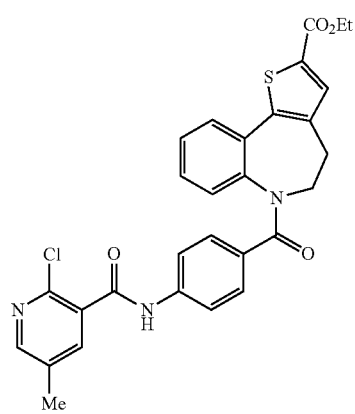

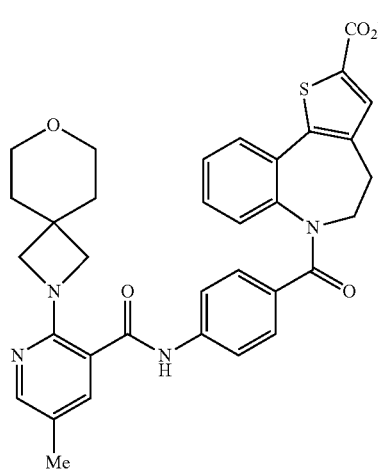

A suspension of ethyl 6-(4-(2-chloro-5-methylnicotinamido)benzoyl)-5,6-dihydro-4H-benzo[b]thieno[2,3-d]azepine-2-carboxylate (4.97 g, 9.10 mmol) and 7-oxa-2-azaspiro[3.5]nonane hemi oxalate (5.93 g, 27.3 mmol) in a mixture of NMP (23 mL) and Et$_3$N (7.61 mL, 54.6 mmol) was heated at 150° C. for 7.5 hr and then cooled to RT for 60 hr. Water (400 mL) was added and the resulting precipitate was collected by filtration. The solid was purified by flash column chromatography (SiO$_2$, 120 g, 0-30% THF in DCM, gradient elution) to afford the title compound as a pale yellow solid (3.72 g, 64%); R$^t$ 1.94 min (Method 1a); m/z 637 (M+H)$^+$ (ES$^+$); $^1$H NMR δ: 1.32 (3H, t), 1.62 (4H, br t), 2.17 (3H, s), 3.06-3.35 (assume 3H, obscured by solvent), 3.45 (4H, br t), 3.60 (4H, s), 4.32 (2H, q), 4.81-4.97 (1H, br), 6.88 (1H, br d), 6.99 (2H, br d), 7.14 (1H, br t), 7.29 (1H, td), 7.45-7.54 (3H, over-lapping m), 7.78 (1H, s), 7.81 (1H, dd), 8.04 (1H, dd), 10.36 (1H, s).

compound as a pale yellow solid (6.23 g, 63% yield); R$^t$ 1.93 min (Method 1a); m/z 623 (M+H)$^+$ (ES$^+$).

6-(4-(2-(7-Oxa-2-azaspiro[3.5]nonan-2-yl)nicotinamido)benzoyl)-5,6-dihydro-4H-benzo[b]thieno[2,3-d]azepine-2-carboxylic Acid

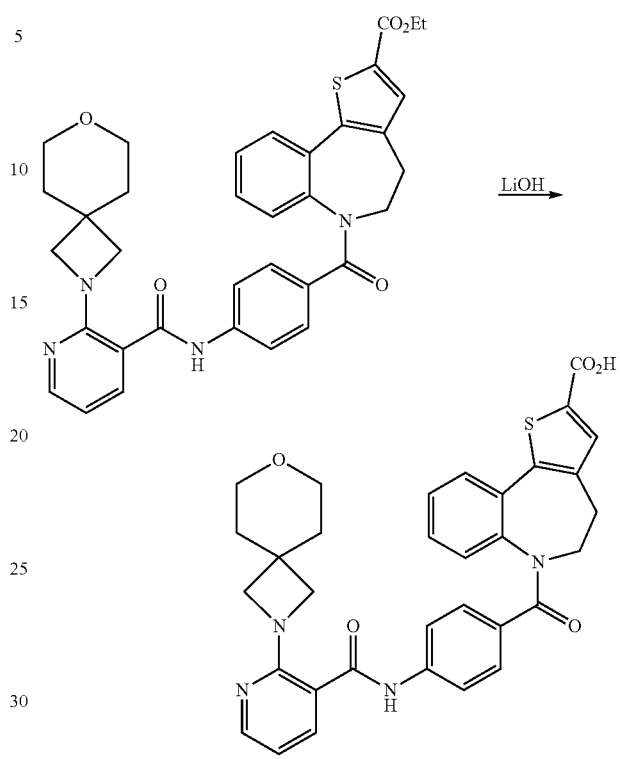

To a solution ethyl 6-(4-(2-(7-oxa-2-azaspiro[3.5]nonan-2-yl)nicotinamido)benzoyl)-5,6-dihydro-4H-benzo[b]thieno[2,3-d]azepine-2-carboxylate (4.35 g, 6.99 mmol) in THF:MeOH (1:1, 60 mL) was added a solution of lithium hydroxide (0.84 g, 34.9 mmol) in water (60 mL). The reaction mixture was heated to 50° C. for 1 hr and was then cooled to RT. The volatiles were removed in vacuo and the remaining aqueous solution was neutralised by the addition of 1 M aq HCl. The resulting solid was collected by vacuum filtration and dried in vacuo to afforded the title compound as an off-white solid (3.90 g, 92% yield); R$^t$ 1.63 min (Method 1a); m/z 595 (M+H)$^+$ (ES$^+$).

6-(4-(5-Methyl-2-(7-oxa-2-azaspiro[3.5]nonan-2-yl)nicotinamido)benzoyl)-5,6-dihydro-4H-benzo[b]thieno[2,3-d]azepine-2-carboxylic Acid

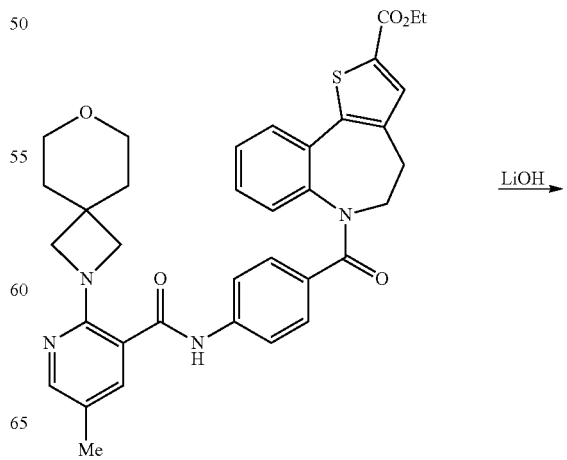

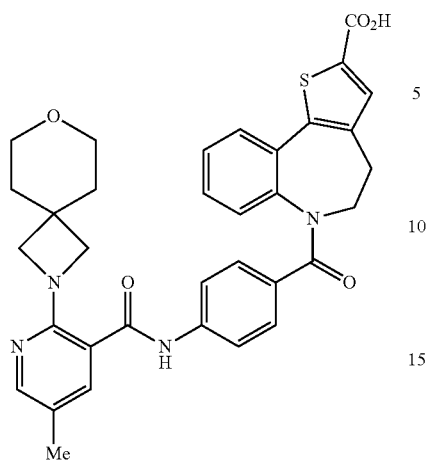

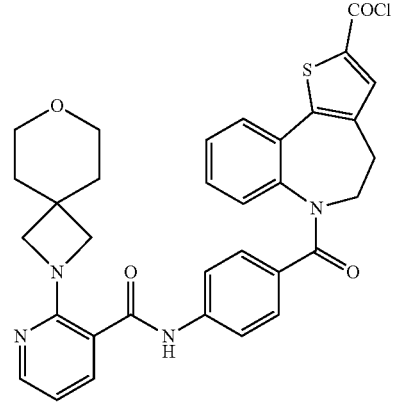

A solution of ethyl 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylate (3.72 g, 5.84 mmol) in a mixture of THF and MeOH (1:1, 40 mL) was treated with a solution of lithium hydroxide (0.70 g, 29.2 mmol) in water (40 mL) and the mixture heated to 50° C. for 1 hr and then cooled to RT. The volatiles were removed in vacuo and the remaining aq solution was diluted with water and sonicated until the resulting precipitate dissolved. The mixture was neutralised by the addition of 1 M hydrochloric acid and the resulting solid was collected by filtration and dried in vacuo to afford the title compound as an off-white solid (3.27 g, 92% yield); R$^r$ 1.64 min (Method 1a); m/z 609 (M+H)$^+$ (ES$^+$); $^1$H NMR δ: 1.62 (4H, br t), 2.16 (3H, s), 3.00-3.51 (assume 8H, obscured by solvent), 3.60 (4H, s), 4.82-4.96 (1H, br), 6.86 (1H, br d), 6.99 (2H, br d), 7.11 (1H, br t), 7.28 (1H, td), 7.46-7.54 (3H, over-lapping m), 7.62 (1H, s), 7.78 (1H, dd), 8.03 (1H, dd), 10.38 (1H, s).

6-(4-(2-(7-Oxa-2-azaspiro[3.5]nonan-2-yl)nicotinamido)benzoyl)-5,6-dihydro-4H-benzo[b]thieno[2,3-d]azepine-2-carbonyl Chloride

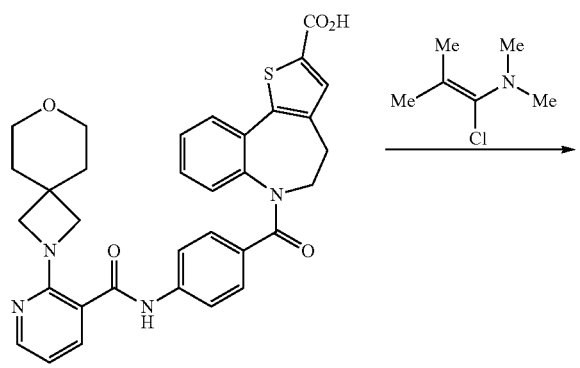

To a solution of 6-(4-(2-(7-oxa-2-azaspiro[3.5]nonan-2-yl)nicotinamido)benzoyl)-5,6-dihydro-4H-benzo[b]thieno[2,3-d]azepine-2-carboxylic acid (100 mg, 0.17 mmol) in DCM (10 mL) was added 1-chloro-N,N,2-trimethylprop-1-en-1-amine (45 µL, 0.34 mmol). The reaction mixture was stirred at RT for 30 min and was then concentrated in vacuo. The resulting residue was taken up into DCM (10 mL) to afford a stock solution of the title compound (16.80 mM). This material was used in subsequent steps without additional purification.

Ethyl 6-(2-fluoro-4-nitrobenzoyl)-5,6-dihydro-4H-benzo[b]thieno[2,3-d]azepine-2-carboxylate

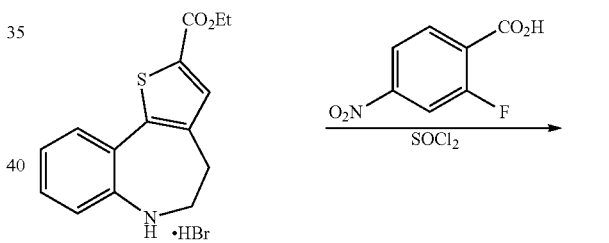

To a suspension of 2-fluoro-4-nitrobenzoic acid (1.00 g, 5.40 mmol) in DCM (30 mL) at RT was added thionyl chloride (2.87 mL, 39.3 mmol) and the resulting mixture was heated at reflux for 2 hr. The volatiles were evaporated in vacuo and the resulting residue was taken up into acetonitrile (20 mL) and was added dropwise at RT to a solution of ethyl 5,6-dihydro-4H-benzo[b]thieno[2,3-d]azepine-2-carboxylate hydrobromide (1.74 g, 4.91 mmol) in pyridine (20 mL). The mixture was stirred at RT for 4 hr and at 50° C. for 1 hr and was evaporated in vacuo. The residue was taken up into EtOAc (200 mL) and was washed sequentially with 1 M aq HCl (100 mL), sat aq NaHCO₃ (100 mL) and water (100 mL). The organic extracts were dried and evaporated in vacuo to afford the title compound as a brown gum (1.91 g, 95% pure by HPLC, 88%); R$^t$ 2.64 min (Method 1a); m/z 441 (M+H)⁺ (ES⁺). This material was used in the subsequent step without additional purification.

Ethyl 6-(4-amino-2-fluorobenzoyl)-5,6-dihydro-4H-benzo[b]thieno[2,3-d]azepine-2-carboxylate

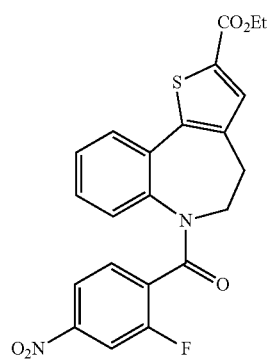

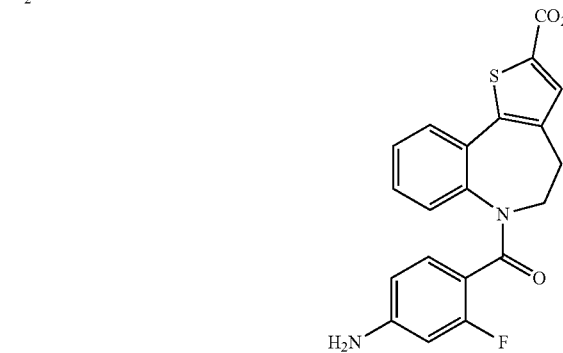

To a solution of ethyl 6-(2-fluoro-4-nitrobenzoyl)-5,6-dihydro-4H-benzo[b]thieno[2,3-d]azepine-2-carboxylate (4.55 g, 10.3 mmol) in a mixture of EtOH:water (2:1, 309 mL) at RT was added iron powder (2.88 g, 51.7 mmol) and ammonium chloride (5.53 g, 103 mmol). The resulting mixture was stirred at reflux for 2 hr, then cooled to RT and filtered through a celite pad. The pad was washed sequentially with MeOH (200 mL), DCM (100 mL) and with EtOAc (200 mL) and the combined organic filtrates were evaporated in vacuo. Water (250 mL) was added to the residue and the resulting solid was collected by filtration, washed with water (200 mL) and dried to afford the title compound (3.87 g, 89% yield); R$^t$ 2.29 min (Method 1a); m/z 411 (M+H)⁺ (ES⁺). This material was used in the subsequent step without additional purification.

Ethyl 6-(4-(2-chloro-6-methylnicotinamido)-2-fluorobenzoyl)-5,6-dihydro-4H-benzo[b]thieno[2,3-d]azepine-2-carboxylate

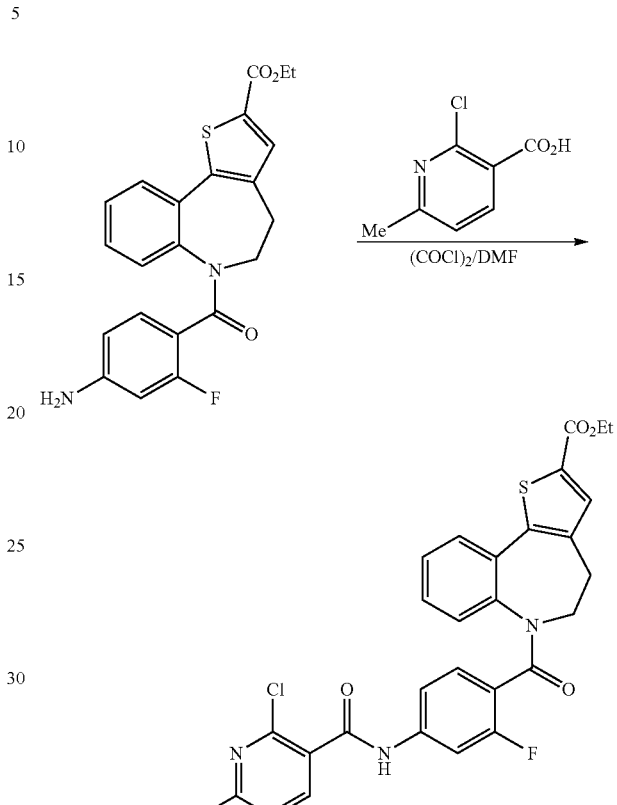

To neat DMF (40 mL) at RT was added neat oxalyl chloride (1.01 mL, 11.5 mmol) over 10 min and 10 min afterwards the resulting mixture was added to 2-chloro-6-methylnicotinic acid (0.92 g, 5.36 mmol). After an additional 10 min a solution of ethyl 6-(4-amino-2-fluoro benzoyl)-5,6-dihydro-4H-benzo[b]thieno[2,3-d]azepine-2-carboxylate (1.10 g, 2.68 mmol) in pyridine (13 mL) was added dropwise over 2 min at RT. The reaction mixture was stirred for 30 min, quenched by the addition of sat aq NaHCO₃ (10 mL) and then partitioned between EtOAc (10 mL) and water (10 mL). The organic layer was separated and dried and evaporated in vacuo. The solid thus obtained was purified by flash column chromatography (SiO₂, 12 g, 0-50% EtOAc in isohexane, gradient elution) to afford the title compound as an off-white solid (1.39 g, 88% yield); R$^t$ 2.49 min (Method 1 b); m/z 564 (M+H)⁺ (ES⁺); ¹H NMR δ: 1.32 (3H, t), 2.50 (assume 3H, obscured by solvent), 3.10 (1H, dt), 3.21-3.39 (assume 2H, obscured by solvent), 4.32 (2H, q), 4.81-4.86 (1H, m), 6.95 (1H, br d), 7.14 (1H, td), 7.20-7.40 (5H, over-lapping m), 7.76-7.78 (2H, over-lapping m), 7.94 (1H, d), 10.78 (1H, s).

Ethyl 6-(4-(2-(7-oxa-2-azaspiro[3.5]nonan-2-yl)-6-methylnicotinamido)-2-fluorobenzoyl)-5,6-dihydro-4H-benzo[b]thieno[2,3-d]azepine-2-carboxylate

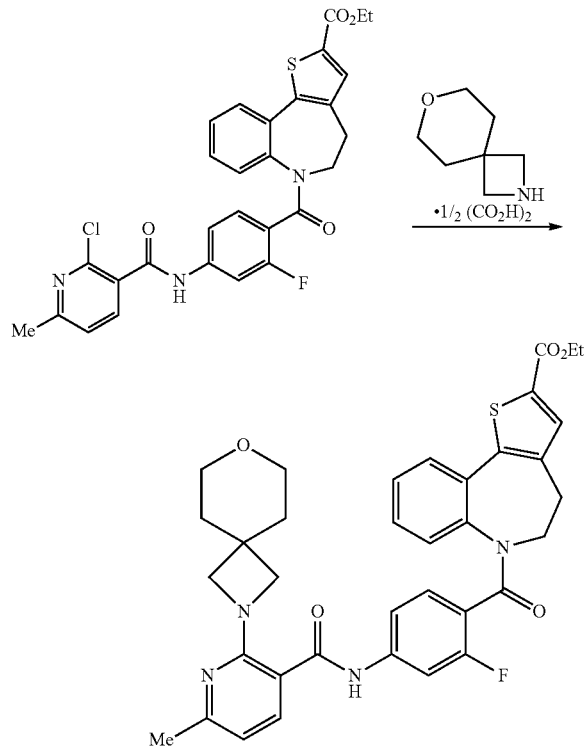

To a solution of ethyl 6-(4-(2-chloro-6-methylnicotinamido)-2-fluorobenzoyl)-5,6-dihydro-4H-benzo[b]thieno[2,3-d]azepine-2-carboxylate (669 mg, 1.19 mmol) and 7-oxa-2-azaspiro[3.5]nonane hemioxalate (773 mg, 3.56 mmol) in NMP (6.0 mL) was added Et₃N (0.99 mL, 7.12 mmol). The reaction mixture was heated to 130° C. for 1 hr and was then cooled to RT and treated with water (50 mL). The resulting precipitate was collected by vacuum filtration, washed with water (50 mL) and the solid then taken up into a mixture of DCM:MeOH (9:1). The volatiles were evaporated in vacuo to afford the title compound, (826 mg, 91% pure by HPLC, containing residual NMP; R$^t$ 1.98 min (Method 1a); m/z 655 (M+H)$^+$ (ES$^+$). This material was used in the subsequent step without additional purification.

6-(4-(2-(7-Oxa-2-azaspiro[3.5]nonan-2-yl)-6-methylnicotinamido)-2-fluorobenzoyl)-5,6-dihydro-4H-benzo[b]thieno[2,3-d]azepine-2-carboxylic Acid

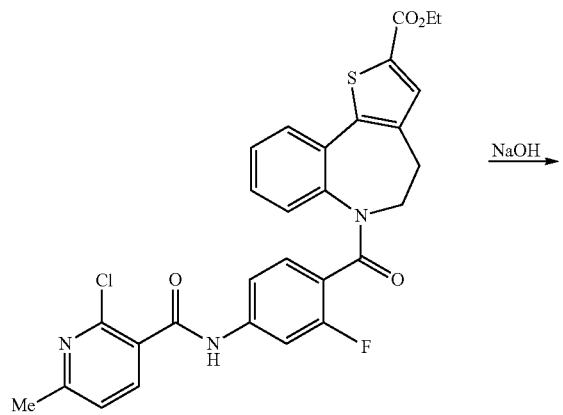

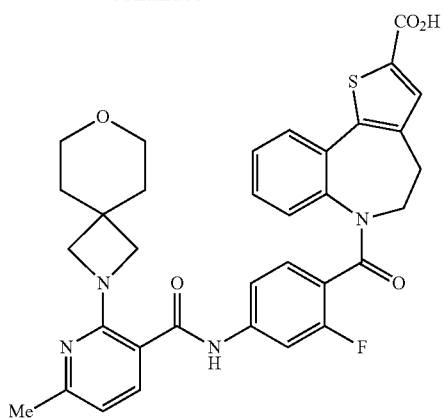

To a solution of ethyl 6-(4-(2-(7-oxa-2-azaspiro[3.5]nonan-2-yl)-6-methylnicotinamido)-2-fluorobenzoyl)-5,6-dihydro-4H-benzo[b]thieno[2,3-d]azepine-2-carboxylate (826 mg, 1.26 mmol) in a mixture of THF:MeOH (1:1, 12.6 mL) was added 2 M aq NaOH (6.3 mL) and the reaction mixture heated at 50° C. for 2 hr. After cooling to RT the mixture was acidified to pH 3 by the addition of 1 M aq HCl and extracted with a mixture of DCM:MeOH (9:1, 2×75 mL). The combined organic extracts were evaporated in vacuo to afforded the title compound as a off-white solid (775 mg, 90% pure by $^1$H NMR, 98%); R$^t$ 1.76 min (Method 1a); m/z 627 (M+H)$^+$ (ES$^+$). This material was used in the subsequent step without additional purification.

Preparation of Representative Compound Examples of the Invention

Example 1: N-(4-(2-(7-Methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide

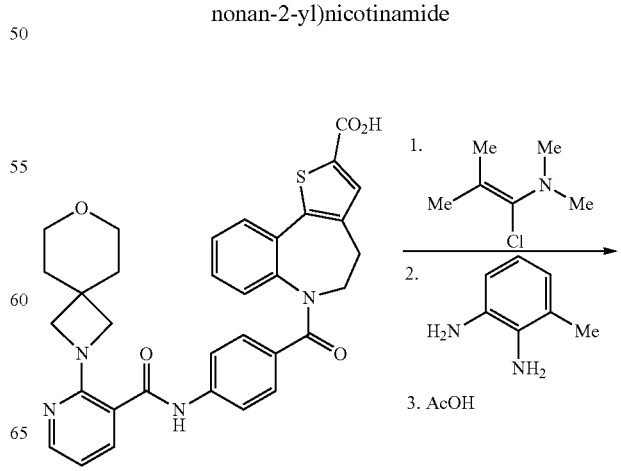

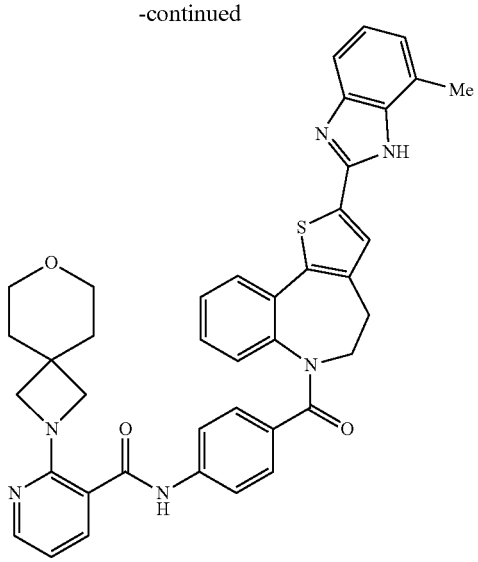

To a solution of 6-(4-(2-(7-oxa-2-azaspiro[3.5]nonan-2-yl)nicotinamido)benzoyl)-5,6-dihydro-4H-benzo[b]thieno[2,3-d]azepine-2-carboxylic acid (100 mg, 0.17 mmol) in DCM (2.0 mL) at RT was added 1-chloro-N,N,2-trimethyl-prop-1-en-1-amine (45 µL, 0.34 mmol). The reaction mixture was stirred at RT for 0.5 hr and was then concentrated in vacuo. The residue was taken up into MeCN (2.0 mL) and 3-methylbenzene-1,2-diamine (205 mg, 1.68 mmol) was added at RT. The resulting mixture was stirred at RT for 16 hr and was then diluted with DCM (2.0 mL) and water (2.0 mL) and was passed through a phase separator. The volatiles were evaporated in vacuo and the residue was taken up into AcOH (2.0 mL) and was heated at reflux for 1 hr. The mixture was concentrated in vacuo and the residue was purified by flash column chromatography (SiO$_2$, 80 g, 0-10% MeOH in DCM, gradient elution). The product so obtained was purified further by preparative HPLC (Method 1) to afford the title compound, Example 1, as a pale yellow solid (24 mg, 21%); R$^t$ 1.62 min (Method 1a); m/z 681 (M+H)$^+$ (ES$^+$); $^1$H NMR δ: 1.62 (4H, br t), 2.55 (1.5H, s), 2.57 (1.5H, s), 3.14-3.39 (3H, over-lapping m), 3.45 (4H, br t), 3.64 (4H, s), 4.95 (1H, m), 6.70 (1H, dd), 6.87 (1H, br d), 6.99-7.14 (5H, over-lapping m), 7.28-7.34 (1.5H, over-lapping m), 7.45 (0.5H, br d), 7.52 (2H, br d), 7.62 (1H, dd), 7.77 (0.5H, s), 7.86 (1H, dd), 7.92 (0.5H, s), 8.18 (1H, dd), (1H, 10.39 (1H, s), 12.77 (0.5H, s), 12.97 (0.5H, s).

Example 2: N-(4-(2-(1H-Benzo[d]imidazol-2-yl)-5,6-dihydro-4H-benzo[b]thieno[2,3-d]azepine-6-carbonyl)phenyl)-6-methyl-2-(7-oxa-2-azaspiro[3,5]nonan-2-yl)nicotinamide

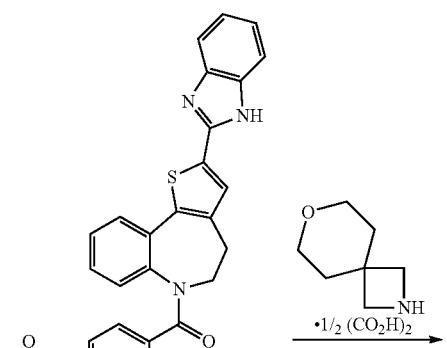

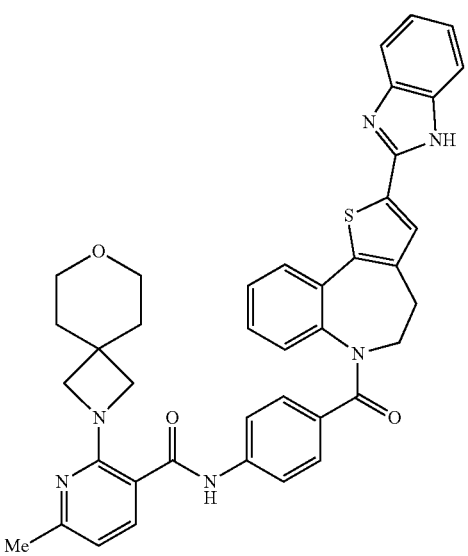

To a solution of N-(4-(2-(1H-benzo[d]imidazol-2-yl)-5,6-dihydro-4H-benzo[b]thieno[2,3-d]azepine-6-carbonyl)phenyl)-2-chloro-6-methylnicotinamide (130 mg, 0.22 mmol) and 7-oxa-2-azaspiro[3.5]nonane hemioxalate (144 mg, 0.66 mmol) in NMP (1.0 mL) was added triethylamine (184 µL, 1.32 mmol). The reaction mixture was heated to 150° C. for 1 hr and was cooled to RT and partitioned between EtOAc (10 mL) and water (10 mL). The organic layer was separated, dried by passing it through a phase separator and was then concentrated in vacuo to afford an orange oil. The residue was purified by preparative HPLC (Method 1) to afford the title compound, Example 2, as a pale yellow solid (53 mg, 34% yield); R$^t$ 1.56 min (Method 1a); m/z 341 (M+2H)$^{2+}$ (ES$^+$); $^1$H NMR δ: 1.62 (4H, br t), 2.32 (3H, s), 3.15-3.37 (assume 3H, obscured by solvent), 3.46 (4H, br t), 3.62 (4H, s), 4.91-5.01 (1H, b), 6.56 (1H, d), 6.87 (1H, broad d), 7.03 (2H, br d), 7.10 (1H, br t), 7.18-7.33 (3H, over-lapping m), 7.50-7.53 (4H, over-lapping m), 7.64 (1H, br d), 7.79 (1H, s), 7.83 (1H, dd), 10.26 (1H, s), 13.02 (1H, s).

Example 3: N-(4-(2-(7-Ethyl-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide

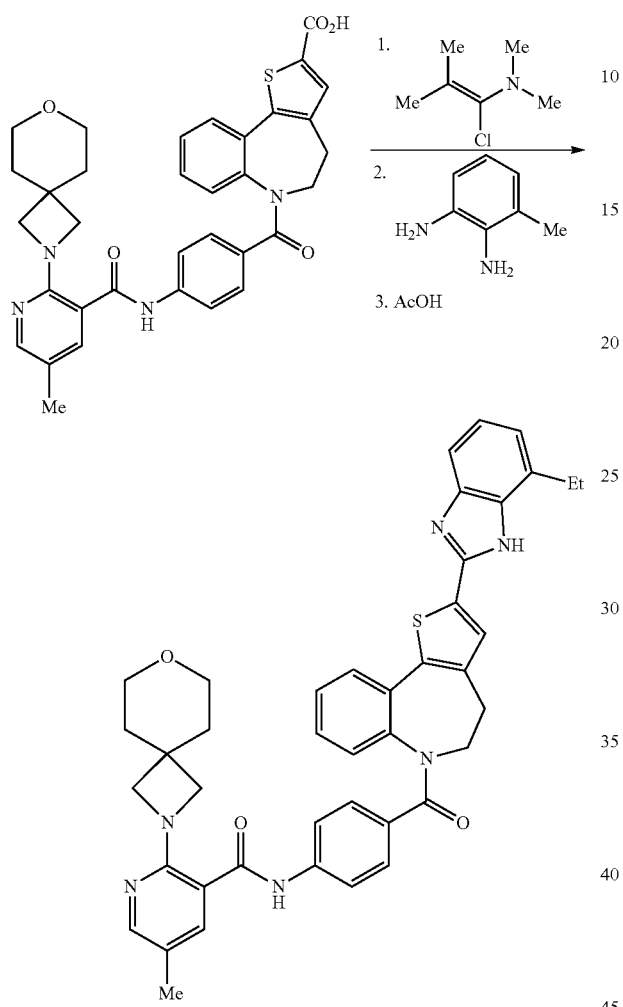

To a solution of 6-(4-(5-methyl-2-(7-oxa-2-azaspiro[3.5]nonan-2-yl)nicotinamido)benzoyl)-5,6-dihydro-4H-benzo[b]thieno[2,3-d]azepine-2-carboxylic acid (100 mg, 0.16 mmol) in DCM (5.0 mL) at RT was added 1-chloro-N,N,2-trimethylprop-1-en-1-amine (65 µL, 0.49 mmol). The reaction mixture was stirred at RT for 1 hr and was then concentrated in vacuo. The residue was taken up into DCM (2.0 mL) and added to a solution of 3-ethylbenzene-1,2-diamine (112 mg, 0.82 mmol) in pyridine (0.5 mL) at RT. The resulting mixture was stirred at RT for 18 hr and was then diluted with DCM (10 mL) and water (10 mL) and was passed through a phase separator. The aq phase was discarded and the volatiles were evaporated in vacuo. The residue was azetroped with toluene (5.0 mL), then taken up into AcOH (3.0 mL) and heated at reflux for 1 hr. The mixture was concentrated in vacuo, azetroped with acetonitrile (10 mL) and the residue purified by flash column chromatography (SiO$_2$, 4 g, 0-4% MeOH in DCM, gradient elution). The product so obtained was purified further by preparative HPLC (Method 1) to afford the title compound, Example 3, as a light yellow solid (35 mg, 30%); R$^t$ 1.80 min (Method 1a); m/z 709 (M+H)$^+$ (ES$^+$); $^1$H NMR δ: 1.29-1.35 (3H, m), 1.61 (4H, br t), 2.16 (3H, s), 2.89-3.03 (2H, m), 3.13-3.40 (assume 3H, obscured by solvent), 3.45 (4H, br t), 3.60 (4H, s), 4.89-5.04 (1H, br), 6.87 (1H, br d), 6.97-7.17 (5H, over-lapping m), 7.26-7.36 (1.5H, over-lapping m), 7.44-7.55 (3.5H, over-lapping m), 7.77 (0.5H, s), 7.84 (0.5H, dd), 7.88 (0.5H, dd), 7.94 (0.5H, s), 8.03 (1H, br d), 10.36 (1H, s), 12.74 (0.5H, s), 12.97 (0.5H, s).

Example 4: N-(4-(2-(1H-Benzo[d]imidazol-2-yl)-5,6-dihydro-4H-benzo[b]thieno[2,3-d]azepine-6-carbonyl)phenyl)-5-ethyl-2-(7-oxa-2-azaspiro[3.5]nonan-2-yl)nicotinamide

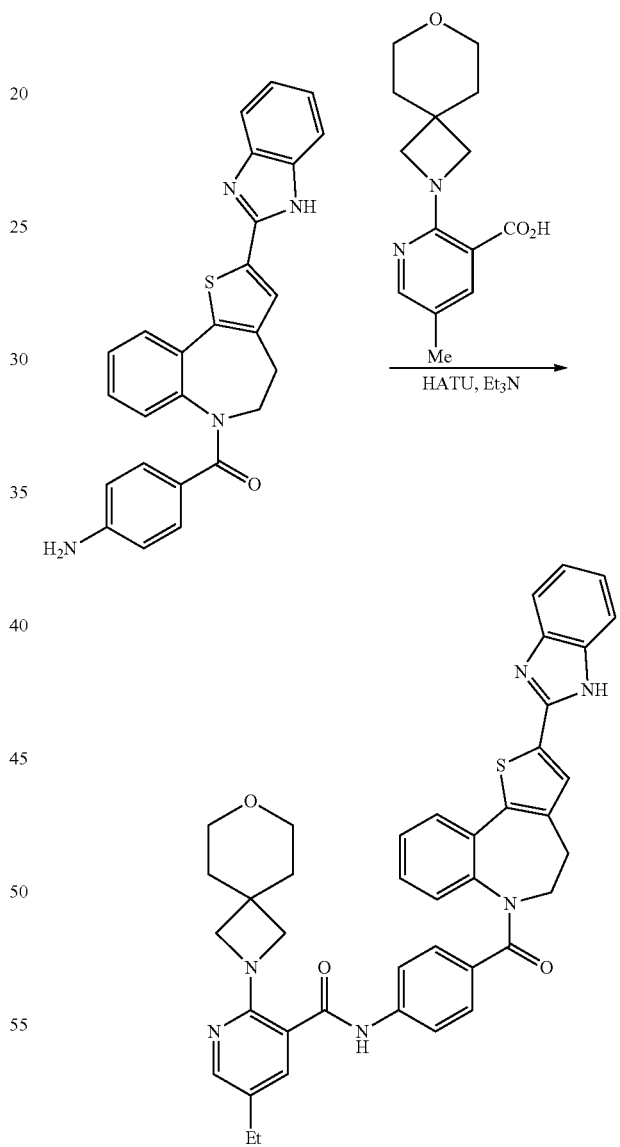

To a solution of (2-(1H-benzo[d]imidazol-2-yl)-4H-benzo[b]thieno[2,3-d]azepin-6(5H)-yl)(4-aminophenyl)methanone (87 mg, 0.2 mmol), 5-ethyl-2-(7-oxa-2-azaspiro[3.5]nonan-2-yl) nicotinic acid (66 mg, 0.2 mmol) and HATU (114 mg, 0.3 mmol) in DMF (0.8 mL) was added triethylamine (57 µL, 0.4 mmol) and the resulting mixture stirred at RT for 16 hr. Water (25 mL) was added and the resulting precipitate was collected by filtration. The solid was taken up into a mixture of DCM:MeOH (9:1), dried over a phase separator and then purified by flash column chromatography (SiO$_2$, 12 g, 10% MeOH in DCM, isocratic elution) to afford the title compound, Example 4, as a yellow solid (51 mg, 37%); R$^t$ 1.73 min (Method 1a); m/z 695 (M+H)$^+$ (ES$^+$); $^1$H NMR δ: 1.14 (3H, t), 1.62 (4H, br t), 2.50 (assume 2H, obscured by solvent), 3.14-3.39 (assume 3H, obscured by solvent), 3.45 (4H, br t), 3.63 (4H, s), 4.90-5.01 (1H, br), 6.87 (1H, br d), 7.04 (2H, br d), 7.10 (1H, br t), 7.21-7.25 (2H, m), 7.31 (1H, td), 7.47-7.63 (5H, over-lapping m), 7.80 (1H, s), 7.84 (1H, dd), 8.05 (1H, d), 10.39 (1H, s), 13.12 (1H, br).

Example 5: N-(4-(2-(1H-Benzo[d]imidazol-2-yl)-5, 6-dihydro-4H-benzo[b]thieno[2,3-d]azepine-6-carbonyl)phenyl)-5-ethynyl-2-(7-oxa-2-azaspiro[3,5]nonan-2-yl)nicotinamide To a solution of N-(4-(2-(1H-benzo[d]imidazol-2-yl)-5,6-dihydro-4H-benzo[b]thieno[2,3-d]azepine-6-carbonyl)phenyl)-2-(7-oxa-2-azaspiro[3,5]nonan-2-yl)-5-((triisopropylsilyl)ethynyl) nicotinamide (149 mg, 0.18 mmol) in THF (1.8 mL) was added a solution of TBAF in THF (1M, 216 μL, 0.22 mmol) and the resulting mixture stirred at RT for 2 hr. The solvent was evaporated in vacuo and the resulting residue taken up into MeOH and subject to SCX capture and release. The crude product so obtained was purified by flash column chromatography (SiO$_2$, 12 g, 0-10% MeOH in DCM, gradient elution) to afford the title compound, Example 5, as a white solid (61 mg, 49%); R$^t$ 1.98 min (Method 1a); m/z 346 (M+2H)$^{2+}$ (ES$^+$); $^1$H NMR δ: 1.63 (4H, br t), 3.14-3.39 (assume 3H, obscured by solvent), 3.45 (4H, br t), 3.69 (4H, s), 4.13 (1H, s), 4.90-5.02 (1H, br), 6.88 (1H, br d), 7.04 (2H, br d), 7.10 (1H, br t), 7.22 (2H, br d), 7.31 (1H, td), 7.46-7.68 (4H, over-lapping m), 7.71 (1H, d), 7.79 (1H, s), 7.84 (1H, dd), 8.28 (1H, d), 10.45 (1H, s), 13.04 (1H, s).

Example 6: N-(4-(2-(1H-Benzo[d]imidazol-2-yl)-5, 6-dihydro-4H-benzo[b]thieno[2,3-d]azepine-6-carbonyl)phenyl)-5-cyclopropyl-2-(7-oxa-2-azaspiro[3,5]nonan-2-yl)nicotinamide

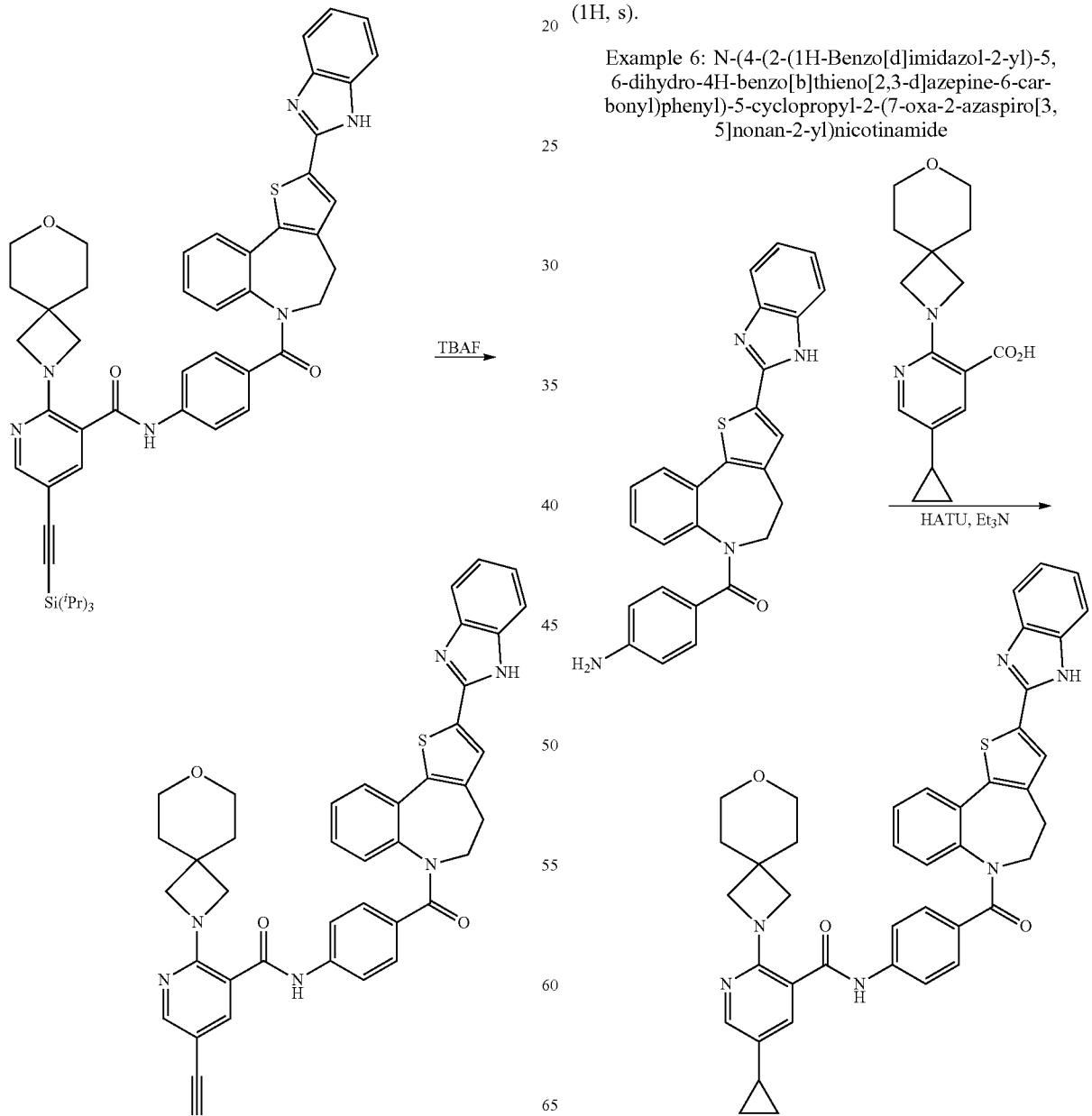

To a solution of (2-(1H-benzo[d]imidazol-2-yl)-4H-benzo[b]thieno[2,3-d]azepin-6(5H)-yl)(4-aminophenyl)methanone (87 mg, 0.20 mmol), 5-cyclopropyl-2-(7-oxa-2-azaspiro[3.5]nonan-2-yl)nicotinic acid (69 mg, 0.20 mmol) and HATU (114 mg, 0.30 mmol) in DMF (0.8 mL) was added triethylamine (57 μL, 0.40 mmol) and the resulting mixture stirred at 50° C. for 16 hr. Water (25 mL) was added and the resulting precipitate was collected by filtration. The solid was taken up into a mixture of DCM:MeOH (9:1), dried over a phase separator and then purified by flash column chromatography (SiO$_2$, 12 g, 0-10% MeOH in DCM, gradient elution) to afford the title compound, Example 6, as a light yellow solid (59 mg, 42%); R$^t$ 1.79 min (Method 1a); m/z 707 (M+H)$^+$ (ES$^+$); $^1$H NMR δ: 0.60-0.64 (2H, m), 0.83-0.88 (2H, m), 1.61 (4H, br t), 1.80-1.87 (1H, m), 3.14-3.26 (2H, m), 3.30-3.39 (assume 1H, obscured by solvent), 3.44 (4H, br t), 3.59 (4H, s), 4.90-5.00 (1H, br), 6.87 (1H, br d), 7.03 (2H, br d), 7.10 (1H, br t), 7.22 (2H, br d), 7.28-7.33 (2H, over-lapping m), 7.50-7.67 (4H, over-lapping m), 7.79 (1H, s), 7.84 (1H, dd), 8.03 (1H, d), 10.35 (1H, s), 13.06 (1H, s).

TABLE 2

Additional Compound Examples of the Invention
Structure, Example No., Name, Prep HPLC Method, Analytical and Spectral Data

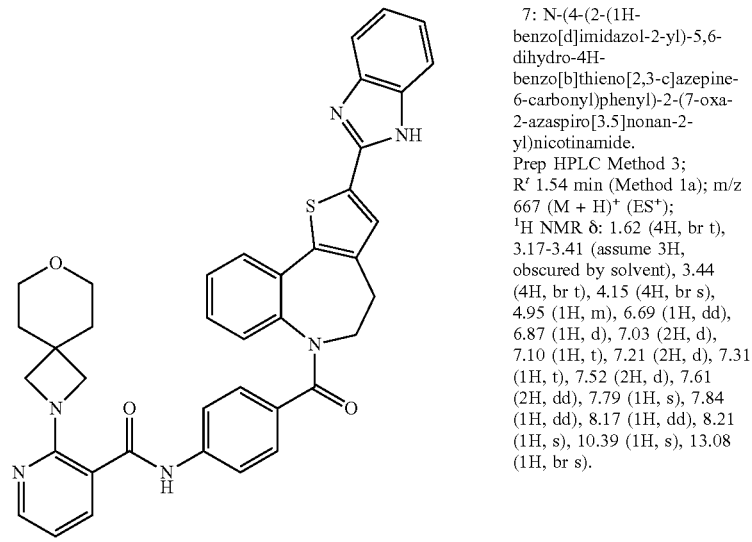

7: N-(4-(2-(1H-benzo[d]imidazol-2-yl)-5,6-dihydro-4H-benzo[b]thieno[2,3-c]azepine-6-carbonyl)phenyl)-2-(7-oxa-2-azaspiro[3.5]nonan-2-yl)nicotinamide.
Prep HPLC Method 3;
R$^t$ 1.54 min (Method 1a); m/z 667 (M + H)$^+$ (ES$^+$);
$^1$H NMR δ: 1.62 (4H, br t), 3.17-3.41 (assume 3H, obscured by solvent), 3.44 (4H, br t), 4.15 (4H, br s), 4.95 (1H, m), 6.69 (1H, dd), 6.87 (1H, d), 7.03 (2H, d), 7.10 (1H, t), 7.21 (2H, d), 7.31 (1H, t), 7.52 (2H, d), 7.61 (2H, dd), 7.79 (1H, s), 7.84 (1H, dd), 8.17 (1H, dd), 8.21 (1H, s), 10.39 (1H, s), 13.08 (1H, br s).

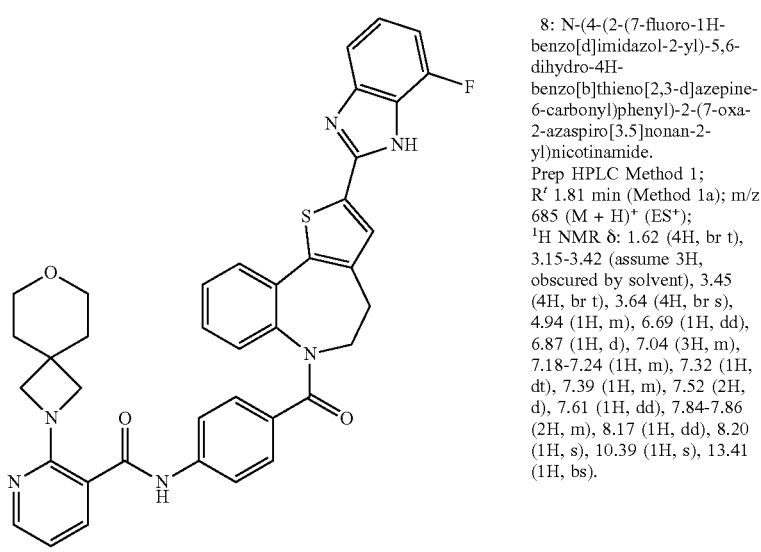

8: N-(4-(2-(7-fluoro-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide.
Prep HPLC Method 1;
R$^t$ 1.81 min (Method 1a); m/z 685 (M + H)$^+$ (ES$^+$);
$^1$H NMR δ: 1.62 (4H, br t), 3.15-3.42 (assume 3H, obscured by solvent), 3.45 (4H, br t), 3.64 (4H, br s), 4.94 (1H, m), 6.69 (1H, dd), 6.87 (1H, d), 7.04 (3H, m), 7.18-7.24 (1H, m), 7.32 (1H, dt), 7.39 (1H, m), 7.52 (2H, d), 7.61 (1H, dd), 7.84-7.86 (2H, m), 8.17 (1H, dd), 8.20 (1H, s), 10.39 (1H, s), 13.41 (1H, bs).

TABLE 2-continued

Additional Compound Examples of the Invention
Structure, Example No., Name, Prep HPLC Method, Analytical and Spectral Data

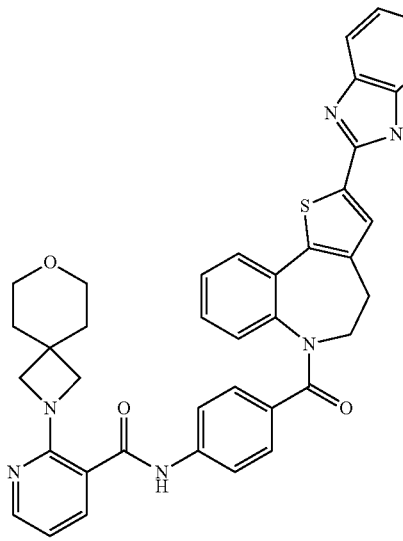

9: N-(4-(2-(7-chloro-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide.
Prep HPLC Method 2;
$R^t$ 1.93 min (Method 1a); m/z 702 (M + H)$^+$ (ES$^+$);
$^1$H NMR δ: 1.62 (4H, br t), 3.15-3.40 (assume 3H, obscured by solvent), 3.45 (4H, br t), 3.64 (4H, br s), 4.95 (1H, m), 6.69 (1H, dd), 6.88 (1H, d), 7.03 (2H, d), 7.11 (1H, t), 7.20-7.24 (1H, t), 7.28-7.33 (2H, m), 7.51-7.53 (3H, m), 7.61 (1H, dd), 7.87 (2H, d), 8.17 (1H, dd), 10.39 (1H, s), 13.37 (1H, br s).

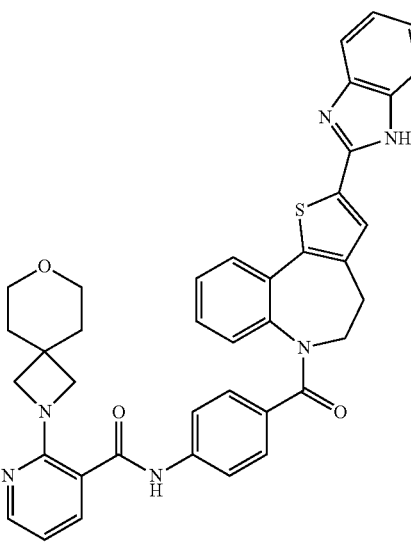

10: 2-(7-oxa-2-azaspiro[3.5]nonan-2-yl)-N-(4-(2-(7-(trifluoromethyl)-1H-benzo[d]imidazol-2-yl)-5,6-dihydro-4H-benzo[b]thieno[2,3-d]azepine-6-carbonyl)phenyl)nicotinamide.
Prep HPLC Method 2;
$R^t$ 2.08 min (Method 1a); m/z 735 (M + H)$^+$ (ES$^+$);
$^1$H NMR δ: 1.62 (4H, br t), 3.14-3.39 (3H, over-lapping m), 3.45 (4H, br t), 3.64 (4H, s), 4.96 (1H, m), 6.70 (1H, dd), 6.88 (1H, br d), 7.03 (2H, br d), 7.11 (1H, apparent t), 7.30 (1H, td), 7.38 (1H, t), 7.50-7.56 (3H, over-lapping m), 7.62 (1H, dd), 7.84-7.90 (3H, over-lapping m), 8.18 (1H, dd), 10.38 (1H, s), 13.51 (1H, br s).

TABLE 2-continued

Additional Compound Examples of the Invention
Structure, Example No., Name, Prep HPLC Method, Analytical and Spectral Data

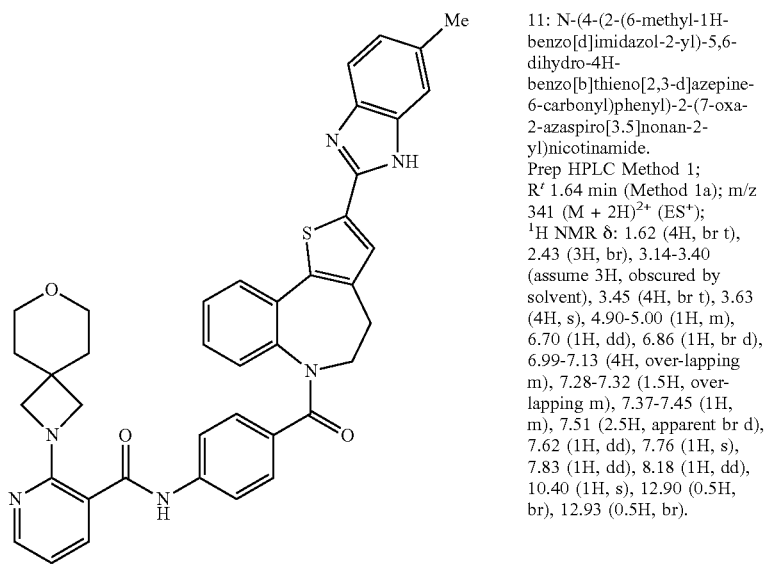

11: N-(4-(2-(6-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide.
Prep HPLC Method 1;
$R^t$ 1.64 min (Method 1a); m/z 341 (M + 2H)$^{2+}$ (ES$^+$);
$^1$H NMR δ: 1.62 (4H, br t), 2.43 (3H, br), 3.14-3.40 (assume 3H, obscured by solvent), 3.45 (4H, br t), 3.63 (4H, s), 4.90-5.00 (1H, m), 6.70 (1H, dd), 6.86 (1H, br d), 6.99-7.13 (4H, over-lapping m), 7.28-7.32 (1.5H, overlapping m), 7.37-7.45 (1H, m), 7.51 (2.5H, apparent br d), 7.62 (1H, dd), 7.76 (1H, s), 7.83 (1H, dd), 8.18 (1H, dd), 10.40 (1H, s), 12.90 (0.5H, br), 12.93 (0.5H, br).

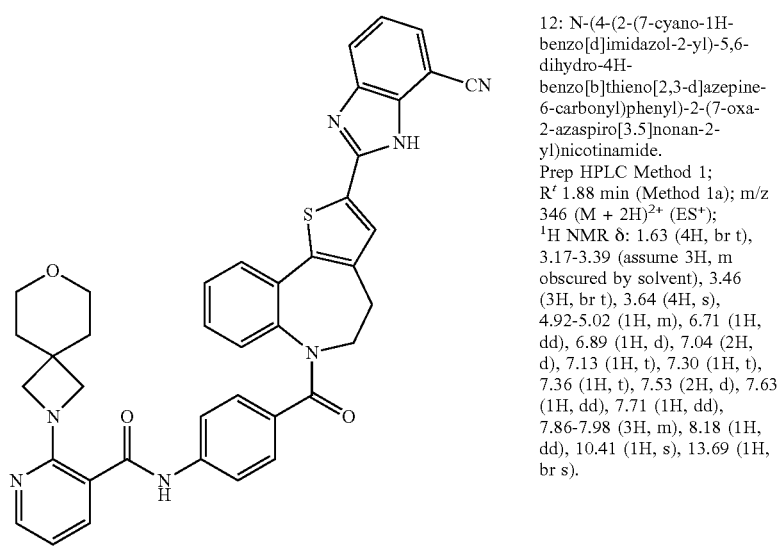

12: N-(4-(2-(7-cyano-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide.
Prep HPLC Method 1;
$R^t$ 1.88 min (Method 1a); m/z 346 (M + 2H)$^{2+}$ (ES$^+$);
$^1$H NMR δ: 1.63 (4H, br t), 3.17-3.39 (assume 3H, m obscured by solvent), 3.46 (3H, br t), 3.64 (4H, s), 4.92-5.02 (1H, m), 6.71 (1H, dd), 6.89 (1H, d), 7.04 (2H, d), 7.13 (1H, t), 7.30 (1H, t), 7.36 (1H, t), 7.53 (2H, d), 7.63 (1H, dd), 7.71 (1H, dd), 7.86-7.98 (3H, m), 8.18 (1H, dd), 10.41 (1H, s), 13.69 (1H, br s).

TABLE 2-continued

Additional Compound Examples of the Invention
Structure, Example No., Name, Prep HPLC Method, Analytical and Spectral Data

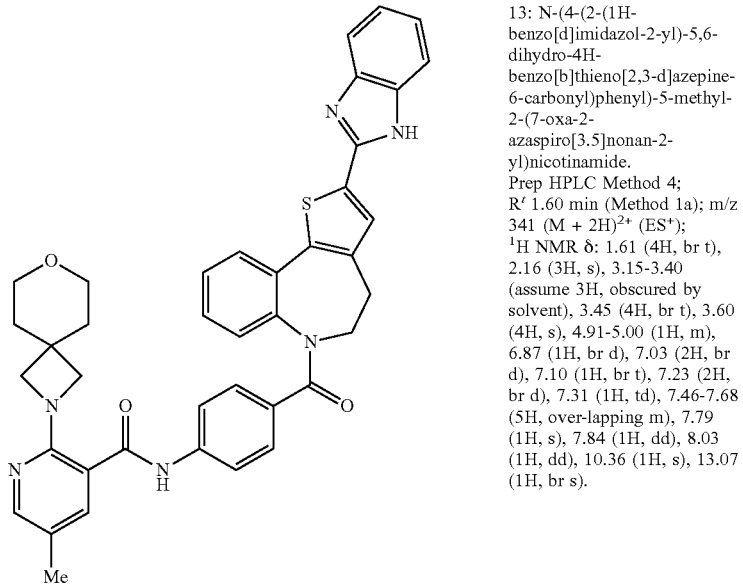

13: N-(4-(2-(1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide.
Prep HPLC Method 4;
R$^t$ 1.60 min (Method 1a); m/z 341 (M + 2H)$^{2+}$ (ES$^+$);
$^1$H NMR δ: 1.61 (4H, br t), 2.16 (3H, s), 3.15-3.40 (assume 3H, obscured by solvent), 3.45 (4H, br t), 3.60 (4H, s), 4.91-5.00 (1H, m), 6.87 (1H, br d), 7.03 (2H, br d), 7.10 (1H, br t), 7.23 (2H, br d), 7.31 (1H, td), 7.46-7.68 (5H, over-lapping m), 7.79 (1H, s), 7.84 (1H, dd), 8.03 (1H, dd), 10.36 (1H, s), 13.07 (1H, br s).

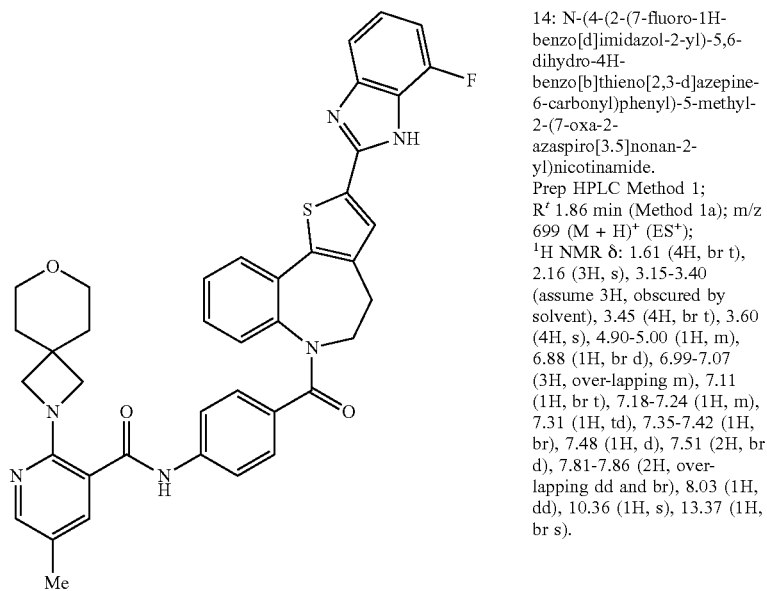

14: N-(4-(2-(7-fluoro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide.
Prep HPLC Method 1;
R$^t$ 1.86 min (Method 1a); m/z 699 (M + H)$^+$ (ES$^+$);
$^1$H NMR δ: 1.61 (4H, br t), 2.16 (3H, s), 3.15-3.40 (assume 3H, obscured by solvent), 3.45 (4H, br t), 3.60 (4H, s), 4.90-5.00 (1H, m), 6.88 (1H, br d), 6.99-7.07 (3H, over-lapping m), 7.11 (1H, br t), 7.18-7.24 (1H, m), 7.31 (1H, td), 7.35-7.42 (1H, br), 7.48 (1H, d), 7.51 (2H, br d), 7.81-7.86 (2H, over-lapping dd and br), 8.03 (1H, dd), 10.36 (1H, s), 13.37 (1H, br s).

TABLE 2-continued

Additional Compound Examples of the Invention
Structure, Example No., Name, Prep HPLC Method, Analytical and Spectral Data

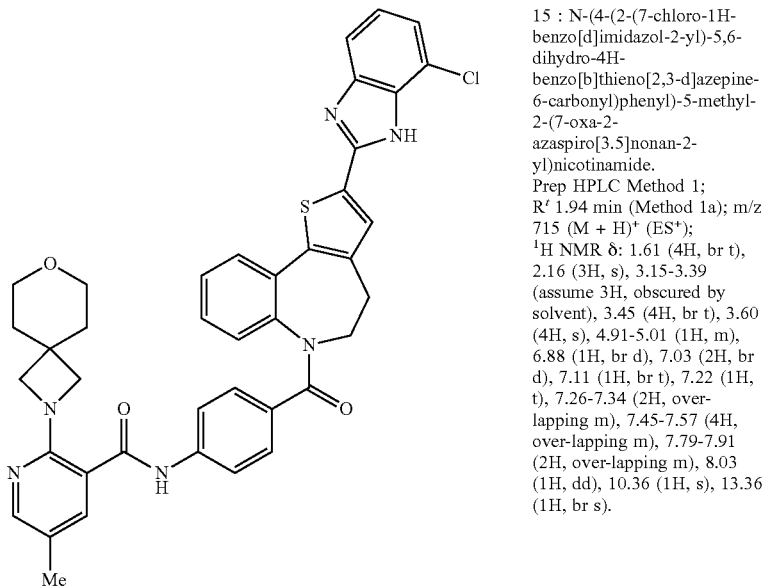

15 : N-(4-(2-(7-chloro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide.
Prep HPLC Method 1;
R$^t$ 1.94 min (Method 1a); m/z 715 (M + H)$^+$ (ES$^+$);
$^1$H NMR δ: 1.61 (4H, br t), 2.16 (3H, s), 3.15-3.39 (assume 3H, obscured by solvent), 3.45 (4H, br t), 3.60 (4H, s), 4.91-5.01 (1H, m), 6.88 (1H, br d), 7.03 (2H, br d), 7.11 (1H, br t), 7.22 (1H, t), 7.26-7.34 (2H, overlapping m), 7.45-7.57 (4H, overlapping m), 7.79-7.91 (2H, overlapping m), 8.03 (1H, dd), 10.36 (1H, s), 13.36 (1H, br s).

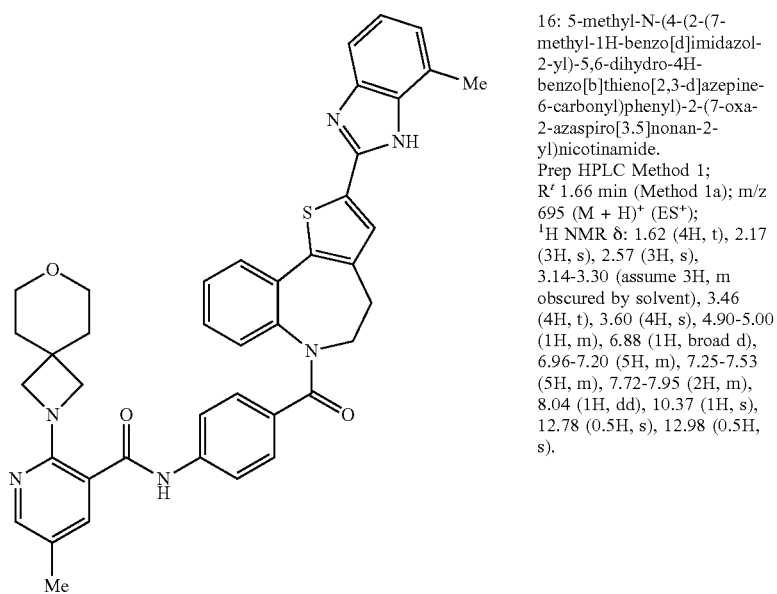

16: 5-methyl-N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide.
Prep HPLC Method 1;
R$^t$ 1.66 min (Method 1a); m/z 695 (M + H)$^+$ (ES$^+$);
$^1$H NMR δ: 1.62 (4H, t), 2.17 (3H, s), 2.57 (3H, s), 3.14-3.30 (assume 3H, m obscured by solvent), 3.46 (4H, t), 3.60 (4H, s), 4.90-5.00 (1H, m), 6.88 (1H, broad d), 6.96-7.20 (5H, m), 7.25-7.53 (5H, m), 7.72-7.95 (2H, m), 8.04 (1H, dd), 10.37 (1H, s), 12.78 (0.5H, s), 12.98 (0.5H, s).

TABLE 2-continued

Additional Compound Examples of the Invention
Structure, Example No., Name, Prep HPLC Method, Analytical and Spectral Data

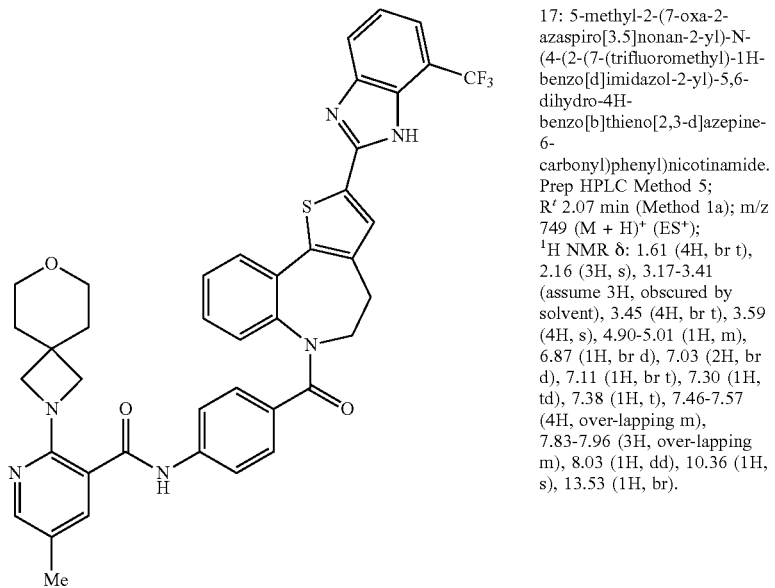

17: 5-methyl-2-(7-oxa-2-azaspiro[3.5]nonan-2-yl)-N-(4-(2-(7-(trifluoromethyl)-1H-benzo[d]imidazol-2-yl)-5,6-dihydro-4H-benzo[b]thieno[2,3-d]azepine-6-carbonyl)phenyl)nicotinamide.
Prep HPLC Method 5;
$R^t$ 2.07 min (Method 1a); m/z 749 (M + H)$^+$ (ES$^+$);
$^1$H NMR δ: 1.61 (4H, br t), 2.16 (3H, s), 3.17-3.41 (assume 3H, obscured by solvent), 3.45 (4H, br t), 3.59 (4H, s), 4.90-5.01 (1H, m), 6.87 (1H, br d), 7.03 (2H, br d), 7.11 (1H, br t), 7.30 (1H, td), 7.38 (1H, t), 7.46-7.57 (4H, over-lapping m), 7.83-7.96 (3H, over-lapping m), 8.03 (1H, dd), 10.36 (1H, s), 13.53 (1H, br).

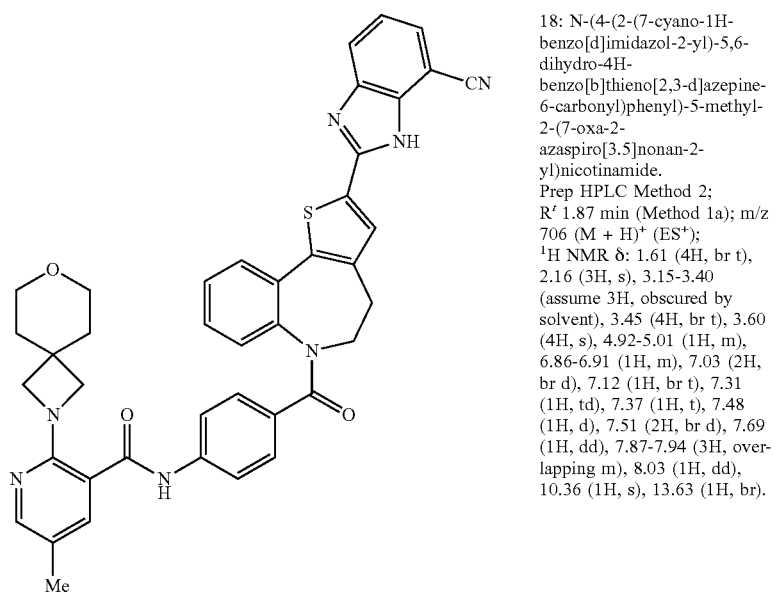

18: N-(4-(2-(7-cyano-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide.
Prep HPLC Method 2;
$R^t$ 1.87 min (Method 1a); m/z 706 (M + H)$^+$ (ES$^+$);
$^1$H NMR δ: 1.61 (4H, br t), 2.16 (3H, s), 3.15-3.40 (assume 3H, obscured by solvent), 3.45 (4H, br t), 3.60 (4H, s), 4.92-5.01 (1H, m), 6.86-6.91 (1H, m), 7.03 (2H, br d), 7.12 (1H, br t), 7.31 (1H, td), 7.37 (1H, t), 7.48 (1H, d), 7.51 (2H, br d), 7.69 (1H, dd), 7.87-7.94 (3H, over-lapping m), 8.03 (1H, dd), 10.36 (1H, s), 13.63 (1H, br).

TABLE 2-continued

Additional Compound Examples of the Invention
Structure, Example No., Name, Prep HPLC Method, Analytical and Spectral Data

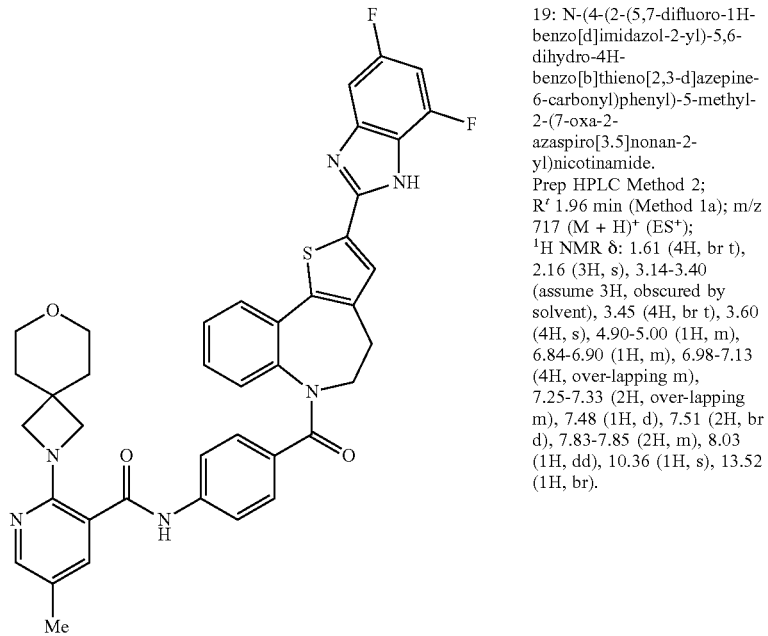

19: N-(4-(2-(5,7-difluoro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide.
Prep HPLC Method 2;
$R^t$ 1.96 min (Method 1a); m/z 717 (M + H)$^+$ (ES$^+$);
$^1$H NMR δ: 1.61 (4H, br t), 2.16 (3H, s), 3.14-3.40 (assume 3H, obscured by solvent), 3.45 (4H, br t), 3.60 (4H, s), 4.90-5.00 (1H, m), 6.84-6.90 (1H, m), 6.98-7.13 (4H, over-lapping m), 7.25-7.33 (2H, over-lapping m), 7.48 (1H, d), 7.51 (2H, br d), 7.83-7.85 (2H, m), 8.03 (1H, dd), 10.36 (1H, s), 13.52 (1H, br).

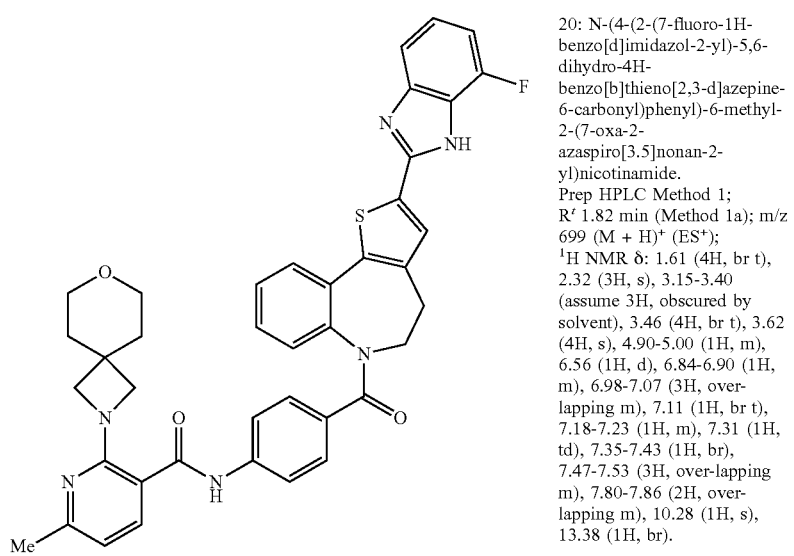

20: N-(4-(2-(7-fluoro-1H-benzo[d]imidazol-2-yl)-5,6-dihydro-4H-benzo[b]thieno[2,3-d]azepine-6-carbonyl)phenyl)-6-methyl-2-(7-oxa-2-azaspiro[3.5]nonan-2-yl)nicotinamide.
Prep HPLC Method 1;
$R^t$ 1.82 min (Method 1a); m/z 699 (M + H)$^+$ (ES$^+$);
$^1$H NMR δ: 1.61 (4H, br t), 2.32 (3H, s), 3.15-3.40 (assume 3H, obscured by solvent), 3.46 (4H, br t), 3.62 (4H, s), 4.90-5.00 (1H, m), 6.56 (1H, d), 6.84-6.90 (1H, m), 6.98-7.07 (3H, over-lapping m), 7.11 (1H, br t), 7.18-7.23 (1H, m), 7.31 (1H, td), 7.35-7.43 (1H, br), 7.47-7.53 (3H, over-lapping m), 7.80-7.86 (2H, over-lapping m), 10.28 (1H, s), 13.38 (1H, br).

TABLE 2-continued

Additional Compound Examples of the Invention
Structure, Example No., Name, Prep HPLC Method, Analytical and Spectral Data

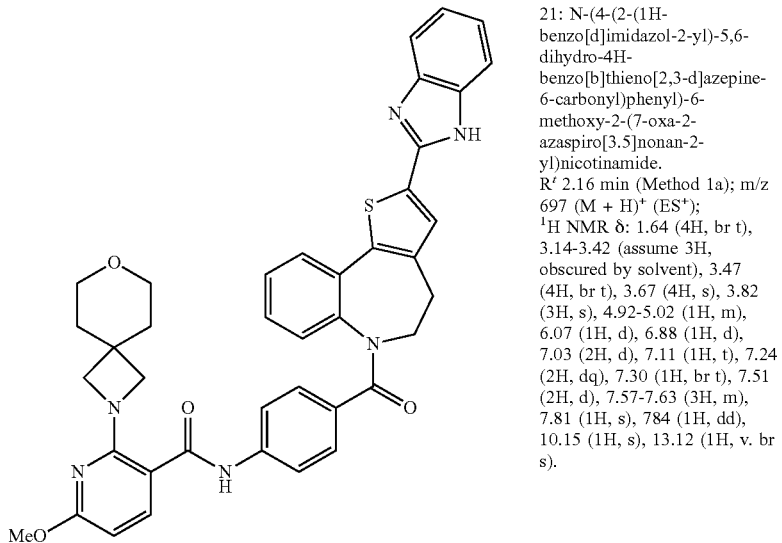

21: N-(4-(2-(1H-benzo[d]imidazol-2-yl)-5,6-dihydro-4H-benzo[b]thieno[2,3-d]azepine-6-carbonyl)phenyl)-6-methoxy-2-(7-oxa-2-azaspiro[3.5]nonan-2-yl)nicotinamide.
$R^t$ 2.16 min (Method 1a); m/z 697 (M + H)$^+$ (ES$^+$);
$^1$H NMR δ: 1.64 (4H, br t), 3.14-3.42 (assume 3H, obscured by solvent), 3.47 (4H, br t), 3.67 (4H, s), 3.82 (3H, s), 4.92-5.02 (1H, m), 6.07 (1H, d), 6.88 (1H, d), 7.03 (2H, d), 7.11 (1H, t), 7.24 (2H, dq), 7.30 (1H, br t), 7.51 (2H, d), 7.57-7.63 (3H, m), 7.81 (1H, s), 784 (1H, dd), 10.15 (1H, s), 13.12 (1H, v. br s).

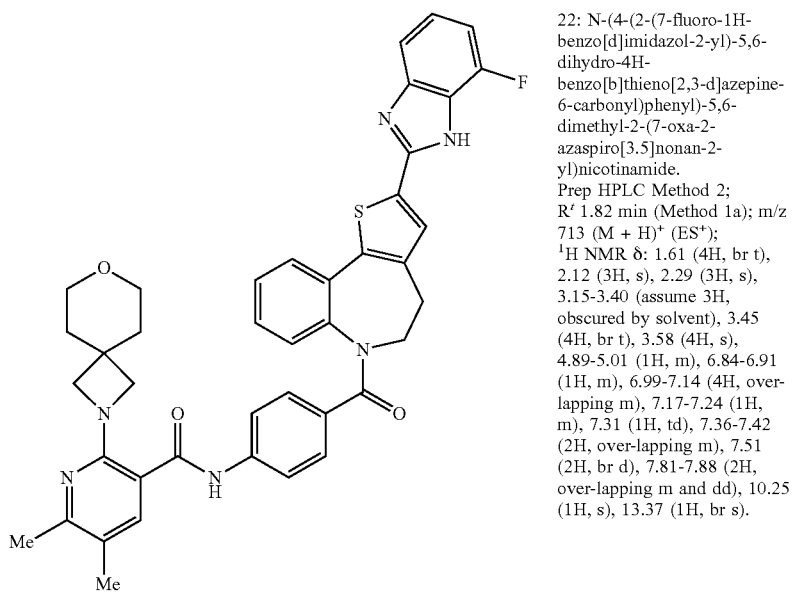

22: N-(4-(2-(7-fluoro-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide.
Prep HPLC Method 2;
$R^t$ 1.82 min (Method 1a); m/z 713 (M + H)$^+$ (ES$^+$);
$^1$H NMR δ: 1.61 (4H, br t), 2.12 (3H, s), 2.29 (3H, s), 3.15-3.40 (assume 3H, obscured by solvent), 3.45 (4H, br t), 3.58 (4H, s), 4.89-5.01 (1H, m), 6.84-6.91 (1H, m), 6.99-7.14 (4H, over-lapping m), 7.17-7.24 (1H, m), 7.31 (1H, td), 7.36-7.42 (2H, over-lapping m), 7.51 (2H, br d), 7.81-7.88 (2H, over-lapping m and dd), 10.25 (1H, s), 13.37 (1H, br s).

TABLE 2-continued

Additional Compound Examples of the Invention
Structure, Example No., Name, Prep HPLC Method, Analytical and Spectral Data

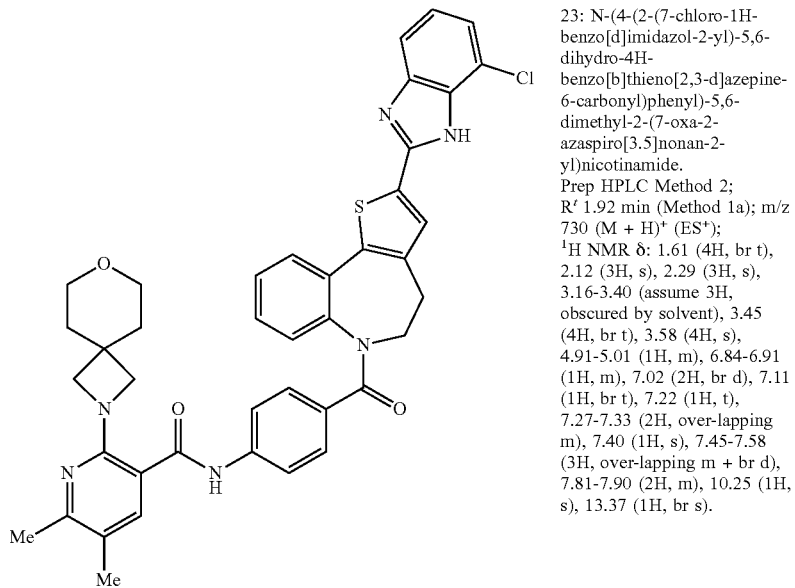

23: N-(4-(2-(7-chloro-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide.
Prep HPLC Method 2;
$R^t$ 1.92 min (Method 1a); m/z 730 (M + H)$^+$ (ES$^+$);
$^1$H NMR δ: 1.61 (4H, br t), 2.12 (3H, s), 2.29 (3H, s), 3.16-3.40 (assume 3H, obscured by solvent), 3.45 (4H, br t), 3.58 (4H, s), 4.91-5.01 (1H, m), 6.84-6.91 (1H, m), 7.02 (2H, br d), 7.11 (1H, br t), 7.22 (1H, t), 7.27-7.33 (2H, over-lapping m), 7.40 (1H, s), 7.45-7.58 (3H, over-lapping m + br d), 7.81-7.90 (2H, m), 10.25 (1H, s), 13.37 (1H, br s).

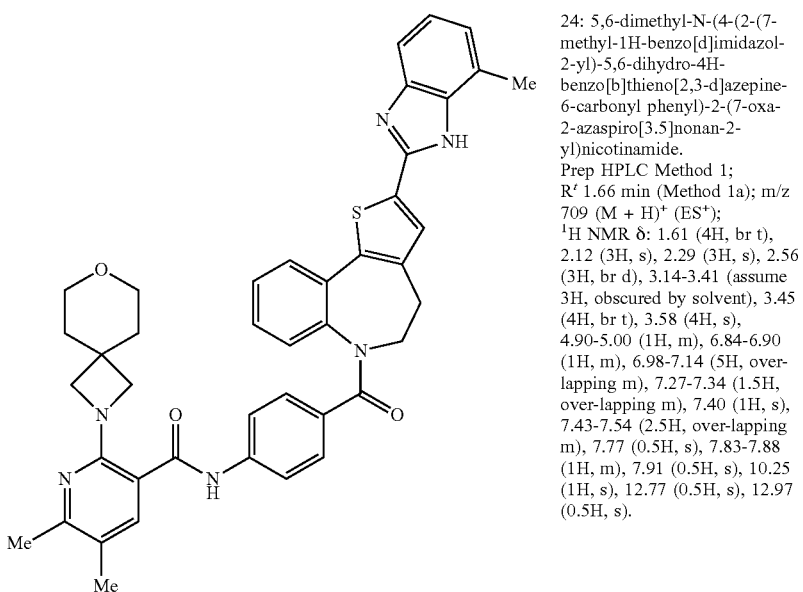

24: 5,6-dimethyl-N-(4-(2-(7-methyl-1H-benzo[d]imidazol-2-yl)-5,6-dihydro-4H-benzo[b]thieno[2,3-d]azepine-6-carbonyl phenyl)-2-(7-oxa-2-azaspiro[3.5]nonan-2-yl)nicotinamide.
Prep HPLC Method 1;
$R^t$ 1.66 min (Method 1a); m/z 709 (M + H)$^+$ (ES$^+$);
$^1$H NMR δ: 1.61 (4H, br t), 2.12 (3H, s), 2.29 (3H, s), 2.56 (3H, br d), 3.14-3.41 (assume 3H, obscured by solvent), 3.45 (4H, br t), 3.58 (4H, s), 4.90-5.00 (1H, m), 6.84-6.90 (1H, m), 6.98-7.14 (5H, over-lapping m), 7.27-7.34 (1.5H, over-lapping m), 7.40 (1H, s), 7.43-7.54 (2.5H, over-lapping m), 7.77 (0.5H, s), 7.83-7.88 (1H, m), 7.91 (0.5H, s), 10.25 (1H, s), 12.77 (0.5H, s), 12.97 (0.5H, s).

TABLE 2-continued

Additional Compound Examples of the Invention
Structure, Example No., Name, Prep HPLC Method, Analytical and Spectral Data

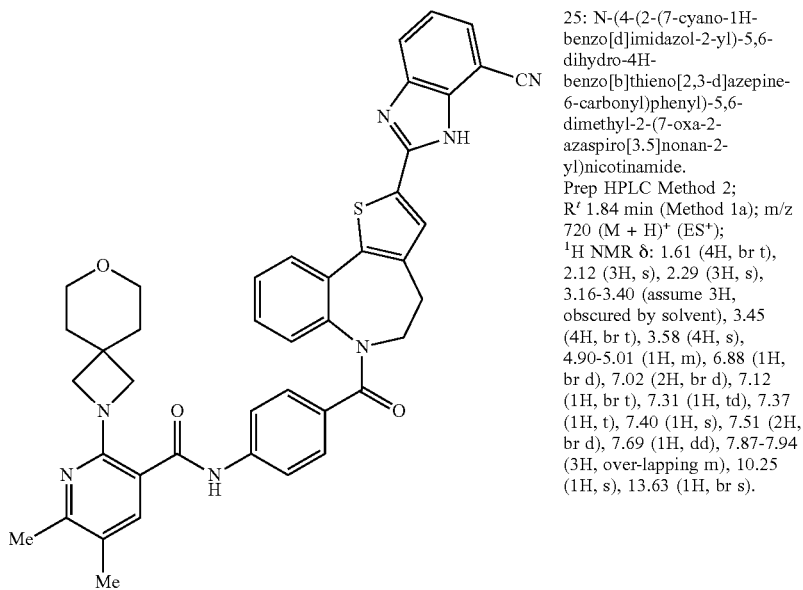

25: N-(4-(2-(7-cyano-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide.
Prep HPLC Method 2;
R' 1.84 min (Method 1a); m/z 720 (M + H)⁺ (ES⁺);
¹H NMR δ: 1.61 (4H, br t), 2.12 (3H, s), 2.29 (3H, s), 3.16-3.40 (assume 3H, obscured by solvent), 3.45 (4H, br t), 3.58 (4H, s), 4.90-5.01 (1H, m), 6.88 (1H, br d), 7.02 (2H, br d), 7.12 (1H, br t), 7.31 (1H, td), 7.37 (1H, t), 7.40 (1H, s), 7.51 (2H, br d), 7.69 (1H, dd), 7.87-7.94 (3H, over-lapping m), 10.25 (1H, s), 13.63 (1H, br s).

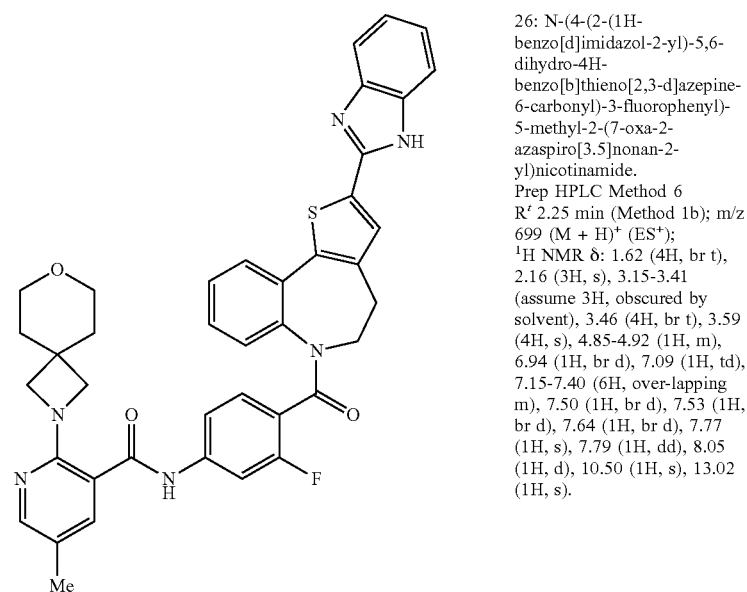

26: N-(4-(2-(1H-benzo[d]imidazol-2-yl)-5,6-dihydro-4H-benzo[b]thieno[2,3-d]azepine-6-carbonyl)-3-fluorophenyl)-5-methyl-2-(7-oxa-2-azaspiro[3.5]nonan-2-yl)nicotinamide.
Prep HPLC Method 6
R' 2.25 min (Method 1b); m/z 699 (M + H)⁺ (ES⁺);
¹H NMR δ: 1.62 (4H, br t), 2.16 (3H, s), 3.15-3.41 (assume 3H, obscured by solvent), 3.46 (4H, br t), 3.59 (4H, s), 4.85-4.92 (1H, m), 6.94 (1H, br d), 7.09 (1H, td), 7.15-7.40 (6H, over-lapping m), 7.50 (1H, br d), 7.53 (1H, br d), 7.64 (1H, br d), 7.77 (1H, s), 7.79 (1H, dd), 8.05 (1H, d), 10.50 (1H, s), 13.02 (1H, s).

TABLE 2-continued

Additional Compound Examples of the Invention
Structure, Example No., Name, Prep HPLC Method, Analytical and Spectral Data

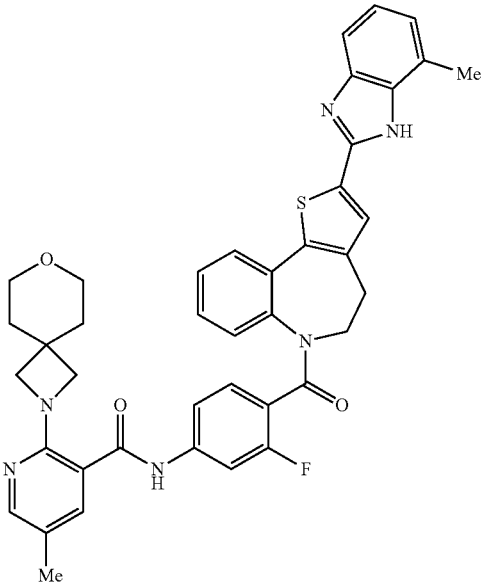 [SMILES: Cc1cnc(N2CC3(CCOCC3)C2)c(C(=O)Nc2ccc(C(=O)N3CCc4cc(-c5nc6cccc(C)c6[nH]5)sc4-c4ccccc43)c(F)c2)c1]

27: N-(3-fluoro-4-(2-(7-methyl-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide.
Prep HPLC Method 6
$R^t$ 2.38 min (Method 1b); m/z 713 $(M + H)^+$ $(ES^+)$;
$^1H$ NMR δ: 1.62 (4H, br t), 2.16 (3H, s), 2.56 (3H, br d), 3.15-3.42 (assume 3H, obscured by solvent), 3.46 (4H, br t), 3.59 (4H, s), 4.85-4.93 (1H, m), 6.93 (1H, br d), 7.01 (1H, br t), 7.07-7.21 (3H, over-lapping m), 7.25-7.46 (4H, over-lapping m), 7.50 (1H, d), 7.75 (0.5H, s), 7.80 (1H, dd), 7.89 (0.5H, s), 8.05 (1H, d), 10.50 (1H, s), 12.75 (0.5H, s), 12.95 (0.5H, s).

Biological Testing: Experimental Methods
Assessment of RSV Induced CPE in Hep2 Cells Hep2 cells were seeded ($10^3$/well/50 μL) in 384-well plates (Catalogue number 353962, BD Falcon, Oxford, UK) in 5% serum free-DMEM containing 2 mM L-glutamine and 1 mM sodium pyruvate one day before infection. RSV A2 strain (#0709161v, NCPV, Public Health England, Wiltshire) or RSV B Washington strain (VR-1580, ATCC, Manassas, Va. 20108) virus solutions were prepared in serum free-DMEM with 2 mM L-glutamine and 1 mM sodium pyruvate, and then added (50 μL/well) to achieve a final virus concentration of 1 MOI for RSV A and 0.1 MOI for RSV B. Simultaneously test compounds (0.5 μL DMSO solution) were added to 100 μL of Hep2 cell culture with virus solution to provide a final DMSO solution of 0.5%. Plates were incubated (37° C./5% $CO_2$) for 5 days for studies using RSV A2 strain or 6 days for those using RSV B strain, and then resazurin sodium salt (5 μL of 0.03% solution; Sigma-Aldrich, Dorset, UK) was added to each well and the plate incubated for a further 6 hr (37° C. and 5% $CO_2$). The fluorescence of each well [545 nm (excitation)/590 nm (emission)] was determined using a multi-scanner (Clariostar: BMG, Buckinghamshire, UK). The percentage inhibition for each well was calculated and the $IC_{50}$, $IC_{75}$ and $IC_{90}$ values were calculated from the concentration-response curve generated for each test compound.

Assessment of RSV F Protein Expression in BEAS2B Bronchial Epithelial Cells

An early event which follows the infection of epithelial cells by RSV is the expression of RSV F-protein on the cells' surface. BEAS2B cells (SV40-immortalised human bronchial epithelial cell line) were grown in 96 well plates. Once more than 70% confluent, cells were infected with RSV A2 (#0709161v, NCPV, Public Health England, Wiltshire) at an MOI of 0.01 in clear RPMI-1640 medium (Life technologies, Paisley, UK) with 2% FBS (Life technologies, Paisley, UK), and incubated for 3 days (37° C./5% $CO_2$).

Supernatant was aspirated and the cells were fixed with 4% formaldehyde (100 μL in PBS solution) for 20 min, washed 3 times with washing buffer (200 μL; PBS containing 0.05% Tween-20) and incubated with blocking solution (100 μL; 5% Marvel milk in PBS) for 1 hr. Cells were then washed with washing buffer (200 μL) and incubated for 1 hr at 37° C. with anti-RSV (2F7; mouse monoclonal, lot 160290, Cat. No. ab43812, Abcam plc, Cambridge, UK) F-fusion protein antibody (50 μL; prepared at a 1:1000 dilution in 5% milk/PBS-tween). After washing, cells were incubated with an HRP-conjugated anti-mouse IgG antibody (50 μL prepared at a 1:2000 dilution in 5% milk in PBS; lot 00095437, Cat. No. P0447, Dako UK Ltd, Cambridgeshire, UK) for 1 hr. Cells were washed twice with washing buffer and once with PBS. TMB substrate (100 μL; substrate reagent pack lot 320436, Cat. No. DY999, R&D Systems, Inc. Abingdon, UK) was then added and the reaction was stopped by the addition of aq sulfuric acid (50 μL; 2N). The resultant signal was determined colourimetrically (OD: 450 nm with a reference wavelength of 655 nm) in a microplate reader (Multiskan FC®, ThermoFisher Scientific). Cells were then washed and 1% crystal violet solution (50 μL; lot SLB4576, Cat. No. HT90132-1L, Sigma-Aldrich) was applied for 30 min. After washing with PBS (200 μL) 3 times, 1% SDS (100 μL) was added to each well, and plates were shaken lightly for 1 hr prior to reading the absorbance at 595 nm. The measured OD450-655 readings were corrected for cell number by dividing the OD450-655 by the OD595 readings. The percentage inhibition for each well was calculated and the $IC_{50}$ value derived from the concentration-response curve generated for each test compound.

Cell Viability: Resazurin Assay

Hep2 cells were seeded in 384-well plates ($10^3$/well/50 μL; BD Falcon Ref 353962) in FBS DMEM (5%, containing 2 mM L-glutamine and 1 mM sodium pyruvate) one day before experimentation. Serum-free DMEM (50 μL) was added to test wells while for control wells the media was removed and sterile water (100 μL) was added. Test compounds (0.5 µL DMSO solution) were added to give a final DMSO concentration of 0.5%. Hep2 cells were incubated with each test compound for 5 days (37° C./5% $CO_2$ in 5% FBS) and then resazurin stock solution (5 µL; 0.03%) was added to each well and the plate incubated further for a further 6 hrs (37° C./5% $CO_2$). The fluorescence of each well at 545 nm (excitation) and 590 nm (emission) was determined using a multi-scanner (Clariostar: BMG Labtech). The percentage loss of cell viability was calculated for each well relative to vehicle (0.5% DMSO) treatment.

Where appropriate, a $CC_{50}$ value was calculated from the concentration-response curve generated from the concentration-response curve for each test compound.

In Vitro Screening Results

The profiles of the compounds of the invention, as disclosed herein, are summarised below (Table 3) and demonstrate potent inhibitory activities against both RSV A2-induced CPE and (in many cases) RSV B-induced CPE in Hep2 cells. Furthermore, the compounds of the invention exhibit potent inhibition of RSV A2 F-protein expression in BEAS2B bronchial epithelial cells. No effects on cell viability, resulting from incubation with the compounds were detected.

TABLE 3

The effects of treatment with compound examples of formula (I) on RSV A2- and RSV B-induced CPE in Hep2 cells, on RSV A2 F-protein expression in BEAS2B bronchial epithelial cells and on cell viability.

| Com- | $IC_{50}/CC_{50}$ Values (nM) or Inhibition (%) at indicated concentration | | | | | |
|---|---|---|---|---|---|---|
| pound Exam- | RSV A2 CPE | | RSV B CPE | | RSV A2 | Cell |
| ple No. | $IC_{50}$ | % Inhibition[1] | $IC_{50}$ | % Inhibition[3] | F-protein $IC_{50}$ | Viability $CC_{50}$ |
| 1 | 0.21 | 100 | 84.7 | 100 | nt | >14700 |
| 2 | 0.23 | 90[2] | 9.6 | 100 | 1.6 | >14700 |
| 3 | 2.6 | 100[2] | 8.6 | 100 | 0.78 | >14100 |
| 4 | 0.66 | 86[2] | 13.3 | 100 | nt | >14400 |
| 5 | 6.9 | 100[2] | 36.1 | 92 | 0.11 | >14500 |
| 6 | 2.6 | 100[2] | 14.9 | 100 | 0.22 | >14100 |
| 7 | 0.12 | 100 | 28.7 | 100 | 0.94 | >15000 |
| 8 | 0.18 | 100 | 26.8 | 100 | nt | >14600 |
| 9 | 0.67 | 100 | 44.1 | 100 | nt | >14300 |
| 10 | 0.14 | 100 | 62.0 | 100 | nt | >13600 |
| 11 | 0.28 | 100 | 45.7 | 100 | nt | >14700 |
| 12 | 0.94 | 100 | 111 | 100 | 0.21 | >14500 |
| 13 | 0.085 | 100 | 0.99 | 100 | nt | >14700 |
| 14 | 0.24 | 93[2] | 0.99 | 100 | 0.31 | >14300 |
| 15 | 0.17 | 85 | 83.3 | 100 | nt | >14000 |
| 16 | 0.11 | 100 | 16.0 | 99 | nt | >14400 |
| 17 | 0.11 | 100 | 13.2 | 100 | nt | >13400 |
| 18 | 0.28 | 100 | 7.4 | 100 | nt | >14200 |
| 19 | 0.96 | 88[2] | 6.3 | 100 | nt | >14000 |
| 20 | 0.094 | 100 | 7.6 | 100 | nt | >14300 |
| 21 | 0.21 | 100 | 45.2 | 100 | nt | >14400 |
| 22 | 1.6 | 90[2] | 14.0 | 100 | nt | >14000 |
| 23 | 0.75 | 100 | 103 | 100 | nt | >13700 |
| 24 | 0.85 | 100 | 27.3 | 100 | nt | >14100 |
| 25 | 0.69 | 100[2] | 15.8 | 100 | nt | >13900 |
| 26 | 0.27 | 100[2] | 12.0 | 100 | nt | >14300 |
| 27 | 0.29 | 90 | 15.0 | 80 | nt | >14000 |

Table Footnotes:
[1]Inhibition (%) at 0.1 µg/mL;
[2]Inhibition (%) at 0.01 µg/mL;
[3]Inhibition (%) at 1 µg/mL; nt = not tested.

In Vivo Testing

Human RSV is able to infect and replicate in a number of animal species used for pre-clinical screening, thereby enabling the performance and profiles of novel anti-infective agents to be assessed and compared in vivo (Bern, et al., 2011). Although primate species can also be infected and studied, most work of this nature is conducted in mice or cotton rats. Both standard, inbred mouse strains and cotton rats are characterised as "semi-permissive" for the replication of human RSV, although significantly greater viral replication is seen in cotton rats compared to inbred mouse strains.

Compounds of the invention may be tested in the above mentioned in vivo systems.

In Vivo Pharmacokinetics

It is a commonly used procedure for pulmonary, therapeutic agents to be dosed into the lungs of animals, for example mice, and plasma collected at various time points after dosing in order to characterise the resulting systemic exposure to the administered compound.

The compounds of the invention may be tested in such above mentioned in vivo systems.

Summary

The in vitro antiviral activity of the compounds of the invention has been demonstrated by their cytoprotective effect on Hep2 cells, infected with RSV. In this assay system the inhibition of virus replication was detected and quantified from the resulting inhibition of virus-mediated CPE. It is particularly noteworthy that compounds of the invention are potent inhibitors of the CPE induced by the RSV A strain and (in many cases) the RSV B strain studied. The potent antiviral activity of compounds of formula (I) was also evident by their inhibition of RSV A2 F-protein expression in BEAS2B cells. The compounds of the invention appear to have low toxicity as measured by their effect in the cell viability assay. Compounds of the invention thus appear to have the attributes to be useful medicines for the treatment or prevention of RSV infection and associated diseases.

REFERENCES

Abman S. H., Ogle J. W., Butler-Simon N., Rumack C. M., and Accurso F. J. Role of respiratory syncytial virus in early hospitalizations for respiratory distress of young infants with cystic fibrosis. *J. Pediatr.*, 1988, 113, 826-30.

Bem R. A., Domachowske J. B. and Rosenberg, H. F. Animal models of human respiratory syncytial disease. *Am. J. Physiol.*, 2011. 301, L148-L156.

Hall C. B., Douglas R. G. Jr., Schnabel K. C. and Geiman J. M. Infectivity of respiratory syncytial virus by various routes of inoculation. *Infect. Immun.*, 1981, 33, 779-83.

Holt P. G. and Sly P. D. Interactions between RSV infection, asthma, and atopy: unraveling the complexities. *J. Exp. Med.*, 2002, 196, 1271-1275.

Johnson J. E., Gonzales R. A., Olson S. J., Wright P. F. and Graham, B. S. The histopathology of fatal untreated human respiratory syncytial virus infection. *Modern Pathology*, 2007, 20, 108-119.

Lee N., Lui G. C., Wong K. T., Li T. C., Tse E. C., Chan J. Y., Yu J., Wong S. S., Choi K. W., Wong R. Y., Ngai K. L., Hui D. S. and Chan P. K. High morbidity and mortality in adults hospitalized for respiratory syncytial virus infections. *Clin. Infect. Dis.*, 2013, 57, 1069-77.

Mohan A., Chandra S., Agarwal D., Guleria R., Broor S., Gaur B. and Pandey R. M. Prevalence of viral infection detected by PCR and RT-PCR in patients with acute exacerbation of COPD: A systematic review. *Respirology*, 2010, 15, 536-542.

Newcomb D. C. and Peebles R. S. Jr. Bugs and asthma: a different disease? *Proc. Am. Thorac. Soc.*, 2009, 6(3), 266-71.

Olivier A., Gallup J., de Macedo M. M. M. A., Varga S. M. and Ackermann M. Human respiratory syncytial virus A2 strain replicates and induces innate immune responses by respiratory epithelia of neonatal lambs. *Int. J. Exp. Pathol.* 2009, 90, 431-438.

Panayiotou C., Richter J., Koliou M., Kalogirou N., Georgiou E. and Christodoulou C. Epidemiology of respiratory syncytial virus in children in Cyprus during three consecutive winter seasons (2010-2013): age distribution, seasonality and association between prevalent genotypes and disease severity. *Epidemiol. Infect.*, 2014, January 24, 1-6.

Peesapati V. and Lingaiah N. Thiopheno[3,2][1]benzazepine, Benzo[3,4]cyclohepta[2,1-b]thiophenes, Thiazolo[5,4-d][1]benzazepine and Benzo[3,4]cyclohepta[2,1-d]thiazoles. *Org. Prep. & Proced. Int.*, 1993, 25(5), 602-606.

Walsh E. E., McConnochie K. M., Long C. E. and Hall C. B. Severity of respiratory syncytial virus infection is related to virus strain. *J. Infect. Dis.*, 1997, 175, 814-20.

Zhang Z-Y., Du L-N., Chen X., Zhao Y., Liu E-M., Yang X-Q. and Zhao X-D. Genetic variability of respiratory syncytial viruses (RSV) prevalent in Southwestern China from 2006 to 2009: emergence of subgroup B and A RSV as dominant strains. *J. Clin. Microbiol.*, 2010, 48, 1201-7.

Zhu Q., McAuliffe J. M., Patel N. K., Palmer-Hill F. J., Yang C. F., Liang B., Su L., Zhu W., Wachter L., Wilson S., MacGill R. S., Krishnan S., McCarthy M. P., Losonsky G. A. and Suzich J. A. Analysis of respiratory syncytial virus preclinical and clinical variants resistant to neutralization by monoclonal antibodies palivizumab and/or motavizumab. *J Infect. Dis.*, 2011, 203, 674-82

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A compound of formula (I):

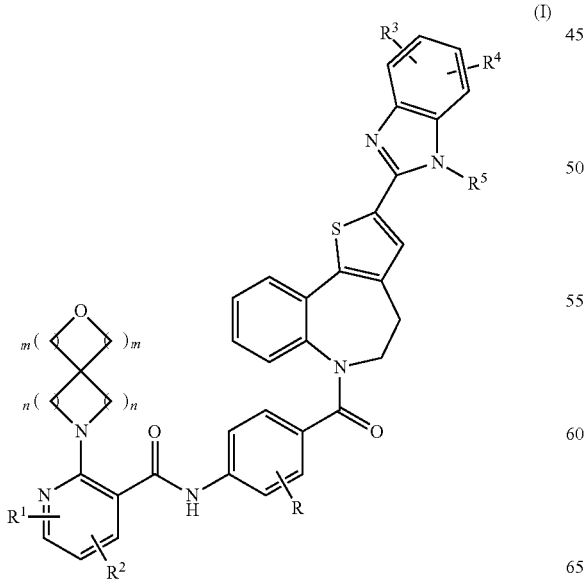

wherein:
R represents hydrogen or halo;
$R^1$ represents hydrogen, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy or $C_{1-4}$ haloalkoxy;
$R^2$ represents hydrogen, halo, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy, $C_{1-4}$ haloalkoxy or cyano;
$R^3$ represents hydrogen, hydroxy, halo, cyano, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{0-3}$ alkylene$C_{3-6}$ cycloalkyl, $C_{0-3}$ alkylene-heterocyclyl, $C_{0-3}$ alkyleneamino, $C_{0-3}$ alkyleneNHC$_{1-5}$ alkyl, $C_{0-3}$ alkyleneN(C$_{1-5}$ alkyl)$_2$, $C_{1-5}$ acyl amino, $C_{0-3}$ alkyleneC(O)NHC$_{0-3}$ alkyl, $C_{0-3}$ alkyleneC(O)N(C$_{1-3}$ alkyl)$_2$, $C_{1-3}$ alkyleneN(C$_{0-3}$ alkyl)C(O)C$_{0-3}$ alkyl, $C_{0-3}$ alkyleneN(C$_{0-3}$ alkyl)C(O)NHC$_{0-3}$ alkyl, $C_{0-3}$ alkyleneN(C$_{0-3}$ alkyl)C(O)N(C$_{1-3}$ alkyl)$_2$, $C_{0-3}$ alkyleneN(C$_{0-3}$ alkyl)S(O)$_q$C$_{1-6}$ alkyl, S(O)$_q$C$_1$-6 alkyl, $C_{0-3}$ alkyleneS(O)$_q$NHC$_{0-3}$ alkyl or $C_{0-3}$ alkyleneS(O)$_q$N(C$_{1-3}$ alkyl)$_2$;
$R^4$ represents hydrogen, halo, cyano, $C_{1-4}$ alkyl, $C_{2-4}$ alkenyl, $C_{2-4}$ alkynyl, $C_{1-4}$ haloalkyl, $C_{0-3}$ alkyleneC$_{3-6}$ cycloalkyl, $C_{1-4}$ alkoxy or $C_{1-4}$ haloalkoxy;
$R^5$ represents hydrogen, $C_{1-6}$ alkyl, $C_{1-6}$ haloalkyl, $C_{0-3}$ alkyleneC$_{3-6}$ cycloalkyl, $C_{2-3}$ alkyleneC$_{1-3}$ alkoxy, $C_{2-3}$ alkyleneC$_{1-3}$ haloalkoxy or $C_{2-3}$ alkyleneOH; and
m, n and q represent integers which may independently be selected from 1 and 2;
or a pharmaceutically acceptable salt thereof.

2. A compound of formula (I) according to claim 1 wherein n is 1 and m is 2.

3. A compound of formula (I) according to claim 1 which is a compound of formula (Ib)

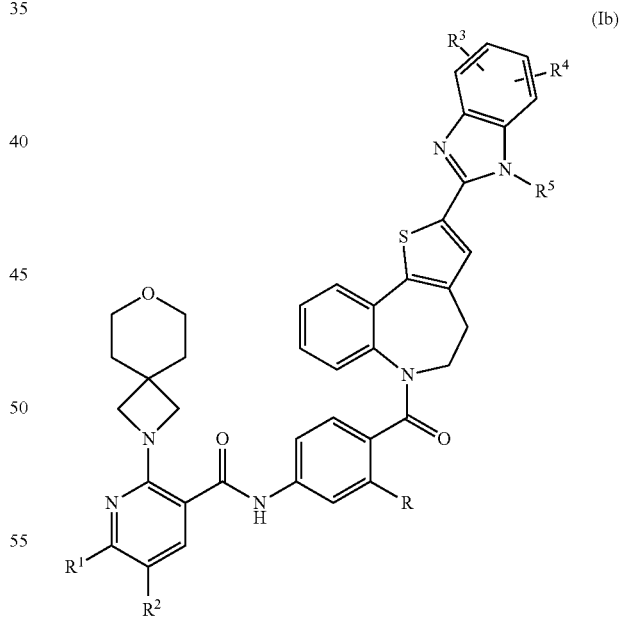

wherein R, $R^2$, $R^3$, $R^4$ and $R^5$ are as defined in claim 1.

4. A compound of formula (I) according to claim 1 wherein R represents hydrogen.

5. A compound of formula (I) according to claim 1 wherein R represents fluoro.

6. A compound of formula (I) according to claim 1 wherein $R^1$ is selected from hydrogen, $C_{1-4}$ alkyl and $C_{1-4}$ alkoxy.

7. A compound of formula (I) according to claim 1 wherein $R^2$ is selected from hydrogen and $C_{1-4}$ alkyl.

8. A compound of formula (I) according to claim 1 wherein one of $R^1$ and $R^2$ is methyl and the other is hydrogen or methyl.

9. A compound of formula (I) according to claim 1 wherein $R^3$ is selected from hydrogen, hydroxy, halo, cyano, $C_{1-4}$ alkyl, $C_{2-4}$ alkenyl, $C_{2-4}$ alkynyl, $C_{1-4}$ haloalkyl, $C_{3-6}$ cycloalkyl, $C_{1-4}$ alkoxy and $C_{1-4}$ haloalkoxy.

10. A compound of formula (I) according to claim 9 wherein $R^3$ is selected from hydrogen, halo, cyano, $C_{1-4}$ alkyl, $C_{2-4}$ alkenyl, $C_{2-4}$ alkynyl, $C_{1-4}$ haloalkyl, $C_{1-4}$ alkoxy and $C_{1-4}$ haloalkoxy.

11. A compound of formula (I) according to claim 10 wherein $R^3$ is selected from hydrogen, halo, cyano, $C_{1-4}$ alkyl and $C_{1-4}$ haloalkyl.

12. A compound of formula (I) according to claim 11 wherein $R^3$ is selected from halo, methyl, trifluoromethyl and cyano.

13. A compound of formula (I) according to claim 1 wherein $R^4$ is selected from hydrogen, halo, cyano, $C_{1-4}$ alkyl, $C_{2-4}$ alkenyl, $C_{2-4}$ alkynyl, $C_{1-4}$ haloalkyl, $C_{1-4}$ alkoxy and $C_{1-4}$ haloalkoxy.

14. A compound of formula (I) according to claim 13 wherein $R^4$ is selected from hydrogen and halo.

15. A compound of formula (I) according to claim 1 wherein $R^5$ is selected from hydrogen, $C_{1-6}$ alkyl, $C_{1-6}$ haloalkyl, $C_{0-3}$ alkylene$C_{3-6}$ cycloalkyl and $C_{2-3}$ alkylene$C_{1-3}$ alkoxy.

16. A compound of formula (I) according to claim 15 wherein $R^5$ is selected from hydrogen and $C_{1-4}$ alkyl.

17. A compound of formula (I) according to claim 16 wherein $R^5$ is hydrogen.

18. A compound according to claim 1 which is selected from the group consisting of:
N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
N-(4-(2-(1H-benzo[d]imidazol-2-yl)-5,6-dihydro-4H-benzo[b]thieno[2,3-d]azepine-6-carbonyl)phenyl)-6-methyl-2-(7-oxa-2-azaspiro[3,5]nonan-2-yl)nicotinamide;
N-(4-(2-(1H-benzo[d]imidazol-2-yl)-5,6-dihydro-4H-benzo[b]thieno[2,3-d]azepine-6-carbonyl)phenyl)-5-ethyl-2-(7-oxa-2-azaspiro[3.5]nonan-2-yl)nicotinamide;
N-(4-(2-(1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
N-(4-(2-(7-fluoro-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
N-(4-(2-(7-chloro-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
2-(7-oxa-2-azaspiro[3.5]nonan-2-yl)-N-(4-(2-(7-(trifluoromethyl)-1H-benzo[d]imidazol-2-yl)-5,6-dihydro-4H-benzo[b]thieno[2,3-d]azepine-6-carbonyl)phenyl)nicotinamide;
N-(4-(2-(6-methyl-1H-benzo[d]imidazol-2-yl)-5,6-dihydro-4H-benzo[b]thieno[2,3d]azepine-6-carbonyl)phenyl)-2-(7-oxa-2-azaspiro[3.5]nonan-2-yl)nicotinamide;
N-(4-(2-(7-cyano-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
N-(4-(2-(1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;
N-(4-(2-(7-fluoro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;
N-(4-(2-(7-chloro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;
5-methyl-N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
5-methyl-2-(7-oxa-2-azaspiro[3.5]nonan-2-yl)-N-(4-(2-(7-(trifluoromethyl)-1H-benzo[d]imidazol-2-yl)-5,6-dihydro-4H-benzo[b]thieno[2,3-d]azepine-6-carbonyl)phenyl)nicotinamide;
N-(4-(2-(7-cyano-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;
N-(4-(2-(5,7-difluoro-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;
N-(4-(2-(7-fluoro-1H-benzo[d]imidazol-2-yl)-5,6-dihydro-4H-benzo[b]thieno[2,3-d]azepine-6-carbonyl)phenyl)-6-methyl-2-(7-oxa-2-azaspiro[3.5]nonan-2-yl)nicotinamide;
N-(4-(2-(1H-benzo[d]imidazol-2-yl)-5,6-dihydro-4H-benzo[b]thieno[2,3-d]azepine-6-carbonyl)phenyl)-6-methoxy-2-(7-oxa-2-azaspiro[3.5]nonan-2-yl)nicotinamide;
N-(4-(2-(7-fluoro-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide;
N-(4-(2-(7-chloro-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide;
5,6-dimethyl-N-(4-(2-(7-methyl-1H-benzo[d]imidazol-2-yl)-5,6-dihydro-4H-benzo[b]thieno[2,3-d]azepine-6-carbonyl)phenyl)-2-(7-oxa-2-azaspiro[3.5]nonan-2-yl)nicotinamide;
N-(4-(2-(7-cyano-1H-benzo[d]imidazol-2-yl)-5,6-dihydro-4H-benzo[b]thieno[2,3-d]azepine-6-carbonyl)phenyl)-5,6-dimethyl-2-(7-oxa-2-azaspiro[3.5]nonan-2-yl)nicotinamide;
N-(4-(2-(1H-benzo[d]imidazol-2-yl)-5,6-dihydro-4H-benzo[b]thieno[2,3-d]azepine-6-carbonyl)-3-fluorophenyl)-5-methyl-2-(7-oxa-2-azaspiro[3.5]nonan-2-yl)nicotinamide and
N-(3-fluoro-4-(2-(7-methyl-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;
and pharmaceutically acceptable salts of any one thereof.

19. A compound according to claim 1 which is selected from the group consisting of:

N-(4-(2-(7-ethyl-1H-benzo[d]imidazol-2-yl)-5,6-dihydro-4H-benzo[b]thieno[2,3-d]azepine-6-carbonyl)phenyl)-5-methyl-2-(7-oxa-2-azaspiro[3.5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-5-ethynyl-2-(7-oxa-2-azaspiro[3,5]nonan-2-yl)nicotinamide;

N-(4-(2-(1H-benzo[d]imidazol-2-yl)-5,6-dihydro-4H-benzo[b]thieno[2,3-d]azepine-6-carbonyl)phenyl)-5-cyclopropyl-2-(7-oxa-2-azaspiro[3,5]nonan-2-yl)nicotinamide;

and pharmaceutically acceptable salts of any one thereof.

20. A method of treatment of a subject infected with RSV infection or a method of prevention or treatment of diseases associated with RSV infection in a subject which comprises administering to said subject an effective amount of a compound according to claim 1.

21. A method according to claim 20 wherein the RSV infection is infection by viruses of the RSV A strain and/or viruses of the RSV B strain.

22. A pharmaceutical composition comprising a compound according to claim 1 optionally in combination with one or more pharmaceutically acceptable diluents or carriers.

23. A pharmaceutical composition according to claim 22 which comprises a second or further active ingredient.

24. A composition according to claim 23 wherein the second or further active ingredient is selected from anti-viral agents and anti-inflammatory agents.

\* \* \* \* \*